US008741868B2

(12) United States Patent
Chun et al.

(10) Patent No.: US 8,741,868 B2
(45) Date of Patent: Jun. 3, 2014

(54) PHARMACEUTICAL COMPOSITION INCLUDING AN HIF-2 ALPHA INHIBITOR AS AN ACTIVE INGREDIENT FOR PREVENTING OR TREATING ARTHRITIS

(75) Inventors: Jang-Soo Chun, Buk-gu Gwangju (KR); Si Young Yang, Buk-gu Gwangju (KR)

(73) Assignee: Gwangju Institute of Science and Technology, Buk-Gu, Gwangju (KR)

( * ) Notice: Subject to any disclaimer, the term of this patent is extended or adjusted under 35 U.S.C. 154(b) by 0 days.

(21) Appl. No.: 13/699,226

(22) PCT Filed: Aug. 31, 2010

(86) PCT No.: PCT/KR2010/005889
§ 371 (c)(1),
(2), (4) Date: Mar. 28, 2013

(87) PCT Pub. No.: WO2011/145777
PCT Pub. Date: Nov. 24, 2011

(65) Prior Publication Data
US 2013/0236531 A1    Sep. 12, 2013

(30) Foreign Application Priority Data
May 20, 2010  (KR) .................. 10-2010-0047485

(51) Int. Cl.
A61K 48/00     (2006.01)
C12N 15/11     (2006.01)
C07H 21/02     (2006.01)
C07H 21/04     (2006.01)

(52) U.S. Cl.
USPC ....................... 514/44 A; 536/24.5

(58) Field of Classification Search
USPC ........................... 514/44; 536/24.5
See application file for complete search history.

(56) References Cited

U.S. PATENT DOCUMENTS
2005/0148496 A1    7/2005    Defranoux et al.

OTHER PUBLICATIONS

Yang et al. (Nature Medicine, 2010 vol. 16, No. 6:687-694).*
Bohensky, Jolene, et al., "Regulation of Autophagy in Human and Murine Cartilage Hypoxia-Inducible Factor 2 Suppresses Chondrocyte Autophagy," Arthritis & Rheumatism, May 2009, pp. 1406-1415, vol. 60, No. 5, American College of Rheumatology.
Lafont, Jerome, E., et al., "Hypoxia-Inducible Factor 2α is Essential for Hypoxic Induction of the Human Articular Chondrocyte Phenotype," Arthritis & Rheumatism, Oct. 2007, pp. 3297-3306, vol. 56, No. 10, American College of Rheumatology.

* cited by examiner

Primary Examiner — Terra Cotta Gibbs
(74) Attorney, Agent, or Firm — Nath, Goldberg & Meyer; Tanya E. Harkins

(57) ABSTRACT

The present invention relates to a pharmaceutical composition for preventing or treating arthritis, including, as an active ingredient, a material which inhibits the expression of the hypoxia-inducible factor-2α (HIF-2α) gene or the activity of the HIF-2α protein. According to the present invention, the HIF-2α of the present invention increases the expression thereof in chondrocytes or tissue in which osteoarthritis is induced, and triggers the expression of various cartilage degeneration factors and the activation of mitogen-activated protein (MAP) kinase. In addition, when HIF-2α is inhibited, the expression level of cartilage degeneration factors and the phosphorylation of MAP kinase are significantly reduced by the inhibited degree of HIF-2α. Thus, the composition of the present invention may be applied to the prevention or treatment of arthritis, and may be used for the development of therapeutics for arthritis.

3 Claims, 39 Drawing Sheets

Fig. 6b

| Promoter | Double strand oligonucleotide sequences | |
|---|---|---|
| MMP1 | AGGATTTCCTTTT CGTG AGAATGTCTTCCC | 128 |
| ΔMMP1 | AGGATTTCCTTTT AAAG AGAATGTCTTCCC | 129 |
| MMP3 | TTAGGCCAGGTGC CGTG ACCCATGTCTGTA | 130 |
| ΔMMP3 | TTAGGCCAGGTGC AAAG ACCCATGTCTGTA | 131 |
| Mmp9 | TCAACTGAAGGTCT CGTG AACACTGCTGAAA | 132 |
| ΔMmp9 | TCAACTGAAGGTCT AAAG AACACTGCTGAAA | 133 |
| MMP12 | TAACACACTCTTA CGTG CACCCTACCGCAC | 134 |
| ΔMMP12 | TAACACACTCTTA AAAG CACCCTACCGCAC | 135 |
| MMP13 | TTTGGTCCAATAT CGTG AACTTCAGGTAGA | 136 |
| ΔMMP13 | TTTGGTCCAATAT AAAG AACTTCAGGTAGA | 137 |
| Ptgs2 | TCGTCTTCTCATTTG CGTG GGTAAAGCCTGCC | 138 |
| ΔPtgs2 | TCGTCTTCTCATTTG AAAG GGTAAAGCCTGCC | 139 |
| Nos2 | TTTTGAAGTGACTA CGTG CTGCCTAGGGGCCA | 140 |
| ΔNos2 | TTTTGAAGTGACTA AAAG CTGCCTAGGGGCCA | 141 |
| Adamts4 | GGAGCAGAAAGAACC CGTG GGCACTTTTCCTGA | 142 |
| ΔAdamts4 | GGAGCAGAAAGAACC AAAG GGCACTTTTCCTGA | 143 |

SEQUENCE LISTING

<160> NUMBER OF SEQ ID NOS: 143

<210> SEQ ID NO 1
<211> LENGTH: 5352
<212> TYPE: DNA
<213> ORGANISM: Mus musculus

<400> SEQUENCE: 1 tttttttct tttttcttt ttcttttttt cttttctttt tttggttggt tggttttgat    60

```
ttgtcagatc ccagaaaagt gactcctgtt cggggctaaa cggaactcca ggtcccttgt    120
cgctgctctc tctctctttt ggcgtcttac aacctcctcc cactcctttc cccggccccg    180
cctcctcctg caggttcctc cccgtcaccc ccctcctccc tcctcctcct ccgcacctag    240
ccagccctct gcaaacttcc acctgattga gcgggactct cggacctgcg agcactaaag    300
acctttcaca cctgcccggg cgacagagag ctgcggaggg ccacagcaaa gagagcggct    360
gcagccccta cggggttaag gaacccaggt gctccgggtc tcggagggcc acggcgacaa    420
tgacagctga caaggagaaa aaaggagca gctcagagct gaggaaggag aaatcccgtg    480
atgccgcgag gtgccggcgc agcaaggaga cggaggtctt ctatgagttg gctcatgagt    540 tgccctgcc tcacagtgtg agctcccacc tggacaaagc ctccatcatg cgcctggcca    600
tcagcttcct tcggacacat aagctcctgt cctcagtctg ctctgaaaat gaatctgaag    660
ctgaggccga ccagcaaatg gataacttgt acctgaaagc cttggagggt tcattgctg    720 tggtgaccca agacggtgac atgatctttc tgtcggaaaa catcagcaag ttcatgggac    780
ttactcaggt agaactaaca ggacacagca tctttgactt cactcatcct tgcgaccatg    840
aggagatccg tgagaacctg actctcaaaa acggctctgg ttttgggaag aagagcaaag    900
acgtgtccac cgagcgtgac ttcttcatga ggatgaagtg cacggtcacc aacagaggcc    960
ggactgtcaa cctcaagtcg gccacctgga aggtcctgca ctgcaccggg caagtgagag    1020
tctacaacaa ctgcccccct cacagtagcc tctgtggctc caaggagccc ctgctgtcct    1080
gccttatcat catgtgtgag ccaatccagc acccatccca catggacatc cccctggaca    1140
gcaagacttt cctgagccgc cacagcatgg acatgaagtt cacctactgt gacgacagaa    1200
tcttggaact gattggttac caccccgagg agctacttgg acgctctgcc tatgagttct    1260
accatgccct ggattcggag aacatgacca aaagtcacca gaacttgtgc accaaggggc    1320
aggtggtatc tggccagtac cggatgctag ccaaacacgg aggatatgtg tggctggaga    1380
cccaggggac ggtcatctac aaccccgca acctgcagcc tcagtgtatc atgtgtgtca    1440
actatgtgct gagtgagatc gagaagaacg acgtggtgtt ctccatggac agaccgaat    1500 ccctgttcaa gccacacctg atggccatga acagcatctt tgacagcagt gacgatgtgg    1560
ctgtaactga gaagagcaac tacctgttca ccaaactgaa ggaggagccc gaggaactgg    1620
cccagttggc ccccaccca ggagatgcca ttatttctct cgatttcgga agccagaact    1680
tcgatgaacc ctcagcctat ggcaaggcca tccttccccc gggccagcca tgggtctcgg    1740
ggctgaggag ccacagtgcc cagagcgagt ccggagcct gccagccttc actgtgcccc    1800
aggcagacac cccagggaac actacaccca gtgcttcaag cagcagtagc tgctccacgc    1860
ccagcagccc tgaggactac tattcatcct tggagaatcc cttgaagatc gaagtgattg    1920
agaagctttt cgccatggac acggagccga gggacccggg cagtacccag acggacttca    1980
gtgaactgga tttggagacc ttggcaccct acatccctat ggacggcgag gacttccagc    2040
tgagccccat ctgcccagag gagccgctca tgccagagag ccccagccc accccccagc    2100 actgcttcag taccatgacc agcatcttcc agccgctcac cccgggggcc acccacggcc    2160
ccttcttcct cgataagtac ccgcagcagt ggaaagcag gaagacagag tctgagcact    2220
ggcccatgtc ttccatcttc tttgatgctg ggagcaaagg gtcccgtgtct ccatgctgtg    2280 gccaggccag caccctctc tcttctatgg gaggcagatc caacacgcag tggccccgg    2340 atccaccatt acatttcggc cctactaagt ggcctgtggg tgatcagagt gctgaatccc    2400
tgggagccct gccggtgggg tcatcgcagt tggaacctcc gagcgccccg cctcatgtct    2460
```

```
ccatgttcaa gatgaggtct gcaaaggact tcggggcccg aggtccatac atgatgagcc    2520
cagccatgat cgccctgtcc aacaagctga agctaaagcg gcagctggag tatgaggagc    2580
aagccttcca agacacaagc ggggggggacc ctccaggcac cagcagttca cacttgatgt   2640
ggaaacgtat gaagagcctc atgggcggga cctgtccttt gatgcctgac aagaccatca    2700
gtgcgaacat ggcccccgat gaattcaccc aaaaatctat gagaggcctg gccagccac    2760 tgagacacct gccacctccc cagccaccat ctaccaggag ctcaggggag aacgccaaga    2820
ctgggttccc gccacagtgc tatgcctccc agttccagga ctacggtcct ccaggagctc    2880
aaaaggtgtc aggcgtggcc agtcgactgc tggggccatc gttcgagcct tacctgttgc    2940
cggaactgac cagatatgac tgtgaggtga acgtgcccgt gcctggaagc tccacactcc    3000
tgcaggggag agaccttctc agagctctgg accaggccac ctgagccagg gcctctggcc    3060
gggcatgccc ctgcctgccc cgccgtcttg acctgccagc ttcacttcca tctgtgttgc    3120
tattaggtat ctctaacacc agcacacttc ttacgagatg tactcaacct ggcctactgg    3180
ccaggtcacc aagcagtggc ctttatctga catgctcact ttattatcca tgttttaaaa    3240
atacatagtt gttgtacctg ctatgtttta ccgttgatga aagtgttctg aaattttata    3300
agatttcccc ctccctccct cccttgaatt acttctaatt tatattcccc aaaggttttt    3360
ctctctctca ttcatatcca tactaacaag catggtggct ggtgcctctc cctaggaaag    3420
ctttggcgtc attcaactca agtgttcttg ttcttgttgc caaagagaaa aggattttcc    3480
tccactgtgg attctccctc tcccccaccc ccacatacac acacacacac acaccccct    3540 acacacatat acacacatgc acgtatgcgt gcacacacac acacacacac acacacacac    3600
acacacaccc ctacacacac acacacacac acacatatac acacacacac acacacacac    3660
acacacccct acacacatat acacacatgc acgtatgcgt gcacacacac acacacacac    3720
acacacaccc ctacacacat atacacacat gcacgtatgc gtgcacacac acacacacac    3780
acacacatct aatcaccata ttgtaaaatt ttgtgttttt aaagccaact cttttgctccg    3840 gttttttcat acgacttagt atggggcaaa aaagcaatgt gaagaatcaa ctctagggtt    3900
acctgtgaag ccacgcggtg gtgttcgaag ctgtctggta atgcccccat ctctccccgg    3960
gtccagtgga ttttttttaac tattattcaa aagcaaaact gagttttgtt ttgtttggtt    4020
ttttaagaag aatttatatc cgggtttagt gtttatcata tatatgggta ctctgtaata    4080
tctaaaagct tagaaatggg atcttgctca caagaatcac ttttaagatc ttttagggct    4140
gttaatttta ttttttctcag tgttctggac actgtagacc tgtgcagtac tcccacaggc    4200
ctgactaacc gccacagatc tctctttctt tctctctggt gacttttttgc ttttgtgata    4260 tggcagcggt gtgacagtcc caggagagaa gtcattaagg gggaacattg caagctatct    4320
tttcgtgttc tcagtgtatt atgtacgtgt gtgctgttgc cgctatgagg gctcggggct    4380
tgcaggctct gagggcatgt cgcaggcgag ctggaaggaa gcgctctcac tttttttcag    4440
gcaatgttgc tagcccttct agcacactga gctacgagac tgccaatctc tctcctgcgg    4500
cacgtttggg ttggcacagc taccatgaaa tgttttaat gggaattcat aaagcaagtt     4560
aggattcaca aatgtagtga cctagtcctt ggagctaaac tgggagtggg tgccaggtgg    4620
agggtagcag gtctgaccag ccctacaccc tgccacagat cacagcttgc cgggcaaatg    4680
accctgcgaa gccacggtgc agcgcccccct gctggcgagc agcgggcaga cctccaagga   4740
cagcctctag ctgaggtctc agtcacatga agtgtgcaca tgaacaggta gaaagcactg    4800
aaaatcgtgt tccaagagca ctttgtaact cactgagggg gaggggaagc accttttggg    4860
```

-continued

```
tttgcgatac caatcaacat aaggtgttgt tgactcgggt acaataaaac tctcaacaca    4920
cacaaagccc atcaggcaag agtacagtaa gcctaagggg acttgctgct caaaccaaaa    4980
attaactctg aaggtcagtc tacctgacat tacctaggca tggtgttgtc caagctgcgc    5040
atcggtgcac agtgtggcct ggcacacacg caggcgggcg acggaacttg aagggttatt    5100
gacatgcaaa tgctggtgtt tgatttcctg tgttgttgcc tcagcgttaa gggcatttcc    5160
gtttgcagtt ctactaaaga cactctgaga aatattccga gtttcgtatt aacctttcct    5220
gtccatgtaa caacttcatg accattactg cattgtcaaa ttcctactga cgacattata    5280
actgtacggg agcttaactt tataaggaaa tgtattttga cactgatatc ttattaaagt    5340
attctgatcc ta                                                        5352
```

<210> SEQ ID NO 2
<211> LENGTH: 25
<212> TYPE: RNA
<213> ORGANISM: Artificial Sequence
<220> FEATURE:
<223> OTHER INFORMATION: Rabbit HIF-2a siRNA sense-oligonucleotide

<400> SEQUENCE: 2
cucaguuaca gccacaucgu cacug                                          25

<210> SEQ ID NO 3
<211> LENGTH: 25
<212> TYPE: RNA
<213> ORGANISM: Artificial Sequence
<220> FEATURE:
<223> OTHER INFORMATION: Rabbit HIF-2a siRNA antisense-oligonucleotide

<400> SEQUENCE: 3
cagugacgau guggcuguaa cugag                                          25

<210> SEQ ID NO 4
<211> LENGTH: 24
<212> TYPE: RNA
<213> ORGANISM: Artificial Sequence
<220> FEATURE:
<223> OTHER INFORMATION: Mouse HIF-2a siRNA sense-oligonucleotide

<400> SEQUENCE: 4
aguuguugua gacuuucacc uggc                                           24

<210> SEQ ID NO 5
<211> LENGTH: 24
<212> TYPE: RNA
<213> ORGANISM: Artificial Sequence
<220> FEATURE:
<223> OTHER INFORMATION: Mouse HIF-2a siRNA antisense-oligonucleotide

<400> SEQUENCE: 5
ggccagguga aagucuacaa caac                                           24

<210> SEQ ID NO 6
<211> LENGTH: 18
<212> TYPE: RNA
<213> ORGANISM: Artificial Sequence
<220> FEATURE:
<223> OTHER INFORMATION: Control siRNA sense-oligonucleotide

<400> SEQUENCE: 6
ccuacgccac caauuucg                                                  18

```
<210> SEQ ID NO 7
<211> LENGTH: 18
<212> TYPE: RNA
<213> ORGANISM: Artificial Sequence
<220> FEATURE:
<223> OTHER INFORMATION: Control siRNA antisense-oligonucleotide

<400> SEQUENCE: 7
acgaaauugg uggcguag                                                     18

<210> SEQ ID NO 8
<211> LENGTH: 22
<212> TYPE: DNA
<213> ORGANISM: Artificial Sequence
<220> FEATURE:
<223> OTHER INFORMATION: sense primer for Human HIF-2a

<400> SEQUENCE: 8
acccagacgg atttcaatga gc                                                22

<210> SEQ ID NO 9
<211> LENGTH: 21
<212> TYPE: DNA
<213> ORGANISM: Artificial Sequence
<220> FEATURE:
<223> OTHER INFORMATION: antisense primer for Human HIF-2a

<400> SEQUENCE: 9
ttgcttccgg catcaaagaa g                                                 21

<210> SEQ ID NO 10
<211> LENGTH: 22
<212> TYPE: DNA
<213> ORGANISM: Artificial Sequence
<220> FEATURE:
<223> OTHER INFORMATION: sense primer for Mouse HIF-2a

<400> SEQUENCE: 10
cgagaagaac gacgtggtgt tc                                                22

<210> SEQ ID NO 11
<211> LENGTH: 19
<212> TYPE: DNA
<213> ORGANISM: Artificial Sequence
<220> FEATURE:
<223> OTHER INFORMATION: antisense primer for Mouse HIF-2a

<400> SEQUENCE: 11
gtgaaggcgg gcaggctcc                                                    19

<210> SEQ ID NO 12
<211> LENGTH: 22
<212> TYPE: DNA
<213> ORGANISM: Artificial Sequence
<220> FEATURE:
<223> OTHER INFORMATION: sense primer for Human MMP1

<400> SEQUENCE: 12
ggaggggatg ctcattttga tg                                                22

<210> SEQ ID NO 13
<211> LENGTH: 21
<212> TYPE: DNA
<213> ORGANISM: Artificial Sequence
<220> FEATURE:
<223> OTHER INFORMATION: antisense primer for Human MMP1

<400> SEQUENCE: 13
```
tagggaagcc aaaggagctg t                                        21

<210> SEQ ID NO 14
<211> LENGTH: 19
<212> TYPE: DNA
<213> ORGANISM: Artificial Sequence
<220> FEATURE:
<223> OTHER INFORMATION: sense primer for Rabbit MMP1

<400> SEQUENCE: 14
atggacctga aggacagct                                           19

<210> SEQ ID NO 15
<211> LENGTH: 19
<212> TYPE: DNA
<213> ORGANISM: Artificial Sequence
<220> FEATURE:
<223> OTHER INFORMATION: antisense primer for Rabbit MMP1

<400> SEQUENCE: 15
cctgcacagt ccagtactt                                           19

<210> SEQ ID NO 16
<211> LENGTH: 23
<212> TYPE: DNA
<213> ORGANISM: Artificial Sequence
<220> FEATURE:
<223> OTHER INFORMATION: sense primer for Human MMP2

<400> SEQUENCE: 16
gcctgagctc ccggaaaaga ttg                                      23

<210> SEQ ID NO 17
<211> LENGTH: 23
<212> TYPE: DNA
<213> ORGANISM: Artificial Sequence
<220> FEATURE:
<223> OTHER INFORMATION: antisense primer for Human MMP2

<400> SEQUENCE: 17
cagcagccta gccagtcgga ttt                                      23

<210> SEQ ID NO 18
<211> LENGTH: 17
<212> TYPE: DNA
<213> ORGANISM: Artificial Sequence
<220> FEATURE:
<223> OTHER INFORMATION: sense primer for Mouse MMP2

<400> SEQUENCE: 18
ccaactacga tgatgac                                             17

<210> SEQ ID NO 19
<211> LENGTH: 17
<212> TYPE: DNA
<213> ORGANISM: Artificial Sequence
<220> FEATURE:
<223> OTHER INFORMATION: antisense primer for Mouse MMP2

<400> SEQUENCE: 19
accagtgtca gtatcag                                             17

<210> SEQ ID NO 20
<211> LENGTH: 21
<212> TYPE: DNA
<213> ORGANISM: Artificial Sequence

```
<220> FEATURE:
<223> OTHER INFORMATION: sense primer for Rabbit MMP2

<400> SEQUENCE: 20
ccgtgtgaag tatggcaatg c                                              21

<210> SEQ ID NO 21
<211> LENGTH: 19
<212> TYPE: DNA
<213> ORGANISM: Artificial Sequence
<220> FEATURE:
<223> OTHER INFORMATION: antisense primer for Rabbit MMP2

<400> SEQUENCE: 21
gcggtcatcg tcgtagttg                                                 19

<210> SEQ ID NO 22
<211> LENGTH: 20
<212> TYPE: DNA
<213> ORGANISM: Artificial Sequence
<220> FEATURE:
<223> OTHER INFORMATION: sense primer for Human MMP3

<400> SEQUENCE: 22
gatgcgcaag cccaggtgtg                                                20

<210> SEQ ID NO 23
<211> LENGTH: 23
<212> TYPE: DNA
<213> ORGANISM: Artificial Sequence
<220> FEATURE:
<223> OTHER INFORMATION: antisense primer for Human MMP3

<400> SEQUENCE: 23
gccaatttca tgagcagcaa cga                                            23

<210> SEQ ID NO 24
<211> LENGTH: 21
<212> TYPE: DNA
<213> ORGANISM: Artificial Sequence
<220> FEATURE:
<223> OTHER INFORMATION: sense primer for Mouse MMP3

<400> SEQUENCE: 24
tcctgatgtt ggtggcttca g                                              21

<210> SEQ ID NO 25
<211> LENGTH: 21
<212> TYPE: DNA
<213> ORGANISM: Artificial Sequence
<220> FEATURE:
<223> OTHER INFORMATION: antisense primer for Mouse MMP3

<400> SEQUENCE: 25
tgtcttggca aatccggtgt a                                              21

<210> SEQ ID NO 26
<211> LENGTH: 19
<212> TYPE: DNA
<213> ORGANISM: Artificial Sequence
<220> FEATURE:
<223> OTHER INFORMATION: sense primer for Rabbit MMP3

<400> SEQUENCE: 26
tgtacccagt ctacaacgc                                                 19
```

```
<210> SEQ ID NO 27
<211> LENGTH: 19
<212> TYPE: DNA
<213> ORGANISM: Artificial Sequence
<220> FEATURE:
<223> OTHER INFORMATION: antisense primer for Rabbit MMP3

<400> SEQUENCE: 27
tccagggact ctctcttct                                                  19

<210> SEQ ID NO 28
<211> LENGTH: 22
<212> TYPE: DNA
<213> ORGANISM: Artificial Sequence
<220> FEATURE:
<223> OTHER INFORMATION: sense primer for Human MMP9

<400> SEQUENCE: 28
ggccaactac gacaccgacg ac                                              22

<210> SEQ ID NO 29
<211> LENGTH: 20
<212> TYPE: DNA
<213> ORGANISM: Artificial Sequence
<220> FEATURE:
<223> OTHER INFORMATION: antisense primer for Human MMP9

<400> SEQUENCE: 29
cgccgccacg aggaacaaac                                                 20

<210> SEQ ID NO 30
<211> LENGTH: 17
<212> TYPE: DNA
<213> ORGANISM: Artificial Sequence
<220> FEATURE:
<223> OTHER INFORMATION: sense primer for Mouse MMP9

<400> SEQUENCE: 30
accacatcga acttcga                                                    17

<210> SEQ ID NO 31
<211> LENGTH: 17
<212> TYPE: DNA
<213> ORGANISM: Artificial Sequence
<220> FEATURE:
<223> OTHER INFORMATION: antisense primer for Mouse MMP9

<400> SEQUENCE: 31
cgaccataca gatactg                                                    17

<210> SEQ ID NO 32
<211> LENGTH: 19
<212> TYPE: DNA
<213> ORGANISM: Artificial Sequence
<220> FEATURE:
<223> OTHER INFORMATION: sense primer for Rabbit MMP9

<400> SEQUENCE: 32
ctcctcgtgc tgggctgtt                                                  19

<210> SEQ ID NO 33
<211> LENGTH: 19
<212> TYPE: DNA
<213> ORGANISM: Artificial Sequence
<220> FEATURE:
<223> OTHER INFORMATION: antisense primer for Rabbit MMP9

<400> SEQUENCE: 33
```

-continued tacacgcggg tgaaggtga                                                19

<210> SEQ ID NO 34
<211> LENGTH: 20
<212> TYPE: DNA
<213> ORGANISM: Artificial Sequence
<220> FEATURE:
<223> OTHER INFORMATION: sense primer for Human MMP12

<400> SEQUENCE: 34
atatgttgac atcaacacat                                               20

<210> SEQ ID NO 35
<211> LENGTH: 20
<212> TYPE: DNA
<213> ORGANISM: Artificial Sequence
<220> FEATURE:
<223> OTHER INFORMATION: antisense primer for Human MMP12

<400> SEQUENCE: 35
ataagcagct tcaatgccag                                               20

<210> SEQ ID NO 36
<211> LENGTH: 20
<212> TYPE: DNA
<213> ORGANISM: Artificial Sequence
<220> FEATURE:
<223> OTHER INFORMATION: sense primer for Mouse MMP12

<400> SEQUENCE: 36
cccagaggtc aagatggatg                                               20

<210> SEQ ID NO 37
<211> LENGTH: 20
<212> TYPE: DNA
<213> ORGANISM: Artificial Sequence
<220> FEATURE:
<223> OTHER INFORMATION: antisense primer for Mouse MMP12

<400> SEQUENCE: 37
ggctccatag agggactgaa                                               20

<210> SEQ ID NO 38
<211> LENGTH: 19
<212> TYPE: DNA
<213> ORGANISM: Artificial Sequence
<220> FEATURE:
<223> OTHER INFORMATION: sense primer for Rabbit MMP12

<400> SEQUENCE: 38
ggagctcatg gagactatg                                                19

<210> SEQ ID NO 39
<211> LENGTH: 16
<212> TYPE: DNA
<213> ORGANISM: Artificial Sequence
<220> FEATURE:
<223> OTHER INFORMATION: antisense primer for Rabbit MMP12

<400> SEQUENCE: 39
ggacactggt tgaact                                                   16

<210> SEQ ID NO 40
<211> LENGTH: 22
<212> TYPE: DNA
<213> ORGANISM: Artificial Sequence

```
<220> FEATURE:
<223> OTHER INFORMATION: sense primer for Human MMP13

<400> SEQUENCE: 40
aggagcatgg cgacttctac cc                                              22

<210> SEQ ID NO 41
<211> LENGTH: 23
<212> TYPE: DNA
<213> ORGANISM: Artificial Sequence
<220> FEATURE:
<223> OTHER INFORMATION: antisense primer for Human MMP13

<400> SEQUENCE: 41
tttgtctggc gttttggat gtt                                              23

<210> SEQ ID NO 42
<211> LENGTH: 23
<212> TYPE: DNA
<213> ORGANISM: Artificial Sequence
<220> FEATURE:
<223> OTHER INFORMATION: sense primer for Mouse MMP13

<400> SEQUENCE: 42
tgatggacct tctggtcttc tgg                                             23

<210> SEQ ID NO 43
<211> LENGTH: 23
<212> TYPE: DNA
<213> ORGANISM: Artificial Sequence
<220> FEATURE:
<223> OTHER INFORMATION: antisense primer for Mouse MMP13

<400> SEQUENCE: 43
catccacatg gttgggaagt tct                                             23

<210> SEQ ID NO 44
<211> LENGTH: 19
<212> TYPE: DNA
<213> ORGANISM: Artificial Sequence
<220> FEATURE:
<223> OTHER INFORMATION: sense primer for Rabbit MMP13

<400> SEQUENCE: 44
cctacaccgg caagagtca                                                  19

<210> SEQ ID NO 45
<211> LENGTH: 19
<212> TYPE: DNA
<213> ORGANISM: Artificial Sequence
<220> FEATURE:
<223> OTHER INFORMATION: antisense primer for Rabbit MMP13

<400> SEQUENCE: 45
tcttgggaat cccagttca                                                  19

<210> SEQ ID NO 46
<211> LENGTH: 20
<212> TYPE: DNA
<213> ORGANISM: Artificial Sequence
<220> FEATURE:
<223> OTHER INFORMATION: sense primer for Human MMP14

<400> SEQUENCE: 46
atgaggcgcc cccgatgtgg                                                 20
```

```
<210> SEQ ID NO 47
<211> LENGTH: 23
<212> TYPE: DNA
<213> ORGANISM: Artificial Sequence
<220> FEATURE:
<223> OTHER INFORMATION: antisense primer for Human MMP14

<400> SEQUENCE: 47
tccaatgttg gggcctggga agt                                            23

<210> SEQ ID NO 48
<211> LENGTH: 20
<212> TYPE: DNA
<213> ORGANISM: Artificial Sequence
<220> FEATURE:
<223> OTHER INFORMATION: sense primer for Mouse MMP14

<400> SEQUENCE: 48
gtgccctagg cctacatccg                                                20

<210> SEQ ID NO 49
<211> LENGTH: 20
<212> TYPE: DNA
<213> ORGANISM: Artificial Sequence
<220> FEATURE:
<223> OTHER INFORMATION: antisense primer for Mouse MMP14

<400> SEQUENCE: 49
ttgggtatcc atccatcact                                                20

<210> SEQ ID NO 50
<211> LENGTH: 19
<212> TYPE: DNA
<213> ORGANISM: Artificial Sequence
<220> FEATURE:
<223> OTHER INFORMATION: sense primer for Rabbit MMP14

<400> SEQUENCE: 50
gcgtacgaga ggaaggatg                                                 19

<210> SEQ ID NO 51
<211> LENGTH: 19
<212> TYPE: DNA
<213> ORGANISM: Artificial Sequence
<220> FEATURE:
<223> OTHER INFORMATION: antisense primer for Rabbit MMP14

<400> SEQUENCE: 51
ccagcaccag gagtagcag                                                 19

<210> SEQ ID NO 52
<211> LENGTH: 23
<212> TYPE: DNA
<213> ORGANISM: Artificial Sequence
<220> FEATURE:
<223> OTHER INFORMATION: sense primer for Human MMP15

<400> SEQUENCE: 52
gcttcgcggg gagatgttcg tgt                                            23

<210> SEQ ID NO 53
<211> LENGTH: 23
<212> TYPE: DNA
<213> ORGANISM: Artificial Sequence
<220> FEATURE:
<223> OTHER INFORMATION: antisense primer for Human MMP15

<400> SEQUENCE: 53
```

```
ctccatccgc aggcgctcat tgt                                              23

<210> SEQ ID NO 54
<211> LENGTH: 22
<212> TYPE: DNA
<213> ORGANISM: Artificial Sequence
<220> FEATURE:
<223> OTHER INFORMATION: sense primer for Mouse MMP15

<400> SEQUENCE: 54
gagagatgtt tgtgttcaag gg                                               22

<210> SEQ ID NO 55
<211> LENGTH: 21
<212> TYPE: DNA
<213> ORGANISM: Artificial Sequence
<220> FEATURE:
<223> OTHER INFORMATION: antisense primer for Mouse MMP15

<400> SEQUENCE: 55
tgtgtcaatg cggtcatagg g                                                21

<210> SEQ ID NO 56
<211> LENGTH: 18
<212> TYPE: DNA
<213> ORGANISM: Artificial Sequence
<220> FEATURE:
<223> OTHER INFORMATION: sense primer for Rabbit MMP15

<400> SEQUENCE: 56
gtactggcgc ttcaacga                                                    18

<210> SEQ ID NO 57
<211> LENGTH: 18
<212> TYPE: DNA
<213> ORGANISM: Artificial Sequence
<220> FEATURE:
<223> OTHER INFORMATION: antisense primer for Rabbit MMP15

<400> SEQUENCE: 57
ccacctcctc catctgca                                                    18

<210> SEQ ID NO 58
<211> LENGTH: 20
<212> TYPE: DNA
<213> ORGANISM: Artificial Sequence
<220> FEATURE:
<223> OTHER INFORMATION: sense primer for Human ADAMTS4

<400> SEQUENCE: 58
agaagaagtt tgacaagtgc                                                  20

<210> SEQ ID NO 59
<211> LENGTH: 19
<212> TYPE: DNA
<213> ORGANISM: Artificial Sequence
<220> FEATURE:
<223> OTHER INFORMATION: antisense primer for Human ADAMTS4

<400> SEQUENCE: 59
gcgtgtattc accattgag                                                   19

<210> SEQ ID NO 60
<211> LENGTH: 22
<212> TYPE: DNA
<213> ORGANISM: Artificial Sequence
```

```
<220> FEATURE:
<223> OTHER INFORMATION: sense primer for Mouse ADAMTS4

<400> SEQUENCE: 60
catccgaaac cctgtcaact tg                                              22

<210> SEQ ID NO 61
<211> LENGTH: 22
<212> TYPE: DNA
<213> ORGANISM: Artificial Sequence
<220> FEATURE:
<223> OTHER INFORMATION: antisense primer for Mouse ADAMTS4

<400> SEQUENCE: 61
gcccatcatc ttccacaata gc                                              22

<210> SEQ ID NO 62
<211> LENGTH: 19
<212> TYPE: DNA
<213> ORGANISM: Artificial Sequence
<220> FEATURE:
<223> OTHER INFORMATION: sense primer for Rabbit ADAMTS4

<400> SEQUENCE: 62
ggattgcacg aggcccgtc                                                  19

<210> SEQ ID NO 63
<211> LENGTH: 19
<212> TYPE: DNA
<213> ORGANISM: Artificial Sequence
<220> FEATURE:
<223> OTHER INFORMATION: antisense primer for Rabbit ADAMTS4

<400> SEQUENCE: 63
cacccggggc tccaatacg                                                  19

<210> SEQ ID NO 64
<211> LENGTH: 17
<212> TYPE: DNA
<213> ORGANISM: Artificial Sequence
<220> FEATURE:
<223> OTHER INFORMATION: sense primer for Human ADAMTS5

<400> SEQUENCE: 64
atcacccaat gccaagg                                                    17

<210> SEQ ID NO 65
<211> LENGTH: 18
<212> TYPE: DNA
<213> ORGANISM: Artificial Sequence
<220> FEATURE:
<223> OTHER INFORMATION: antisense primer for Human ADAMTS5

<400> SEQUENCE: 65
agcagagtag gagacaac                                                   18

<210> SEQ ID NO 66
<211> LENGTH: 22
<212> TYPE: DNA
<213> ORGANISM: Artificial Sequence
<220> FEATURE:
<223> OTHER INFORMATION: sense primer for Mouse ADAMTS5

<400> SEQUENCE: 66
gccattgtaa taccctgca cc                                               22
```

```
<210> SEQ ID NO 67
<211> LENGTH: 22
<212> TYPE: DNA
<213> ORGANISM: Artificial Sequence
<220> FEATURE:
<223> OTHER INFORMATION: antisense primer for Mouse ADAMTS5

<400> SEQUENCE: 67
tcagtcccat ccgtaacctt tg                                              22

<210> SEQ ID NO 68
<211> LENGTH: 21
<212> TYPE: DNA
<213> ORGANISM: Artificial Sequence
<220> FEATURE:
<223> OTHER INFORMATION: sense primer for Rabbit ADAMTS5

<400> SEQUENCE: 68
agggcaagtg tgtggacaag a                                               21

<210> SEQ ID NO 69
<211> LENGTH: 23
<212> TYPE: DNA
<213> ORGANISM: Artificial Sequence
<220> FEATURE:
<223> OTHER INFORMATION: antisense primer for Rabbit ADAMTS5

<400> SEQUENCE: 69
gaaaagattt accttggctg ggc                                             23

<210> SEQ ID NO 70
<211> LENGTH: 22
<212> TYPE: DNA
<213> ORGANISM: Artificial Sequence
<220> FEATURE:
<223> OTHER INFORMATION: sense primer for Human COx-2

<400> SEQUENCE: 70
ttcaaatgag attgtgggaa aa                                              22

<210> SEQ ID NO 71
<211> LENGTH: 20
<212> TYPE: DNA
<213> ORGANISM: Artificial Sequence
<220> FEATURE:
<223> OTHER INFORMATION: antisense primer for Human COx-2

<400> SEQUENCE: 71
agatcatctc tgcctgagct                                                 20

<210> SEQ ID NO 72
<211> LENGTH: 23
<212> TYPE: DNA
<213> ORGANISM: Artificial Sequence
<220> FEATURE:
<223> OTHER INFORMATION: sense primer for Mouse COx-2

<400> SEQUENCE: 72
ggtctggtgc ctggtctgat gat                                             23

<210> SEQ ID NO 73
<211> LENGTH: 22
<212> TYPE: DNA
<213> ORGANISM: Artificial Sequence
<220> FEATURE:
<223> OTHER INFORMATION: antisense primer for Mouse COx-2

<400> SEQUENCE: 73
```

```
gtcctttcaa ggagaatggt gc                                              22

<210> SEQ ID NO 74
<211> LENGTH: 20
<212> TYPE: DNA
<213> ORGANISM: Artificial Sequence
<220> FEATURE:
<223> OTHER INFORMATION: sense primer for Rabbit COx-2

<400> SEQUENCE: 74
tcagccacgc agcaaatcct                                                 20

<210> SEQ ID NO 75
<211> LENGTH: 20
<212> TYPE: DNA
<213> ORGANISM: Artificial Sequence
<220> FEATURE:
<223> OTHER INFORMATION: antisense primer for Rabbit COx-2

<400> SEQUENCE: 75
gtcatctgga tgtcagcacg                                                 20

<210> SEQ ID NO 76
<211> LENGTH: 20
<212> TYPE: DNA
<213> ORGANISM: Artificial Sequence
<220> FEATURE:
<223> OTHER INFORMATION: sense primer for Human iNOS

<400> SEQUENCE: 76
ccatggaaca tcccaaatac                                                 20

<210> SEQ ID NO 77
<211> LENGTH: 21
<212> TYPE: DNA
<213> ORGANISM: Artificial Sequence
<220> FEATURE:
<223> OTHER INFORMATION: antisense primer for Human iNOS

<400> SEQUENCE: 77
tctgcatgta cttcatgaag g                                               21

<210> SEQ ID NO 78
<211> LENGTH: 20
<212> TYPE: DNA
<213> ORGANISM: Artificial Sequence
<220> FEATURE:
<223> OTHER INFORMATION: sense primer for Mouse iNOS

<400> SEQUENCE: 78
tcactgggac agcacagaat                                                 20

<210> SEQ ID NO 79
<211> LENGTH: 20
<212> TYPE: DNA
<213> ORGANISM: Artificial Sequence
<220> FEATURE:
<223> OTHER INFORMATION: antisense primer for Mouse iNOS

<400> SEQUENCE: 79
tgtgtctgca gatgtgctga                                                 20

<210> SEQ ID NO 80
<211> LENGTH: 19
<212> TYPE: DNA
<213> ORGANISM: Artificial Sequence
```

```
<220> FEATURE:
<223> OTHER INFORMATION: sense primer for Rabbit iNOS

<400> SEQUENCE: 80
tcaccatctt ccaggagcg                                                19

<210> SEQ ID NO 81
<211> LENGTH: 19
<212> TYPE: DNA
<213> ORGANISM: Artificial Sequence
<220> FEATURE:
<223> OTHER INFORMATION: antisense primer for Rabbit iNOS

<400> SEQUENCE: 81
cacaatgccg aagtggtcg                                                19

<210> SEQ ID NO 82
<211> LENGTH: 20
<212> TYPE: DNA
<213> ORGANISM: Artificial Sequence
<220> FEATURE:
<223> OTHER INFORMATION: sense primer for Human aggrecan

<400> SEQUENCE: 82
gccttgagca gttcaccttc                                               20

<210> SEQ ID NO 83
<211> LENGTH: 20
<212> TYPE: DNA
<213> ORGANISM: Artificial Sequence
<220> FEATURE:
<223> OTHER INFORMATION: antisense primer for Human aggrecan

<400> SEQUENCE: 83
ctcttctacg gggacagcag                                               20

<210> SEQ ID NO 84
<211> LENGTH: 21
<212> TYPE: DNA
<213> ORGANISM: Artificial Sequence
<220> FEATURE:
<223> OTHER INFORMATION: sense primer for Mouse aggrecan

<400> SEQUENCE: 84
gaagacgaca tcaccatcca g                                             21

<210> SEQ ID NO 85
<211> LENGTH: 22
<212> TYPE: DNA
<213> ORGANISM: Artificial Sequence
<220> FEATURE:
<223> OTHER INFORMATION: antisense primer for Mouse aggrecan

<400> SEQUENCE: 85
ctgtctttgt cacccacaca tg                                            22

<210> SEQ ID NO 86
<211> LENGTH: 19
<212> TYPE: DNA
<213> ORGANISM: Artificial Sequence
<220> FEATURE:
<223> OTHER INFORMATION: sense primer for Rabbit aggrecan

<400> SEQUENCE: 86
caacgtcgcc agagaagtt                                                19
```

```
<210> SEQ ID NO 87
<211> LENGTH: 19
<212> TYPE: DNA
<213> ORGANISM: Artificial Sequence
<220> FEATURE:
<223> OTHER INFORMATION: antisense primer for Rabbit aggrecan

<400> SEQUENCE: 87
cttcgccctc agtgatgtt                                              19

<210> SEQ ID NO 88
<211> LENGTH: 19
<212> TYPE: DNA
<213> ORGANISM: Artificial Sequence
<220> FEATURE:
<223> OTHER INFORMATION: sense primer for Human Coll-II

<400> SEQUENCE: 88
cagttgggag taatgcaag                                              19

<210> SEQ ID NO 89
<211> LENGTH: 18
<212> TYPE: DNA
<213> ORGANISM: Artificial Sequence
<220> FEATURE:
<223> OTHER INFORMATION: antisense primer for Human Coll-II

<400> SEQUENCE: 89
gcctggataa cctctgtg                                               18

<210> SEQ ID NO 90
<211> LENGTH: 22
<212> TYPE: DNA
<213> ORGANISM: Artificial Sequence
<220> FEATURE:
<223> OTHER INFORMATION: sense primer for Mouse Coll-II

<400> SEQUENCE: 90
cacactggta agtggggcaa ga                                          22

<210> SEQ ID NO 91
<211> LENGTH: 23
<212> TYPE: DNA
<213> ORGANISM: Artificial Sequence
<220> FEATURE:
<223> OTHER INFORMATION: antisense primer for Mouse Coll-II

<400> SEQUENCE: 91
ggattgtgtt gtttcagggt tcg                                         23

<210> SEQ ID NO 92
<211> LENGTH: 19
<212> TYPE: DNA
<213> ORGANISM: Artificial Sequence
<220> FEATURE:
<223> OTHER INFORMATION: sense primer for Rabbit Coll-II

<400> SEQUENCE: 92
agccgccatt gatggtctc                                              19

<210> SEQ ID NO 93
<211> LENGTH: 19
<212> TYPE: DNA
<213> ORGANISM: Artificial Sequence
<220> FEATURE:
<223> OTHER INFORMATION: antisense primer for Rabbit Coll-II

<400> SEQUENCE: 93
```
gaccccatgc agtacatgc                                            19

<210> SEQ ID NO 94
<211> LENGTH: 20
<212> TYPE: DNA
<213> ORGANISM: Artificial Sequence
<220> FEATURE:
<223> OTHER INFORMATION: sense primer for Human GAPDH

<400> SEQUENCE: 94
cgtcttcacc accatggaga                                           20

<210> SEQ ID NO 95
<211> LENGTH: 20
<212> TYPE: DNA
<213> ORGANISM: Artificial Sequence
<220> FEATURE:
<223> OTHER INFORMATION: antisense primer for Human GAPDH

<400> SEQUENCE: 95
cggccatcac gccacagttt                                           20

<210> SEQ ID NO 96
<211> LENGTH: 19
<212> TYPE: DNA
<213> ORGANISM: Artificial Sequence
<220> FEATURE:
<223> OTHER INFORMATION: sense primer for Mouse GAPDH

<400> SEQUENCE: 96
tcactgccac ccagaagac                                            19

<210> SEQ ID NO 97
<211> LENGTH: 19
<212> TYPE: DNA
<213> ORGANISM: Artificial Sequence
<220> FEATURE:
<223> OTHER INFORMATION: antisense primer for Mouse GAPDH

<400> SEQUENCE: 97
tgtaggccat gaggtccac                                            19

<210> SEQ ID NO 98
<211> LENGTH: 19
<212> TYPE: DNA
<213> ORGANISM: Artificial Sequence
<220> FEATURE:
<223> OTHER INFORMATION: sense primer for Rabbit GAPDH

<400> SEQUENCE: 98
tcaccatctt ccaggagcg                                            19

<210> SEQ ID NO 99
<211> LENGTH: 19
<212> TYPE: DNA
<213> ORGANISM: Artificial Sequence
<220> FEATURE:
<223> OTHER INFORMATION: antisense primer for Rabbit GAPDH

<400> SEQUENCE: 99
cacaatgccg aagtggtcg                                            19

<210> SEQ ID NO 100
<211> LENGTH: 20
<212> TYPE: DNA
<213> ORGANISM: Artificial Sequence

```
<220> FEATURE:
<223> OTHER INFORMATION: sense primer for Mouse HIF-2a

<400> SEQUENCE: 100
atgacagctg acaaggagaa                                              20

<210> SEQ ID NO 101
<211> LENGTH: 16
<212> TYPE: DNA
<213> ORGANISM: Artificial Sequence
<220> FEATURE:
<223> OTHER INFORMATION: antisense primer for Mouse HIF-2a

<400> SEQUENCE: 101
ggtggcctgg tccaga                                                  16

<210> SEQ ID NO 102
<211> LENGTH: 18
<212> TYPE: DNA
<213> ORGANISM: Artificial Sequence
<220> FEATURE:
<223> OTHER INFORMATION: sense primer for Human HIF-2a

<400> SEQUENCE: 102
atgacagctg acaaggag                                                18

<210> SEQ ID NO 103
<211> LENGTH: 18
<212> TYPE: DNA
<213> ORGANISM: Artificial Sequence
<220> FEATURE:
<223> OTHER INFORMATION: antisense primer for Human HIF-2a

<400> SEQUENCE: 103
agggctattg ggcgtgga                                                18

<210> SEQ ID NO 104
<211> LENGTH: 23
<212> TYPE: DNA
<213> ORGANISM: Artificial Sequence
<220> FEATURE:
<223> OTHER INFORMATION: sense primer for Human MMP1

<400> SEQUENCE: 104
ggagtcactt cagtggcaag tgt                                          23

<210> SEQ ID NO 105
<211> LENGTH: 23
<212> TYPE: DNA
<213> ORGANISM: Artificial Sequence
<220> FEATURE:
<223> OTHER INFORMATION: antisense primer for Human MMP1

<400> SEQUENCE: 105
actggccttt gtcttctttc tca                                          23

<210> SEQ ID NO 106
<211> LENGTH: 18
<212> TYPE: DNA
<213> ORGANISM: Artificial Sequence
<220> FEATURE:
<223> OTHER INFORMATION: sense primer for Mouse MMP2

<400> SEQUENCE: 106
cgcctcataa gttgtcca                                                18
```

```
<210> SEQ ID NO 107
<211> LENGTH: 18
<212> TYPE: DNA
<213> ORGANISM: Artificial Sequence
<220> FEATURE:
<223> OTHER INFORMATION: antisense primer for Mouse MMP2

<400> SEQUENCE: 107
cgttgcgctc ccgggctc                                                 18

<210> SEQ ID NO 108
<211> LENGTH: 21
<212> TYPE: DNA
<213> ORGANISM: Artificial Sequence
<220> FEATURE:
<223> OTHER INFORMATION: sense primer for Human MMP3

<400> SEQUENCE: 108
ctgtttgaca tttgctatga g                                             21

<210> SEQ ID NO 109
<211> LENGTH: 21
<212> TYPE: DNA
<213> ORGANISM: Artificial Sequence
<220> FEATURE:
<223> OTHER INFORMATION: antisense primer for Human MMP3

<400> SEQUENCE: 109
ccttgctgtc ttgcctgcct c                                             21

<210> SEQ ID NO 110
<211> LENGTH: 22
<212> TYPE: DNA
<213> ORGANISM: Artificial Sequence
<220> FEATURE:
<223> OTHER INFORMATION: sense primer for Mouse MMP9

<400> SEQUENCE: 110
gagagttttg tagagagcgt at                                            22

<210> SEQ ID NO 111
<211> LENGTH: 21
<212> TYPE: DNA
<213> ORGANISM: Artificial Sequence
<220> FEATURE:
<223> OTHER INFORMATION: antisense primer for Mouse MMP9

<400> SEQUENCE: 111
ggtgaggacc gcagcttctg g                                             21

<210> SEQ ID NO 112
<211> LENGTH: 16
<212> TYPE: DNA
<213> ORGANISM: Artificial Sequence
<220> FEATURE:
<223> OTHER INFORMATION: sense primer for Human MMP12

<400> SEQUENCE: 112
ggagtagcct gtaatc                                                   16

<210> SEQ ID NO 113
<211> LENGTH: 18
<212> TYPE: DNA
<213> ORGANISM: Artificial Sequence
<220> FEATURE:
<223> OTHER INFORMATION: antisense primer for Human MMP12

<400> SEQUENCE: 113
```

```
taaacttcta aacggatc                                                 18

<210> SEQ ID NO 114
<211> LENGTH: 23
<212> TYPE: DNA
<213> ORGANISM: Artificial Sequence
<220> FEATURE:
<223> OTHER INFORMATION: sense primer for Human MMP13

<400> SEQUENCE: 114
cacggtactg aatgtgtgat gtc                                           23

<210> SEQ ID NO 115
<211> LENGTH: 23
<212> TYPE: DNA
<213> ORGANISM: Artificial Sequence
<220> FEATURE:
<223> OTHER INFORMATION: antisense primer for Human MMP13

<400> SEQUENCE: 115
cttgaatggt gatgcctggg gac                                           23

<210> SEQ ID NO 116
<211> LENGTH: 18
<212> TYPE: DNA
<213> ORGANISM: Artificial Sequence
<220> FEATURE:
<223> OTHER INFORMATION: sense primer for Human MMP14

<400> SEQUENCE: 116 tttttttggca agcatctg                                                18

<210> SEQ ID NO 117
<211> LENGTH: 18
<212> TYPE: DNA
<213> ORGANISM: Artificial Sequence
<220> FEATURE:
<223> OTHER INFORMATION: antisense primer for Human MMP14

<400> SEQUENCE: 117
ggtccgagac caccgggt                                                 18

<210> SEQ ID NO 118
<211> LENGTH: 23
<212> TYPE: DNA
<213> ORGANISM: Artificial Sequence
<220> FEATURE:
<223> OTHER INFORMATION: sense primer for Human MMP15

<400> SEQUENCE: 118
ccaaactttt taaaattggc taa                                           23

<210> SEQ ID NO 119
<211> LENGTH: 22
<212> TYPE: DNA
<213> ORGANISM: Artificial Sequence
<220> FEATURE:
<223> OTHER INFORMATION: antisense primer for Human MMP15

<400> SEQUENCE: 119
tcttaaaggg ccagtgtgct cc                                            22

<210> SEQ ID NO 120
<211> LENGTH: 21
<212> TYPE: DNA
<213> ORGANISM: Artificial Sequence
```

```
<220> FEATURE:
<223> OTHER INFORMATION: sense primer for Mouse ADAMTS4

<400> SEQUENCE: 120
tgtgccttct ccttctgcca g                                            21

<210> SEQ ID NO 121
<211> LENGTH: 21
<212> TYPE: DNA
<213> ORGANISM: Artificial Sequence
<220> FEATURE:
<223> OTHER INFORMATION: antisense primer for Mouse ADAMTS4

<400> SEQUENCE: 121
ctgcggcacc aaaatgctcc a                                            21

<210> SEQ ID NO 122
<211> LENGTH: 21
<212> TYPE: DNA
<213> ORGANISM: Artificial Sequence
<220> FEATURE:
<223> OTHER INFORMATION: sense primer for Mouse ADAMTS5

<400> SEQUENCE: 122
tttgaaaatg agagggctga c                                            21

<210> SEQ ID NO 123
<211> LENGTH: 21
<212> TYPE: DNA
<213> ORGANISM: Artificial Sequence
<220> FEATURE:
<223> OTHER INFORMATION: antisense primer for Mouse ADAMTS5

<400> SEQUENCE: 123
agtgcgctgc ccgccgggag g                                            21

<210> SEQ ID NO 124
<211> LENGTH: 23
<212> TYPE: DNA
<213> ORGANISM: Artificial Sequence
<220> FEATURE:
<223> OTHER INFORMATION: sense primer for Mouse COX-2

<400> SEQUENCE: 124
gtgtatagct ggctgtcctg aaa                                          23

<210> SEQ ID NO 125
<211> LENGTH: 17
<212> TYPE: DNA
<213> ORGANISM: Artificial Sequence
<220> FEATURE:
<223> OTHER INFORMATION: antisense primer for Mouse COX-2

<400> SEQUENCE: 125
cgcagaggtg gcagcgg                                                 17

<210> SEQ ID NO 126
<211> LENGTH: 18
<212> TYPE: DNA
<213> ORGANISM: Artificial Sequence
<220> FEATURE:
<223> OTHER INFORMATION: sense primer for Mouse iNOS

<400> SEQUENCE: 126
atggaaagtt atagtctc                                                18
```

<210> SEQ ID NO 127
<211> LENGTH: 17
<212> TYPE: DNA
<213> ORGANISM: Artificial Sequence
<220> FEATURE:
<223> OTHER INFORMATION: antisense primer for Mouse iNOS

<400> SEQUENCE: 127
caagactcac cttgcag                                                17

<210> SEQ ID NO 128
<211> LENGTH: 30
<212> TYPE: DNA
<213> ORGANISM: Artificial Sequence
<220> FEATURE:
<223> OTHER INFORMATION: double strand oligonucleotide sequences of MMP1
      promoter

<400> SEQUENCE: 128
aggatttcct tttcgtgaga atgtcttccc                                   30

<210> SEQ ID NO 129
<211> LENGTH: 30
<212> TYPE: DNA
<213> ORGANISM: Artificial Sequence
<220> FEATURE:
<223> OTHER INFORMATION: double strand oligonucleotide variant of MMP1
      promoter

<400> SEQUENCE: 129
aggatttcct tttaaagaga atgtcttccc                                   30

<210> SEQ ID NO 130
<211> LENGTH: 30
<212> TYPE: DNA
<213> ORGANISM: Artificial Sequence
<220> FEATURE:
<223> OTHER INFORMATION: double strand oligonucleotide of MMP3 promoter

<400> SEQUENCE: 130
ttaggccagg tgccgtgacc catgtctgta                                   30

<210> SEQ ID NO 131
<211> LENGTH: 30
<212> TYPE: DNA
<213> ORGANISM: Artificial Sequence
<220> FEATURE:
<223> OTHER INFORMATION: double strand oligonucleotide variant of MMP3
      promoter

<400> SEQUENCE: 131
ttaggccagg tgcaaagacc catgtctgta                                   30

<210> SEQ ID NO 132
<211> LENGTH: 31
<212> TYPE: DNA
<213> ORGANISM: Artificial Sequence
<220> FEATURE:
<223> OTHER INFORMATION: double strand oligonucleotide of MMP9 promoter

<400> SEQUENCE: 132
tcaactgaag gtctcgtgaa cactgctgaa a                                 31

<210> SEQ ID NO 133
<211> LENGTH: 31
<212> TYPE: DNA
<213> ORGANISM: Artificial Sequence
<220> FEATURE:

<223> OTHER INFORMATION: double strand oligonucleotide varinat of MMP9
      promoter

<400> SEQUENCE: 133
tcaactgaag gtctaaagaa cactgctgaa a                                   31

<210> SEQ ID NO 134
<211> LENGTH: 30
<212> TYPE: DNA
<213> ORGANISM: Artificial Sequence
<220> FEATURE:
<223> OTHER INFORMATION: double strand oligonucleotide of MMP12 promoter

<400> SEQUENCE: 134
taacacactc ttaggtgcac cctaccgcac                                     30

<210> SEQ ID NO 135
<211> LENGTH: 30
<212> TYPE: DNA
<213> ORGANISM: Artificial Sequence
<220> FEATURE:
<223> OTHER INFORMATION: double strand oligonucleotide variant of MMP12
      promoter

<400> SEQUENCE: 135
taacacactc ttaaaagcac cctaccgcac                                     30

<210> SEQ ID NO 136
<211> LENGTH: 30
<212> TYPE: DNA
<213> ORGANISM: Artificial Sequence
<220> FEATURE:
<223> OTHER INFORMATION: double strand oligonucleotide of MMP13 promoter

<400> SEQUENCE: 136
tttggtccaa tatcgtgaac ttcaggtaga                                     30

<210> SEQ ID NO 137
<211> LENGTH: 30
<212> TYPE: DNA
<213> ORGANISM: Artificial Sequence
<220> FEATURE:
<223> OTHER INFORMATION: double strand oligonucleotide variant of MMP13
      promoter

<400> SEQUENCE: 137
tttggtccaa tataaagaac ttcaggtaga                                     30

<210> SEQ ID NO 138
<211> LENGTH: 32
<212> TYPE: DNA
<213> ORGANISM: Artificial Sequence
<220> FEATURE:
<223> OTHER INFORMATION: double strand oligonucleotide of Ptgs2 promoter

<400> SEQUENCE: 138
tcgtcttctc atttgcgtgg gtaaagcctg cc                                  32

<210> SEQ ID NO 139
<211> LENGTH: 32
<212> TYPE: DNA
<213> ORGANISM: Artificial Sequence
<220> FEATURE:
<223> OTHER INFORMATION: double strand oligonucleotide variant of Ptgs2
      promoter

<400> SEQUENCE: 139

```
tcgtcttctc atttgaaagg gtaaagcctg cc                                    32

<210> SEQ ID NO 140
<211> LENGTH: 32
<212> TYPE: DNA
<213> ORGANISM: Artificial Sequence
<220> FEATURE:
<223> OTHER INFORMATION: double strand oligonucleotide of Nos2 promoter

<400> SEQUENCE: 140
ttttgaagtg actacgtgct gcctaggggc ca                                    32

<210> SEQ ID NO 141
<211> LENGTH: 32
<212> TYPE: DNA
<213> ORGANISM: Artificial Sequence
<220> FEATURE:
<223> OTHER INFORMATION: double strand oligonucleotide varinat of Nos2
      promoter

<400> SEQUENCE: 141
ttttgaagtg actaaaagct gcctaggggc ca                                    32

<210> SEQ ID NO 142
<211> LENGTH: 33
<212> TYPE: DNA
<213> ORGANISM: Artificial Sequence
<220> FEATURE:
<223> OTHER INFORMATION: double strand oligonucleotide of Adamts4
      promoter

<400> SEQUENCE: 142
ggagcagaaa gaacccgtgg gcacttttcc tga                                   33

<210> SEQ ID NO 143
<211> LENGTH: 33
<212> TYPE: DNA
<213> ORGANISM: Artificial Sequence
<220> FEATURE:
<223> OTHER INFORMATION: double strand oligonucleotide varinat of
      Adamts4 promoter

<400> SEQUENCE: 143
ggagcagaaa gaaccaaagg gcacttttcc tga                                   33
```

PHARMACEUTICAL COMPOSITION INCLUDING AN HIF-2 ALPHA INHIBITOR AS AN ACTIVE INGREDIENT FOR PREVENTING OR TREATING ARTHRITIS

This is a National Phase Application filed under 35 U.S.C. §371 as a national stage of International Application No. PCT/KR2010/005889, filed Aug. 31, 2010, claiming the benefit from Korean Patent Application No. 10-2010-0047485, filed May 20, 2010, the entire content of each of which is hereby incorporated by reference in its entirety.

The Sequence Listing submitted in text format (.txt) filed on May 29, 2013, named, "Revised_PP100057US_SequenceList.txt," (created on May 29, 2013), is incorporated herein by reference.

FIELD OF THE INVENTION

The present invention relates to a pharmaceutical composition including an HIF-2α inhibitor as an active ingredient for preventing or treating arthritis.

DESCRIPTION OF THE RELATED ART

Degenerative arthritis (osteoarthritis, OA) is a representative degenerative disease that is primarily characterized by gradual and irreversible articular cartilage destruction and it leads to degrade the quality of life. Peoples aged more than 70 years old represent a degenerative arthritis and approximately ¼ of them require clinical treatment. Once damaged, cartilage tissues do not normally regenerate in vivo.

When articular cartilage tissues are damaged, daily activities are limited with severe pain and chronic damages induce degenerative arthritis to interfere normal life or professional activities. The market size of arthritis continues to increase is approximately 9.5 billion dollars in the world, growing by an annual average 14% and expected to approximately 20 billion dollars in 2005 and approximately 350 billion dollars in 2010. Currently, it now has an estimated 400 billion won in domestic market. However, no effective medical therapy to prevent OA cartilage destruction is currently available, owing to the limited understanding of the underlying molecular pathogenic mechanisms.

Although biological and medical cell therapy researches, tissue engineering methods or gene therapies for degenerative arthritis have been tried experimentally, clinical application is difficult. Specifically, treatments of damaged cartilage have been developed so far including chondroplasty, osteochondral transplantation and autolaugous chondrocyte transplantation. The chondroplasty is the most commonly used method. It is no need to direct arthrotomy so that suffering and the burden of patients reduce fine tissue damages can be treated immediately through an arthroscope. However, the effects are not satisfactory in functional aspect, because fibro-cartilages are mainly generated, not hyaline cartilage which is required for the actual joints, in chondroplasty. On the other hand, the osteochondral transplantation is a method that cartilage and subchondral bone already generated are collected from normal portion of patient, transplanted to the appropriate hole in damaged cartilage to generate hyaline cartilage. It is successful to some patients. However, this method is not a complete treatment because it has problems that a gap between transplanted portion and original tissue remains and only patients available to autolaugous transplantation can be performed. The autolaugous chondrocyte transplantation recently started implementing is a method that chondrocytes collected from cartilage tissues of normal portion of patient are cultured, proliferated as required in vitro, used for having space using periosteum and injected with media to fill damaged cartilage portion by these proliferated cells. However, the procedure of the autolaugous chondrocyte transplantation is intricate and strict because the donor tissue is limited and it is necessary surgery for transplant tissue.

Pathological causes of degenerative arthritis have been known to be induced by biochemical changes in the articular cartilage which is caused by the mechanical damage of the joints, genetic factors and obesity. This in turn leads to activation of biochemical pathways in chondrocytes, a unique resident cell type that synthesizes cartilagespecific extracellular matrix (ECM) components as well as various catabolic and anabolic factors. Activation of biochemical pathways involves the production of proinflammatory cytokines, inflammation, degradation of the ECM by matrix metalloproteinases (MMPs) and ADAMTS, and cessation of ECM synthesis via dedifferentiation and apoptosis of chondrocytes. MMP and ADAMTS generated from chondrocytes degrade various ECM (extracellular matrix) molecules which are synthesized and secreted from chondrocytes, i.e., collagen, proteoglycan, and consequently alter cartilage tissue destruction and the molecular composition of cartilage tissue ECM. Therefore, synthesis and activity regulation for MMP and ADAMTS become an important target in the control of cartilage degeneration. However, the molecular regulation mechanisms of them need to be elucidated in more detail. The MMP expression regulation mechanism in chondrocytes is unclear yet, it is generated by inflammatory cytokines such as interleukin (IL)-1β and TNF-α. In addition, the inflammatory cytokines induce the production of nitric oxide (NO) to increase the synthesis of MMP and ADAMTS. For example, MMP generated in chondrocytes include MMP-1, -2, -3, -9, -12, -13, -14 and -15, ADAMTS generated in chondrocytes include ADAMTS-4 and -5.

Meanwhile, the HIF-2α (also known as endothelial PAS domain protein-1 or EPAS1) is gene regulated via hypoxea as transcription factor and it induces expression of target genes to allow adopting hypoxea. HIF-2α is also known that it is involved to fat deposition in the liver and adipocytes. However, function of HIF-2α in cartilage degeneration is not yet clearly understood, except for a report that HIF-2α is expressed in hypertrophic chondrocyte (Tian, H., et al., Genes Dev. 12, 3320-3324, 1998; Stewart, A. J. et al., J. Cell. Physiol. 206, 435-440, 2006). According to the reports reported so far, HIF is known that it has 3 subtypes, HIF-1α, HIF-2α and HIF-3α, and each of them as a dimer consisting of α subunit and the β subunit combines with DNA. HIF-2α is a homologue of HIF-1α and forms a dimer with HIF-1β in hypoxia condition. However, as a result of HIF-2α knockout mouse experiment, HIF-2α is involved to specific physiological phenomena such as hematogenesis or catecholamin homeostasis in normoxia.

Throughout this application, several patents and publications are referenced and citations are provided in parentheses. The disclosure of these patents and publications is incorporated into this application in order to more fully describe this invention and the state of the art to which this invention pertains.

DETAILED DESCRIPTION OF THIS INVENTION

Technical Purposes of this Invention

The present inventors have made intensive studies to develop novel biomolecules for preventing or treating arthritis efficiently. As a result, they found out that HIF-2α increases the expression thereof in chondrocytes or tissue in which osteoarthritis is induced, and triggers the expression of various cartilage degeneration factors and the activation of mitogen-activated protein (MAP) kinase. Therefore, arthritis may be prevented or treated through the inhibitory thereof in animal cells or tissues.

Accordingly, it is an object of this invention to provide a pharmaceutical composition for preventing or treating arthritis.

It is another object of this invention to provide a composition for diagnosing arthritis or analyzing a prognosis of arthritis.

It is still another object of this invention to provide a method for diagnosing arthritis or detecting a prognosis analysis marker of arthritis.

It is further object of this invention to provide a method for screening a therapeutic agent for treating arthritis.

It is still further object of this invention to provide a gene delivery system for inducing arthritis.

Other objects and advantages of the present invention will become apparent from the detailed description to follow taken in conjugation with the appended claims and drawings.

DETAILED DESCRIPTION OF THIS INVENTION

In one aspect of the present invention, there is provided a pharmaceutical composition for preventing or treating arthritis, comprising as an active ingredient a substance inhibiting the expression of the hypoxia-inducible factor-2α (HIF-2α) gene or the activity of the HIF-2α protein.

In another aspect of the present invention, there is provided a composition for diagnosing arthritis or analyzing a prognosis of arthritis, comprising a HIF-2α protein-specific binding agent, a nucleotide sequence encoding the HIF-2α protein, a complementary nucleotide sequence to the nucleotide sequence or a fragment of the nucleotide sequence.

In still another aspect of the present invention, there is provided a method for diagnosing arthritis or detecting a prognosis analysis marker of arthritis to provide information required for diagnosing arthritis or detecting a prognosis analysis marker through methods for detecting the expression of a HIF-2α protein or a nucleotide sequence coding HIF-2α protein in human biological sample.

In further aspect of the present invention, there is provided a method for screening a therapeutic agent for treating arthritis, comprising:

(a) contacting a test substance of interest for analysis to cells comprising a nucleotide sequence encoding the HIF-2α protein; and (b) analyzing the expression level of the HIF-2α protein, wherein where the test substance inhibits the expression of the HIF-2α protein, it is determined as the therapeutic agent for treating arthritis.

In still further aspect of the present invention, there is provided a method for screening a therapeutic agent for treating arthritis, comprising:

(a) contacting a test substance of interest for analysis to the HIF-2α protein and a transcription-regulating sequence binding to the HIF-2α protein; and (b) analyzing the binding affinity of the transcription-regulating sequence to the HIF-2α protein, wherein where the test substance inhibits the binding of the transcription-regulating sequence to the HIF-2α, it is determined as the therapeutic agent for treating arthritis.

In further aspect of the present invention, there is provided a gene delivery system for inducing arthritis comprising a nucleotide sequence of interest for delivery into cells; wherein the nucleotide sequence is a nucleotide sequence encoding the HIF-2α protein.

In still further aspect of the present invention, there is provided a method for preventing or treating arthritis, comprising administering a substance inhibiting the expression of the hypoxia-inducible factor-2α (HIF-2α) gene or the activity of the HIF-2α protein.

In further aspect of the present invention, there is provided a method for inducing arthritis, comprising contacting to cells a gene delivery system comprising a nucleotide sequence encoding the HIF-2α protein.

The present inventors have made intensive studies to develop novel biomolecules for preventing or treating arthritis efficiently. As a result, they found out that HIF-2α increases the expression thereof in chondrocytes or tissue in which osteoarthritis is induced, and triggers the expression of various cartilage degeneration factors and the activation of mitogen-activated protein (MAP) kinase. Therefore, arthritis may be prevented or treated through the inhibitory thereof in animal cells or tissues.

Arthritis means diseases of joint disorder that involves inflammation caused by various factors. Specially, osteoarthritis (OA) is one of the oldest and the most common disease. It means a chronic state characterized by destruction of joint's cartilage and is known as degenerative joint disease, ostoarthrosis, hypertrophic arthritis or degenerative arthritis. Therefore, the term used herein "osteoarthritis" and other names above-mentioned will be used interchangeably. Cartilage is one area of the joint that it serves as cushion at tail end of bones to support moving joint easily. Cartilage destruction induces an abrasion between the adjacent bones and lead to stiffness and suffering caused by difficulty of the movement of the joints.

Arthritis is very high incidence disease which is estimated approximately 200 million people in Korea and approximately 2,700 million in the United States (Helmick, C., et al of the Prevalence of Arthritis and Other Rheumatic conditions. Arthritis & Rheumatism, 58 (1): 15-25 (2008)). Unfortunately, a clear understanding for cause of the disease is scarce yet so that there is no therapeutic method. Actually, therapeutic method can be a variety of ways depending on the situation, because arthritis is caused by various factors (for example, age, obesity, injury, excessive use of joint and genetic cause).

The present invention identifies the activity and the mechanism of HIF-2α as osteoarthritis-inducing factor and its controllable target factor, and first proposes that arthritis may be prevented or treated using it.

According to a preferred embodiment, the HIF-2α of the present invention is increased the expression of mRNA level or protein level in cells or tissues of arthritis induced, more preferably cells or tissues of arthritis induced by inflammatory (pro-inflammatory) cytokines or mechanical defects. On the contrary, the HIF-2α of the present invention was not detected changes of the expression levels by anti-inflammatory (for example, IL-4, IL-10 or IL-12) (see: FIG. 2).

According to a preferred embodiment, the available inflammatory cytokine in the present invention includes interleukin (IL)-1α, IL-1β, IL-6, IL-8, IL-17, IL-21, TNF (tumor necrosis factor)-α, INF (interferon)-γ, HMG1, PAF (olatelet-activating factor) or MIF (magrophage migration inhibitory factor), more preferably IL-1β, IL-17, IL-21 or TNF-α, most preferably IL-1β or IL-17.

According to a preferred embodiment, the mechanical defects used in the present invention perform through collagenase injection to cells (for example, chondrocytes) or cruciate ligament destabilization of the medial meniscus (DMM) to tissue (for example, cartilage tissue)

According to a preferred embodiment, the HIF-2α of the present invention increases the expression of cartilage degeneration-inducing factor in mRNA level or protein level.

According to a preferred embodiment, the cartilage degeneration-inducing factor of the present invention includes, but not limited to, matrix metalloprotenase (MMP)-1, MMP-3, MMP-9, MMP-12, MMP-13, ADAMTS (a disintegrin and metalloproteinase with thrombospondin motifs)-4, ADAMTS-5, PTGS-2 (Prostaglandin-endoperoxide synthase-2) or NOS2 (nitric oxide synthase 2).

According to a preferred embodiment, the HIF-2α of the present invention phosphorylates a MAP (mitogen-activated protein) kinase to activate signal transduction pathway. According to a more preferred embodiment, the MAP (mitogen-activated protein) kinase includes, but not limited to, ERK (extarcellular-signal regulated kinase), JNK (c-Jun N terminal kinase) or p38 MAP kinase.

According to a preferred embodiment, the composition of the present invention may include siRNA (small interference RNA), shRNA (short hairpin RNA), miRNA (microRNA), ribozyme, DNAzyme, PNA (peptide nucleic acids), antisense oligonucleotides, peptides, antibodies, aptamers, extracts of natural sources and chemical substances. More preferably, the composition of the present invention may include a nucleotide sequence coding HIF-2α protein, a sequence complementary to the nucleotide sequence, or siRNA, shRNA, miRNA, ribozyme, DNAzyme or antisense oligonucleotides for a fragment of the nucleotide sequence as an active ingredient.

The pharmaceutical composition of the present invention comprises siRNA having sequence complementary to the nucleotide sequence as set forth in SEQ ID NO:1.

The term used herein "siRNA" refers to a short double strand RNA that enables to mediate RNA interference via cleavage of mRNA (see: WO 00/44895, WO 01/36646, WO 99/32619, WO 01/29058, WO 99/07409 and WO 00/44914). The siRNA of the present invention may consist of a sense RNA strand having a sequence corresponding to a target gene and an antisense RNA strand having a sequence complementary to the target gene. The siRNA to inhibit expression of a target gene provides effective gene knock-down method or gene therapy method. Recently siRNA was applied to the study of mammalian cells (Degot S, et al. 2002; Degot S, et al. 2004; Ballut L, et al. 2005).

The siRNA molecule of the present invention may has double strand structure that the sense strand (sequence corresponding to HIF-2α mRNA sequence) and the antisense strand (sequence corresponding to HIF-2α mRNA sequence) are located on the opposite side each other to form. In additin, according to another embodiment, the siRNA molecule of the present invention may has single strand structure in which has self-complementary sense strand and antisense strand. The siRNA of this invention is not restricted to a RNA duplex of which two strands are completely paired and may comprise non-paired portion such as mismatched portion with non-complementary bases and bulge with no opposite bases. The overall length of the siRNA is 10-100 nucleotides, preferably 15-80 nucleotides, more preferably, 20-70 nucleotides and most preferably 20-30 nucleotides. The siRNA may comprise either blunt or cohesive end so long as it enables to inhibit the target gene expression via RNAi effect. The cohesive end may be prepared in 3'-end overhanging structure or 5'-end overhanging structure.

The siRNA molecule of the present invention may include the form that short nucleotide sequences (approximately 5-15 nt) is inserted between self-complementary sense and antisense strands. In this case, the siRNA molecule formed by the expression of the nucleotide sequence is formed hairpin structure by intramolecular hybridization, and overall stem-and-loop structure. The stem-and-loop structure is processed in vivo or in vitro to produce siRNA molecule of activity which may mediate RNAi.

According to a preferred embodiment, the siRNA of the present invention has nucleotide sequence included the nucleotide sequence as set forth in SEQ ID NO:1. According to the present invention, as HIF-2α-siRNA was treated, the expression level of cartilage degeneration-inducing factor induced by cytokine was markedly decreased with concentration-dependently in chondrocytes trated with cytokine (for example, mouse knee articular chondrocytes). In addition, the MAP kinase phosphorylation was significantly reduced (see: FIGS. 3 and 4).

The pharmaceutical composition of the present disclosure may comprise a pharmaceutically acceptable carrier. The pharmaceutically acceptable carrier included in the pharmaceutical composition of the present disclosure is one commonly used in the preparation of formulations and includes lactose, dextrose, sucrose, sorbitol, mannitol, starch, gum acacia, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil, etc., but is not limited thereto. The pharmaceutical composition of the present disclosure may further include, in addition to the above-described components, a lubricant, a wetting agent, a sweetener, a fragrance, an emulsifier, a suspending agent, a preservative, or the like. Suitable pharmaceutically acceptable carriers and formulations are described in detail in *Remington's Pharmaceutical Sciences* (19th ed., 1995).

The composition of the present invention may be administered orally or parenterally. Preferably, it may be administered parenterally. When the composition of the present disclosure is administered parenterally, the pharmaceutical composition of the present disclosure may administer with intravenous injection, subcutaneous injection, local injection and intramuscular injection.

An appropriate administration dosage of the pharmaceutical composition of the present disclosure may be determined variously depending on such factors as preparation method, administration method, age, body weight and gender of a patient, pathological condition, diet, administration time, administration route, excretion rate or response sensitivity. Specifically, a daily dosage of the pharmaceutical composition of the present disclosure may be 0.0001-100 mg/kg (weight).

The pharmaceutical composition of the present disclosure may be prepared into a unit dosage form or multiple dosage form along with a pharmaceutically acceptable carrier and/or excipient according to a method that can be easily employed by those skilled in the art. The formulation may be in the form of solution in oily or aqueous medium, suspension, syrup, emulsion, extract, dust, powder, granule, tablet or capsule, and may further include a dispersant or stabilizer.

The term used herein "biological sample" refers to all the samples obtained from human or mammals, for example, cartilage (articular cartilage) cells or tissues, urine, saliva, blood, plasma, or serum samples, but are not limited to, urine, whole blood, plasma and sera.

According to a preferred embodiment, the HIF-2α of the present invention
is included in cartilage, especially, articular cartilage sample. Therefore, the HIF-2α of the present invention may be an indicator for the occurrence and development of arthritis and used for the occurrence and development of arthritis.

According to a preferred embodiment, the composition of the present invention is used for predicting or diagnosing of osteoarthritis, degenerative joint disease, osteochondritis dissecans, ligament injuries, meniscus injuries, malalignment of joint, osteonecrosis, rheumatoid arthritis, juvenile idiopathic arthritis, trauma, inflammatory arthritis or septic arthritis caused by infection, more preferably for predicting or diagnosing of osteoarthritis or degenerative joint disease, most preferably for predicting or diagnosing of osteoarthritis with great accuracy.

The term used herein "diagnosis" includes the following matters: (a) to determine susceptibility of a subject to a particular disease or disorder; (b) to evaluate whether a subject has a particular disease or disorder; (c) to assess a prognosis of a subject suffering from a specific disease or disorder (e.g., identification of pre-metastatic or metastatic cancer conditions, determination of cancer stage, or investigation of cancer response to treatment); or (d) therametrics (e.g., monitoring conditions of a subject to provide an information to treatment efficacy).

The term as used herein "diagnosis", refers to the identification of the presence or properties of colorectal cancer conditions. With respect to the objects of the present invention, the diagnosis indicates the identification of the incidence of colorectal cancer by detecting the expression of a diagnostic marker for colorectal cancer.

The term as used herein "prognosis" includes prediction in terms of the progression possibility process of the disease, in particular, the improvement of the disease, the regeneration of the disease and arthritis recurrence. Preferably, the prognosis of the present invention refers to completely cured possibility for the disease of arthritis patients.

According to a preferred embodiment, the present invention may be performed to the manner of immunoassay, i.e., antigen-antibody reaction manner. At this time, it is performed using an antibody or an aptamer specific binding to arthritis marker (e.g., HIF-2α) of the present invention mentioned-above.

The antibody used in the present invention is polyclonal or monoclonal antibody, preferably monoclonal antibody. Antibody production may be prepared by a method widely known in the art, such as a hybridoma method (Kohler and Milstein, European Journal of Immunology, 6:511-519 (1976)), a recombinant DNA methods (U.S. Pat. No. 4,816,56) or a phage antibody library technique (Clackson et al, Nature, 352:624-628 (1991) and Marks et al, J. Mol. Biol., 222:58, 1-597 (1991)). General process for antibody production is described in Harlow, E. and Lane, D., Using Antibodies: A Laboratory Manual, Cold Spring Harbor Press, New York, 1999; Zola, H., Monoclonal Antibodies: A Manual of Techniques, CRC Press, Inc., Boca Raton, Fla., 1984; Coligan, CURRENT PROTOCOLS IN IMMUNOLOGY, Wiley/Greene, NY, 1991, and the literatures are inserted as reference in the present invention. For example, the preparation of the hybridoma cells producing monoclonal antibody is accomplished by fusing immortalized cell line with antibody-producing lymphocytes. The technology required for this process is widely known in the art and may be easily carried out using techniques. Polyclonal antibodies may be produced by injecting the protein antigen into an appropriate animal and collecting blood samples from the animal to obtain sera containing antibodies using affinity technology known in the art.

When the method of the present disclosure is performed using an antibody or an aptamer, the present disclosure may be used for diagnosing arthritis by performing conventional immunoassay methods.

The immunoassay may be performed by a variety of quantitative or qualitative immunoassay protocols. The immunoassay format includes, but is not limited to, radioimmunoassay analysis, radioactive immunoprecipitation, immunoprecipitation, immunohistochemical staining, ELISA (enzyme-linked immunosorbant assay), Capture-ELISA, sandwich assay, flow cytometry, immunofluorescence and immune affinity purified. The immunoassay or the immuno staining method is described in Enzyme Immunoassay, E. T. Maggio, ed., CRC Press, Boca Raton, Fla., 1980; Gaastra, W., Enzyme-linked immunosorbent assay (ELISA), in Methods in Molecular Biology, Vol. 1, Walker, J. M. ed., Humana Press, NJ, 1984; and Ed Harlow and David Lane, Using Antibodies: A Laboratory Manual, Cold Spring Harbor Laboratory Press, 1999 and the literatures are inserted as reference in herein.

For example, when the method of the present disclosure is performed using radioimmunoassay analysis, the antibody labeled with radioactive isotopes (e.g., $C^{14}$, $I^{125}$, $P^{32}$ and $S_{35}$) may be used for detecting a marker of the present invention.

When the method of the present disclosure is performed using the ELISA, certain examples of the present invention comprise the steps of: (i) coating unknown cell cytolysate samples of interest for analysis on the surface of a solid substrate; (ii) contacting the cell cytolysate with antibody for the marker as the primary antibody; (iii) contacting the resultant of step (ii) with the secondary antibody conjugated enzyme; and (iv) detecting the enzyme activity.

The appropriate solid substrate is hydrocarbon polymers (e.g., polystyrene and polypropylene), glass, metal, or gel, and most preferably a micro-titer plate.

The appropriate secondary antibody conjugated enzyme includes, but is not limited to, color-developing reaction, fluorescent reaction, luminescent reaction or infrared reaction, for example, alkaline phosphatase, β-galactosidase, horseradish peroxidase, luciferase and cytochrome P450. Where alkaline phosphatase is used for the enzyme binding to the secondary antibody, bromochloroindolylphosphate (BCIP), nitro blue tetrazolium (NBT), naphthol-AS-B1-phosphate and ECF (enhanced chemifluorescence) may be used as a substrate for color-developing reactions. In the case of using horseradish peroxidase, chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) and naphtol/pyronine may be used as a substrate; and in the case of using glucose oxidase, t-NBT (nitroblue tetrazolium) or m-PMS (phenzaine methosulfate) may be used as a substrate.

When the method of the present disclosure is performed using the Capture-ELISA, certain examples of the present invention comprise the steps of: (i) coating the antibody for the marker as capturing antibody on the surface of a solid substrate; (ii) contacting the sample with the capturing antibody; (iii) contacting the resultant of step (ii) with the detecting antibody which is combined with label generating signal and react specifically to the HIF-2α protein; and (iv) detecting the signal from the label.

The detecting antibody has the label generating detectable a signal. The label includes, but is not limited to, chemical (e.g., biotin), enzyme (alkaline phosphatase, β-galactosidase, horseradish peroxidase and cytochrome P450), radioactive material (e.g., $C^{14}$, $I^{125}$, $P^{32}$ and $S^{35}$), fluorescent material (e.g., fluorescein), luminescent material, chemiluminescent material and FRET (fluorescence resonance energy transfer). A variety of labels and labeling methods are described in Ed. Harlow and David Lane, Using Antibodies: A Laboratory Manual, Cold Spring Harbor Laboratory Press, 1999.

The final measurement of enzyme activity or measurement of the signal may be carried out in accordance with a variety of methods known in the art. The detection of this signal permits to qualitative or quantitative analysis of the marker of the present invention. In the case of using biotin as label, the signal is easily detected using streptavidin. In the case of using luciferase as label, the signal is easily detected using luciferin.

According to another embodiment of this invention, the present invention may use aptamers specific to markers instead of antibodies. Aptamers include oligo nucleic acid and peptide molecules, of which details can be found in Bock L C et al., Nature 355 (6360):5646 (1992); Hoppe-Seyler F, Butz K "Peptide aptamers: powerful new tools for molecular medicine". J Mol Med. 78(8):42630 (2000); Cohen B A, Colas P, Brent R. "An artificial cell-cycle inhibitor isolated from a combinatorial library". Proc Natl Acad Sci USA. 95(24):142727 (1998).

The intensity of the final signal obtained in the immunoassay described above is analyzed to determine arthritis. Where the expression of the present biomarker protein in a biological sample becomes decreased such that the signal is weaker than those of normal biological samples (e.g., chondrocytes, tissues, blood, plasma or serum), the biological sample is determined to have arthritis. In addition, where the expression of cartilage degeneration-inducing factors (e.g., MMP-1, MMP-3, MMP-9, MMP-12, MMP-13, ADAMTS-4, ADAMTS-5, PTGS-2 or NOS2) whose expressions are regulated by the present biomarker protein becomes decreased or the phosphorylation of MAP kinases (e.g., ERK, JNK or p38 MAP kinase) becomes more inhibited compared with normal biological samples, the biological sample is determined to have arthritis.

The composition of the present invention may optionally include other reagents along with components described above. For instance, where the present kit may be used for nucleic acid amplification, it may optionally include the reagents required for performing PCR reactions such as buffers, DNA polymerase (thermostable DNA polymerase obtained from *Thermus aquaticus* (Taq), *Thermus thermophilus* (Tth), *Thermus filiformis, Thermis flavus, Thermococcus literalis*, and *Pyrococcus furiosus* (Pfu)), DNA polymerase cofactors, and dNTPs. Where the present composition is manufactured to provide kits, it typically is adapted to contain in separate packaging or compartments the constituents afore-described.

According to a preferable embodiment, the present composition is used for microarray. According to a preferable embodiment, the present composition is used for nucleic acid amplification.

Using microarray in the method of the present invention, probes are immobilized on the solid surface of microarray. The method of the present invention utilizing gene amplification includes primers.

Probes or primers used in the present invention have a sequence complementary to a nucleotide sequence encoding HIF-2α. The term "complementary" with reference to sequence used herein refers to a sequence having complementarity to the extent that the sequence hybridizes or anneals specifically with the nucleotide sequence described above under certain hybridization or annealing conditions. In this regard, the term "complementary" used herein has different meaning from the term "perfectly complementary". The primer or probe of this invention may include one or more mismatch base sequences where it is able to specifically hybridize with the above-described nucleotide sequences.

The term "primer" used herein means a single-stranded oligonucleotide which is capable of acting as a point of initiation of template-directed DNA synthesis when placed under proper conditions (i.e., in the presence of four different nucleoside triphosphates and a thermostable enzyme) in an appropriate buffer and at a suitable temperature. The suitable length of primers will depend on many factors, including temperature, application and source of primer, generally, 15-30 nucleotides in length. In general, shorter primers need lower temperature to form stable hybridization duplexes to templates.

The sequences of primers are not required to have perfectly complementary sequence to templates. The sequences of primers may comprise some mismatches, so long as they can be hybridized with templates and serve as primers. Therefore, the primers of this invention are not required to have perfectly complementary sequence to the nucleotide sequence as described above; it is sufficient that they have complementarity to the extent that they anneals specifically to the nucleotide sequence of the gene for acting as a point of initiation of synthesis. The primer design may be conveniently performed with referring to the above-described nucleotide sequences. For instance, the primer design may be carried out using computer programs for primer design (e.g., PRIMER 3 program).

The term "probe" used herein refers to a linear oligomer of natural or modified monomers or linkages, including deoxyribonucleotides, ribonucleotides and the like, which is capable of specifically hybridizing with a target nucleotide sequence, whether occurring naturally or produced synthetically. The probe used in the present method may be prepared in the form of preferably single-stranded and oligodeoxyribonucleotide probe.

To prepare primers or probes, the nucleotide sequence of the present biomarker may be found in the GenBank (Accession No. NM_010137.3, SEQ ID NO:1), and primers or probes may be designed by reference with the nucleotide sequence afore-mentioned.

In microarray, the present probes serve as a hybridizable array element and are immobilized on a substrate. A preferable substrate includes suitable solid or semi-solid supporters, such as membrane, filter, chip, slide, wafer, fiber, magnetic or nonmagnetic bead, gel, tubing, plate, macromolecule, microparticle and capillary tube. The hybridizable array elements are arranged and immobilized on the substrate. Such immobilization occurs through chemical binding or covalent binding such as UV. In an embodiment of this invention, the hybridizable array elements are bound to a glass surface modified to contain epoxy compound or aldehyde group or to a polylysin-coated surface using UV. Further, the hybridizable array elements are bound to a substrate through linkers (e.g., ethylene glycol oligomer and diamine).

DNAs to be examined with a microarry of this invention may be labeled, and hybridized with array elements on microarray. Various hybridization conditions are applicable, and for the detection and analysis of the extent of hybridization, various methods are available depending on labels used.

The present kit for identifying arthritis may be used in accordance with hybridization. For such analysis, probes, which have a complementary sequence to the nucleotide sequence of the biomarkers of this invention as set forth, are used.

Using probes hybridizable with the nucleotide sequence of the biomarkers of this invention, arthritis may be determined by hybridization-based assay.

Labels linking to the probes may generate a signal to detect hybridization and bound to oligonucleotide. Suitable labels include fluorophores (e.g., fluorescein, phycoerythrin, rhodamine, lissamine, Cy3 and Cy5 (Pharmacia)), chromophores, chemiluminescents, magnetic particles, radioisotopes (e.g., $P^{32}$ and $S^{35}$), mass labels, electron dense particles, enzymes (e.g., alkaline phosphatase or horseradish peroxidase), cofactors, substrates for enzymes, heavy metals (e.g., gold), and haptens having specific binding partners, e.g., an antibody, streptavidin, biotin, digoxigenin and chelating group, but not limited to. Labeling is performed according to various methods known in the art, such as nick translation, random priming (Multiprime DNA labeling systems booklet, "Amersham" (1989)) and kination (Maxam & Gilbert, *Methods in Enzymology*, 65: 499 (1986)). The labels generate signal detectable by fluorescence, radioactivity, measurement of color development, mass measurement, X-ray diffraction or absorption, magnetic force, enzymatic activity, mass analysis, binding affinity, high frequency hybridization or nanocrystal.

The nucleic acid sample to be analyzed may be prepared using mRNA from various biosamples. Preferably, the biosample is articular cartilage tissue cells. Instead of probes, cDNA of interest may be labeled for hyribridization-based analysis.

Probes are hybridized with cDNA molecules under stringent conditions. Suitable hybridization conditions may be routinely determined by optimization procedures. To establish a protocol for use of laboratory, these procedures may be carried out by various methods known to those ordinarily skilled in the art. Conditions such as temperature, concentration of components, hybridization and washing times, buffer components, and their pH and ionic strength may be varied depending on various factors, including the length and GC content of probes and target nucleotide sequence. The detailed conditions for hybridization can be found in Joseph Sambrook, et al., *Molecular Cloning, A Laboratory Manual*, Cold Spring Harbor Laboratory Press, Cold Spring Harbor, N.Y. (2001); and M. L. M. Anderson, *Nucleic Acid Hybridization*, Springer-Verlag New York Inc. N.Y. (1999). For example, the high stringent condition includes hybridization in 0.5 M $NaHPO_4$, 7% SDS (sodium dodecyl sulfate) and 1 mM EDTA at 65° C. and washing in 0.1×SSC (standard saline citrate)/0.1% SDS at 68° C. Also, the high stringent condition includes washing in 6×SSC/0.05% sodium pyrophosphate at 48° C. The low stringent condition includes e.g., washing in 0.2×SSC/0.1% SDS at 42° C.

Following hybridization reactions, a hybridization signal indicative of the occurrence of hybridization is then measured. The hybridization signal may be analyzed by a variety of methods depending on labels. For example, where probes are labeled with enzymes, the occurrence of hybridization may be detected by reacting substrates for enzymes with hybridization resultants. The enzyme/substrate pair useful in this invention includes, but is not limited to, a pair of peroxidase (e.g., horseradish peroxidase) and chloronaphtol, aminoethylcarbazol, diaminobenzidine, D-luciferin, lucigenin (bis-N-methylacridinium nitrate), resorufin benzyl ether, luminol, Amplex Red reagent (10-acetyl-3,7-dihydroxyphenoxazine), HYR (p-phenylenediamine-HCl and pyrocatechol), TMB (3,3,5,5-tetramethylbenzidine), ABTS (2,2-Azine-di[3-ethylbenzthiazoline sulfonate]), o-phenylenediamine (OPD) and naphtol/pyronine; a pair of alkaline phosphatase and bromochloroindolylphosphate (BCIP), nitro blue tetrazolium (NBT), naphthol-AS-B1-phosphate and ECF substrate; and a pair of glucose oxidase and t-NBT (nitroblue tetrazolium) or m-PMS (phenzaine methosulfate). Where probes are labeled with gold particles, the occurrence of hybridization may be detected by silver staining method using silver nitrate. In these connections, where the present method for identifying arthritis is carried out by hybridization, it comprises the steps of: (i) hybridizing a nucleic acid sample to a probe having a nucleotide sequence complementary to the nucleotide sequence of the biomarker of this invention as set forth; and (ii) detecting the occurrence of hybridization. The signal intensity from hybridization is indicative of arthritis. When the hybridization signal to the biomarker of this invention from a sample to be diagnosed is measured to be weaker than normal samples (e.g., normal tissues or cells from articular cartilage), the sample can be determined to have arthritis.

According to a preferable embodiment, the kit of this invention may be a kit for gene amplification.

The term used herein "amplification" refers to reactions for amplifying nucleic acid molecules. A multitude of amplification reactions have been suggested in the art, including polymerase chain reaction (hereinafter referred to as PCR) (U.S. Pat. Nos. 4,683,195, 4,683,202, and 4,800,159), reverse transcription-polymerase chain reaction (hereinafter referred to as RT-PCR) (Sambrook, J. et al., *Molecular Cloning. A Laboratory Manual*, 3rd ed. Cold Spring Harbor Press (2001)), the methods of Miller, H. I. (WO 89/06700) and Davey, C. et al. (EP 329,822), ligase chain reaction (LCR), Gap-LCR (WO 90/01069), repair chain reaction (EP 439,182), transcription-mediated amplification (TMA; WO 88/10315), self sustained sequence replication (WO 90/06995), selective amplification of target polynucleotide sequences (U.S. Pat. No. 6,410,276), consensus sequence primed polymerase chain reaction (CP-PCR; U.S. Pat. No. 4,437,975), arbitrarily primed polymerase chain reaction (AP-PCR; U.S. Pat. Nos. 5,413,909 and 5,861, 245), nucleic acid sequence based amplification (NASBA; U.S. Pat. Nos. 5,130,238, 5,409,818, 5,554,517 and 6,063, 603), strand displacement amplification and loop-mediated isothermal amplification (LAMP), but not limited to. Other amplification methods that may be used are described in U.S. Pat. Nos. 5,242,794, 5,494,810, 4,988,617 and in U.S. Ser. No. 09/854,317.

PCR is one of the most predominant processes for nucleic acid amplification and a number of its variations and applications have been developed. For example, for improving PCR specificity or sensitivity, touchdown PCR, hot start PCR, nested PCR and booster PCR have been developed with modifying traditional PCR procedures. In addition, real-time PCR, differential display PCR (DD-PCR), rapid amplification of cDNA ends (RACE), multiplex PCR, inverse polymerase chain reaction (IPCR), vectorette PCR and thermal asymmetric interlaced PCR (TAIL-PCR) have been suggested for certain applications. The details of PCR can be found in McPherson, M. J., and Moller, S. G. PCR. BIOS Scientific Publishers, Springer-Verlag New York Berlin Heidelberg, N.Y. (2000), the teachings of which are incorporated herein by reference in its entity.

Most preferably, PCR of the present invention is carried out using a real-time PCR.

Where the present kit is carried out using primers, the nucleic acid amplification is executed for analyzing the expression level of the nucleotide sequence of the present biomarkers. Because the present invention is intended to assess the expression level of the nucleotide sequence of the present biomarkers, their mRNA levels in samples (e.g., tissues or cells from articular cartilage, blood, plasma, serum or urine) are analyzed. Therefore, the present invention may be generally carried out by nucleic acid amplifications using mRNA molecules in samples as templates and primers to be annealed to mRNA or cDNA.

For obtaining mRNA molecules, total RNA is isolated from samples. The isolation of total RNA may be performed by various methods (Sambrook, J. et al., *Molecular Cloning. A Laboratory Manual*, 3rd ed. Cold Spring Harbor Press (2001); Tesniere, C. et al., *Plant Mol. Biol. Rep.*, 9: 242 (1991); Ausubel, F. M. et al., *Current Protocols in Molecular Biology*, John Willey & Sons (1987); and Chomczynski, P. et al., *Anal. Biochem.* 162: 156 (1987)). For example, total RNA in cells may be isolated using Trizol. Afterwards, cDNA molecules are synthesized using mRNA molecules isolated and then amplified. Since total RNA molecules used in the present invention are isolated from human samples, mRNA molecules have poly-A tails and converted to cDNA by use of dT primer and reverse transcriptase (*PNAS USA*, 85: 8998 (1988); Libert F, et al., *Science*, 244: 569 (1989); and Sambrook, J. et al., *Molecular Cloning. A Laboratory Manual*, 3rd ed. Cold Spring Harbor Press (2001)). cDNA molecules synthesized are then amplified by amplification reactions.

The primers used for the present invention is hybridized or annealed to a region on template so that double-stranded structure is formed. Conditions of nucleic acid hybridization suitable for forming such double stranded structures are described by Joseph Sambrook, et al., *Molecular Cloning, A Laboratory Manual*, Cold Spring Harbor Laboratory Press, Cold Spring Harbor, N.Y. (2001) and Haymes, B. D., et al., *Nucleic Acid Hybridization, A Practical Approach*, IRL Press, Washington, D.C. (1985).

A variety of DNA polymerases can be used in the amplification step of the present methods, which includes "Klenow" fragment of *E. coli* DNA polymerase I, a thermostable DNA polymerase and bacteriophage T7 DNA polymerase. Preferably, the polymerase is a thermostable DNA polymerase obtained from a variety of bacterial species, including *Thermus aquaticus* (Taq), *Thermus thermophilus* (Tth), *Thermus filiformis, Thermis flavus, Thermococcus literalis*, and *Pyrococcus furiosus* (Pfu).

When a polymerization reaction is being conducted, it is preferable to provide the components required for such reaction in excess in the reaction vessel. Excess in reference to components of the amplification reaction refers to an amount of each component such that the ability to achieve the desired amplification is not substantially limited by the concentration of that component. It is desirable to provide to the reaction mixture an amount of required cofactors such as $Mg^{2+}$, and dATP, dCTP, dGTP and dTTP in sufficient quantity to support the degree of amplification desired. All of the enzymes used in this amplification reaction may be active under the same reaction conditions. Indeed, buffers exist in which all enzymes are near their optimal reaction conditions. Therefore, the amplification process of the present invention can be done in a single reaction volume without any change of conditions such as addition of reactants.

Annealing or hybridization in the present invention is performed under stringent conditions that allow for specific binding between the target nucleotide sequence and the primer. Such stringent conditions for annealing will be sequence-dependent and varied depending on environmental parameters.

The amplified cDNA to the nucleotide sequence of the biomarkers of this invention are then analyzed to assess their expression level using suitable methods. For example, the amplified products are resolved by a gel electrophoresis and the bands generated are analyzed to assess the expression level of the nucleotide sequence of the present biomarkers. When the expression level of the nucleotide sequence of the present biomarkers from a sample to be diagnosed is measured to be lower than normal samples (e.g., normal tissues or cells from articular cartilage, blood, plasma or serum), the sample can be determined to have arthritis.

In these connections, where the present method for identifying arthritis biomarkers is carried out by amplification reactions using cDNA, it comprises the steps of: (i) amplifying a nucleic acid sample by use of a primer to be annealed to the nucleotide sequence of the present biomarkers as set forth; and (ii) analyzing the amplified products to determine the expression level of the nucleotide sequence of the present biomarkers.

The biomarkers of the present invention are biomolecules expressed highly in arthritis. The high expression of biomarkers may be measured at mRNA or protein level. The term "high expression" means that the nucleotide sequence of interest in a sample to be analyzed is much more highly expressed than that in the normal sample, for instance, a case analyzed as high expression according to analysis methods known to those skilled in the art, e.g., RT-PCR method or ELISA method (See, Sambrook, J., et al., *Molecular Cloning. A Laboratory Manual*, 3rd ed. Cold Spring Harbor Press (2001)). Using analysis methods as described above, where the bimarkers of the present invention are much more highly expressed at a range of 2-5 folds than in normal cells tissues, this case is determined as "high expression" and identified as development of arthritis in the present invention.

In further aspect of the present invention, there is provided a method for screening a therapeutic agent for treating arthritis, comprising:

(a) contacting a test substance of interest for analysis to cells comprising a nucleotide sequence encoding the HIF-2α protein; and (b) analyzing the expression level of the HIF-2α protein, wherein where the test substance inhibits the HIF-2α expression in mRNA level or protein level, it is determined as the therapeutic agent for treating arthritis.

In still further aspect of the present invention, there is provided a method for screening a therapeutic agent for treating arthritis, comprising:

(a) contacting a test substance of interest for analysis to the HIF-2α protein and a transcription-regulating sequence binding to the HIF-2α protein; and (b) analyzing the binding affinity of the transcription-regulating sequence to the HIF-2α protein, wherein where the test substance inhibits the binding of the transcription-regulating sequence to the HIF-2α, it is determined as the therapeutic agent for treating arthritis.

Since the method of the present invention follows the process of analyzing the expression levels of HIF-2α of the present method described above, the common descriptions between them are omitted in order to avoid undue redundancy leading to the complexity of this specification.

The present invention may further comprise the step (pre-a) of inducing arthritis by treatment with proinflammatory cytokines or mechanical means before the step (a).

According to a preferred embodiment, the cells used are derived from a cartilage tissue of an animal.

According to the present method, cells expressing HIF-2α are first contacted to a sample to be analyzed. The cells expressing HIF-2α are cells endogenously or transiently expressing HIF-2α, most preferably, chondrocytes. The term "test substance" used herein in conjunction with the present screening method refers to a material tested in the present method for analyzing the influence on the expression level of HIF-2α. The test substance includes siRNA (small interference RNA), shRNA (short hairpin RNA), miRNA (microRNA), ribozyme, DNAzyme, PNA (peptide nucleic acids), antisense oligonucleotides, antibodies, aptamers, extracts of natural sources and chemical substances, but not limited to.

Afterwards, the expression of the HIF-2α coding nucleotide sequence or the binding affinity of the transcription-regulating sequence to the HIF-2α protein in cells treated with the test substance is measured. The measurement of the expression levels may be carried out according to methods as described above, and the test substance may be determined as the therapeutic agent for treating arthritis where the test substance inhibits the expression of the HIF-2α protein or inhibits the binding of the transcription-regulating sequence to the HIF-2α.

According to a preferred embodiment, the transcription-regulating sequence binding to the HIF-2α protein comprises a CGTG conserved nucleotide sequence.

According to a preferred embodiment, the HIF-2α protein and the transcription-regulating sequence to the HIF-2α protein are present in cells.

According to a preferred embodiment, the transcription-regulating sequence binding to the HIF-2α protein further comprises a reporter gene at its downstream direction. The expression of the reporter gene is dependent on the activity of promoters to be analyzed and therefore becomes indicative of the activity of promoters by measuring amounts or activities of proteins expressed. The exemplified reporter gene includes luciferase gene, chloramphenicol acetyltransferase gene, β-galactosidase gene, human growth hormone gene, green fluorescent protein gene and secreted placental alkaline phosphatase, but not limited to.

The amount of proteins expressed by reporter genes may be measured by methods disclosed in de Wet J. et al, Mol. Cell Biol., 7:725-737 (1987) for luciferase; Gorman C. et al, Mol. Cell Biol., 2:1044-1051 (1982) for chloramphenicol acetyltransferase; Hall C. V. et al, J. Mol. Appl. Genet., 2:101-109 (1983) for β-galactosidase; Selden R. et al., Mol. Cell Biol., 6:3173-3179 (1986) for human growth hormone; Chalfie M. et al, Science, 263:802-805 (1994) for green fluorescent protein and Berger, J. et al, Gene, 66:1-10 (1988) for secreted placental alkaline phosphatase.

According to a preferred embodiment, the arthritis is osteoarthritis, degenerative joint disease, osteochondritis dissecans, ligament injuries, meniscus injuries, malalignment of joint, osteonecrosis, rheumatoid arthritis, juvenile idiopathic arthritis, trauma, inflammatory arthritis or septic arthritis caused by infection.

In further aspect of the present invention, there is provided a gene delivery system for inducing arthritis comprising a nucleotide sequence of interest for delivery into cells; wherein the nucleotide sequence is a nucleotide sequence encoding the HIF-2α protein.

To construct the present gene delivery system, it is preferred that the HIF-2α-encoding nucleotide sequence is contained in a suitable expression construct. According the expression construct, it is preferred that the HIF-2α-encoding nucleotide sequence is operatively linked to a promoter. The term used herein "promoter" means a DNA sequence that regulates the expression of a coding sequence or a functional RNA. The term "operatively linked" refers to functional linkage between a nucleic acid expression control sequence (such as a promoter, signal sequence, or array of transcription factor binding sites) and a second nucleic acid sequence, wherein the expression control sequence affects transcription and/or translation of the nucleic acid corresponding to the second sequence. According to the present invention, the promoter linked to the HIF-2α is operable in, preferably, animal, more preferably, mammalian cells, to control transcription of the HIF-2α, including the promoters derived from the genome of mammalian cells or from mammalian viruses, for example, CMV (cytomegalovirus) promoter, CII promoter, the adenovirus late promoter, the vaccinia virus 7.5K promoter, SV40 promoter, HSV tk promoter, RSV promoter, EF1 alpha promoter, metallothionein promoter, beta-actin promoter, human IL-2 gene promoter, human IFN gene promoter, human IL-4 gene promoter, human lymphotoxin gene promoter, human GM-CSF gene promoter, inducible promoter, tumor cell specific promoter (e.g., TERT promoter, PSA promoter, PSMA promoter, CEA promoter, E2F promoter and AFP promoter) and tissue specific promoter (e.g., albumin promoter). Most preferably, the promoter is CMV promoter.

Preferably, the expression constructs used in the present invention comprises polyadenylated sequence (e.g., bovine growth hormone terminator and polyadenylated sequence derived from SV40).

According to a preferred embodiment, HIF-2α-encoding nucleotide sequence used in the present invention has the structure of "promoter-HIF-2α-encoding nucleotide sequence-polyadenylated sequence".

The gene delivery system of the present invention may be manufactured in various forms including (i) a naked recombinant DNA molecule, (ii) a plasmid, (iii) a virus vector and (iv) the liposome or niosome encapsulating the naked recombinant DNA molecule or the plasmid.

The HIF-2α-encoding nucleotide sequence of the present invention comprises any of gene delivery system used in gene therapy by those skilled in the art, preferably, plasmid, adenovirus (Lockett L J, et al., *Clin. Cancer Res.*, 3:2075-2080 (1997)), adeno-associated virus (AAV, Lashford L S., et al., *Gene Therapy Technologies, Applications and Regulations* Ed. A. Meager, 1999), retrovirus (Gunzburg W H, et al., Retroviral vectors. *Gene Therapy Technologies, Applications and Regulations* Ed. A. Meager, 1999), lentivirus (Wang G. et al., *J. Clin. Invest.* 104(11):R55-62 (1999)), herpes simplex virus (Chamber R., et al., *Proc. Natl. Acad. Sci USA,* 92:1411-1415 (1995)), vaccinia virus (Puhlmann M. et al., *Human Gene Therapy,* 10:649-657 (1999)) liposome ((Methods in Molecular Biology, Vol 199, S. C. Basu and M. Basu (Eds.), Human Press 2002)) or niosome. Most preferably, the gene delivery system of this invention is constructed by incorporating the HIF-2α-encoding nucleotide sequence to adenovirus.

i. Adenovirus

Adenoviruses have been usually employed as a gene delivery system because of its mid-sized genome, ease of manipulation, high titer, wide target-cell range, and high infectivity. Both ends of the viral genome contains 100-200 bp ITRs (inverted terminal repeats), which are cis elements necessary for viral DNA replication and packaging. The E1 region (E1A and E1B) encodes proteins responsible for the regulation of transcription of the viral genome and a few cellular genes. The expression of the E2 region (E2A and E2B) results in the synthesis of the proteins for viral DNA replication.

Of adenoviral vectors developed so far, the replication incompetent adenovirus having the deleted E1 region is usually used. The deleted E3 region in adenoviral vectors may provide an insertion site for transgenes (Thimmappaya, B. et al., *Cell,* 31:543-551 (1982); and Riordan, J. R. et al., *Science,* 245:1066-1073 (1989)). Therefore, it is preferred that the nucleotide sequence encoding the CCN5 protein or CCN2ΔCT protein of this invention is inserted into either the deleted E1 region (E1A region and/or E1B region, preferably, E1B region) or the deleted E3 region, more preferably, the deleted E3 region. The nucleotide sequence of interest to be delivered is preferably inserted into either the deleted E1 region (E1A region and/or E1B region, preferably, E1B region) or the deleted E3 region, more preferably, the deleted E1 region. Furthermore, the inserted sequences may be incorporated into the deleted E4 region. The term used herein "deletion" with reference to viral genome encompasses whole deletion and partial deletion as well.

According to the most preferred embodiment of the present invention, the adenovirus gene transduction system of the present invention comprises "promoter—the HIF-2α gene-poly A sequence". The "promoter—the HIF-2α gene-poly A sequence" is inserted into the deleted E1 region (E1A region and/or E1B region, preferably, E1B region) or the E3 region, preferably, the deleted E3 region.

In nature, adenovirus can package approximately 105% of the wild-type genome, providing capacity for about 2 extra kb of DNA (Ghosh-Choudhury et al., *EMBO J.,* 6:1733-1739 (1987)). In this regard, the foreign sequences described above inserted into adenovirus may be further inserted into adenoviral wild-type genome.

The adenovirus may be of any of the 42 different known serotypes or subgroups A-F. Adenovirus type 5 of subgroup C is the most preferred starting material for constructing the adenoviral gene delivery system of this invention. A great deal of biochemical and genetic information about adenovirus type 5 is known.

The foreign genes delivered by the present adenoviral gene delivery system are episomal, and therefore, have low genotoxicity to host cells. Therefore, gene therapy using the adenoviral gene delivery system of this invention may be considerably safe.

ii. Retrovirus

Retroviruses capable of carrying relatively large exogenous genes have been used as viral gene delivery vectors in the senses that they integrate their genome into a host genome and have broad host spectrum.

In order to construct a retroviral vector, the HIF-2α gene is inserted into the viral genome in the place of certain viral sequences to produce a replication-defective virus. To produce virions, a packaging cell line containing the gag, pol and env genes but without the LTR (long terminal repeat) and ψ components is constructed (Mann et al., *Cell,* 33:153-159 (1983)). When a recombinant plasmid containing the HIF-2α gene, LTR and ψ is introduced into this cell line, the ψ sequence allows the RNA transcript of the recombinant plasmid to be packaged into viral particles, which are then secreted into the culture media (Nicolas and Rubinstein "Retroviral vectors," In: *Vectors: A survey of molecular cloning vectors and their uses*, Rodriguez and Denhardt (eds.), Stoneham: Butterworth, 494-513 (1988)). The media containing the recombinant retroviruses is then collected, optionally concentrated and used for gene delivery.

A successful gene transfer using the second-generation retroviral vector has been reported. Kasahara et al. (*Science,* 266:1373-1376 (1994)) prepared variants of moloney murine leukemia virus in which the EPO (erythropoietin) sequence is inserted in the place of the envelope region, consequently, producing chimeric proteins having novel binding properties. Likely, the present gene delivery system can be constructed in accordance with the construction strategies for the second-generation retroviral vector.

iii. AAV Vector

Adeno-associated viruses are capable of infecting non-dividing cells and various types of cells, making them useful in constructing the gene delivery system of this invention. The detailed descriptions for use and preparation of AAV vector are found in U.S. Pat. Nos. 5,139,941 and 4,797,368.

Research results for AAV as gene delivery systems are disclosed in LaFace et al, *Viology,* 162:483486 (1988), Zhou et al., *Exp. Hematol.* (NY), 21:928-933 (1993), Walsh et al, *J. Clin. Invest.,* 94:1440-1448 (1994) and Flotte et al., *Gene Therapy,* 2:29-37 (1995). Recently, an AAV vector has been approved for Phase I human trials for the treatment of cystic fibrosis.

Typically, a recombinant AAV virus is made by cotransfecting a plasmid containing the gene of interest (i.e., relaxin gene and nucleotide sequence of interest to be delivered) flanked by the two AAV terminal repeats (McLaughlin et al., 1988; Samulski et al., 1989) and an expression plasmid containing the wild type AAV coding sequences without the terminal repeats (McCarty et al., *J. Virol.,* 65:2936-2945 (1991)).

iv. Other Viral Vectors

Other virus vectors may be used for the gene transduction system in the present invention. Vectors derived from viruses such as vaccinia virus (Puhlmann M. et al., *Human Gene Therapy* 10:649-657 (1999); Ridgeway, "Mammalian expression vectors," In: *Vectors: A survey of molecular cloning vectors and their uses.* Rodriguez and Denhardt, eds. Stoneham: Butterworth, 467-492 (1988); Baichwal and Sugden, "Vectors for gene transfer derived from animal DNA viruses: Transient and stable expression of transferred genes," In: Kucherlapati R, ed. *Gene transfer.* New York: Plenum Press, 117-148 (1986) and Coupar et al., *Gene,* 68:1-10 (1988)), lentivirus (Wang G. et al., *J. Clin. Invest.* 104(11): R55-62 (1999)) and herpes simplex virus (Chamber R., et al., *Proc. Natl. Acad. Sci USA* 92:1411-1415 (1995)) may be used in the present delivery systems for transferring the HIF-2α gene into cells.

v. Liposome

Liposomes are formed spontaneously when phospholipids are suspended in an excess of aqueous medium. Liposome-mediated nucleic acid delivery has been very successful as described in Nicolau and Sene, *Biochim. Biophys. Acta,* 721: 185-190 (1982) and Nicolau et al., *Methods Enzymol.,* 149: 157-176 (1987). Example of commercially accessible reagents for transfecting animal cells using liposomes includes Lipofectamine (Gibco BRL). Liposomes entrapping the HIF-2α gene interact with cells by mechanism such as endocytosis, adsorption and fusion and then transfer the sequences into cells.

The methods Introduced gene delivery system of the present invention into cells the above-mentioned may be carried out through a variety of methods known in the art. Where the present gene delivery system is constructed on the basis of viral vector construction, the contacting is performed as conventional infection methods known in the art. The infection of hosts using viral vectors is well described in the above-cited publications. Where the present gene delivery system is a naked recombinant DNA molecule or plasmid, the nucleotide sequence to be delivered are introduced into cells by microinjection (Capecchi, M. R., *Cell,* 22:479 (1980) and Harland and Weintraub, *J. Cell Biol.* 101:1094-1099 (1985)), calcium phosphate co-precipitation (Graham, F. L. et al., *Virology,* 52:456 (1973) and Chen and Okayama, *Mol. Cell. Biol.* 7:2745-2752 (1987)), electroporation (Neumann, E. et al., *EMBO J.,* 1:841 (1982) and Tur-Kaspa et al., *Mol. Cell Biol.,* 6:716-718 (1986)), liposome-mediated transfection (Wong, T. K. et al., *Gene,* 10:87 (1980) and Nicolau and Sene, *Biochim. Biophys. Acta,* 721:185-190 (1982); and Nicolau et al., *Methods Enzymol.,* 149:157-176 (1987)), DEAE-dextran treatment (Gopal, *Mol. Cell Biol.,* 5:1188-1190 (1985)) and particle bombardment (Yang et al., *Proc. Natl. Acad. Sci.,* 87:9568-9572 (1990)), and most preferably microinjection.

In still further aspect of the present invention, there is provided a method for preventing or treating arthritis, comprising administering a substance inhibiting the expression of the hypoxia-inducible factor-2α (HIF-2α) gene or the activity of the HIF-2α protein. Since the present invention describes for administration manner and administration dosage of the substance inhibiting the expression of the hypoxia-inducible factor-2α (HIF-2α) gene or the activity of the HIF-2α protein and pharmaceutical composition comprising thereof, the common descriptions between them are omitted in order to avoid undue redundancy leading to the complexity of this specification.

In further aspect of the present invention, there is provided a method for inducing arthritis, comprising contacting to cells a gene delivery system comprising a nucleotide sequence encoding the HIF-2α protein. Since the present invention describes for the gene delivery system comprising a nucleotide sequence encoding the HIF-2α protein and transgenic methods using it, the common descriptions between them are omitted in order to avoid undue redundancy leading to the complexity of this specification.

Advantageous Effects

The features and advantages of the present invention will be summarized as follows:

(a) The present invention relates to a novel use of HIF-2α as regulating factor for cartilage degeneration-inducing factor.

(b) According to the present invention, the HIF-2α of the present invention increases the expression thereof in chondrocytes or tissue in which osteoarthritis is induced, and triggers the expression of various cartilage degeneration factors and the activation of mitogen-activated protein (MAP) kinase.

(c) In addition, when HIF-2α is inhibited, the expression level of cartilage degeneration factors and the phosphorylation of MAP kinase are significantly reduced by the inhibited degree of HIF-2α.

(d) Therefore, the composition of the present invention may be applied to the prevention or treatment of arthritis, and may be used for the development of therapeutics for arthritis.

BRIEF DESCRIPTION OF THE DRAWINGS

FIGS. 6a-6c show that HIF-2α directly regulates MMP (1, 3, 9, 12, 13) and ADAMTS4 by mutating the HIF-2α binding sites of the promoters of these genes (a) together with the sequence of oligonucleotides used to demonstrate the binding between the promoters and HIF-2α (b) and a result of analyzing the binding between the promoters and the oligonucleotides (c).

EXAMPLES OF THE INVENTION

The present invention will now be described in further detail by examples. It would be obvious to those skilled in the art that these examples are intended to be more concretely illustrative and the scope of the present invention as set forth in the appended claims is not limited to or by the examples.

EXAMPLES

Example 1

Identification of HIF-2α as Cartilage Degeneration-Inducing Factor

Figure 1A:
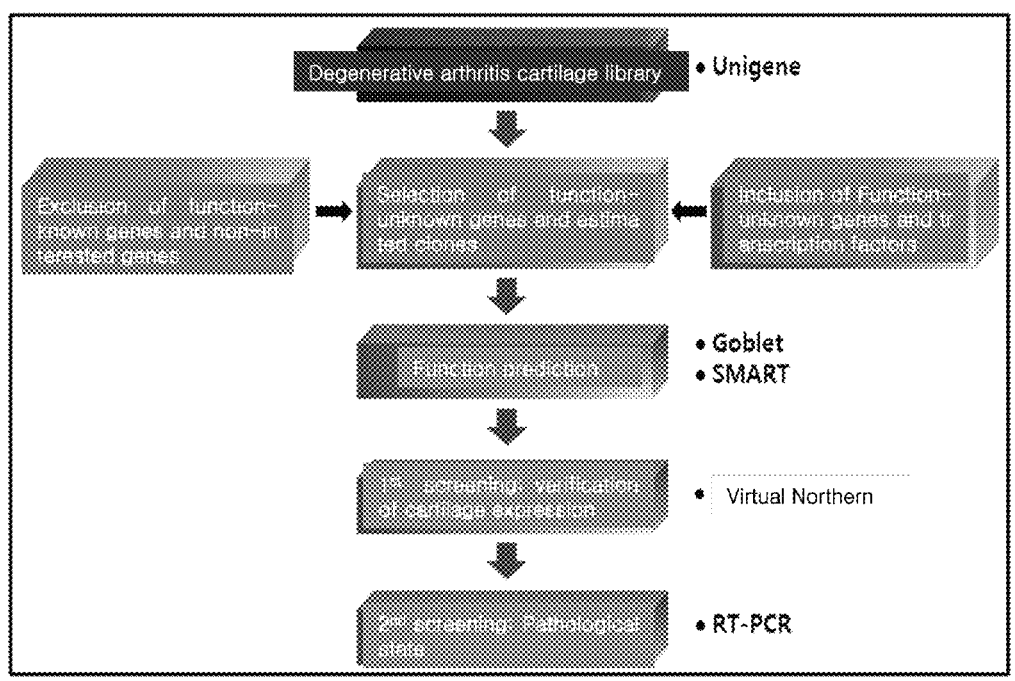
FIGS. 1a and 1b summarize an in silico method for identifying novel genes expected to induce or inhibit degenerative arthritis and FIG. 1c shows a result of screening out HIF-2α through first and second screening (Hs.468410=HIF-2α).
Figure 1B:
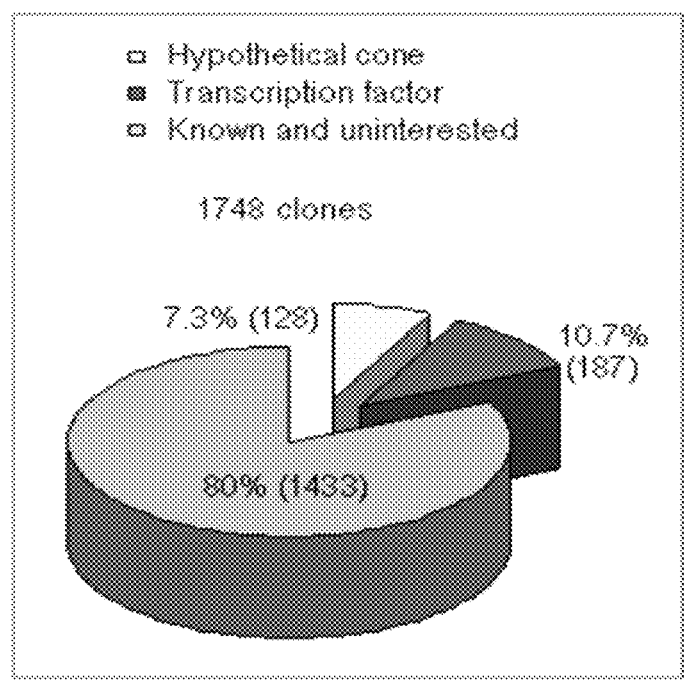
Figure 1C:
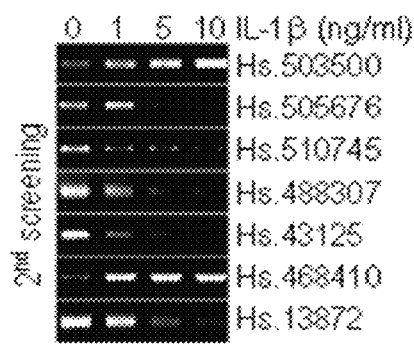

In order to cartilage-specific regulatory genes, the human degenerative cartilage library (#8936) of NCBI (ncbi.nlm.nih.gov)'s UniGene database was analyzed. The inventors classified cartilage-specific genes from the library according to the standard in the literature (Hong, S. et al., J Biol Chem 280, 7685-7693, 2005). That is to say, functionally unknown genes and novel genes were selected based on the literature. Genes exhibiting a larger number of cartilage ESTs than that of non-cartilage ESTs analyzed using serial analysis of gene expression (SAGE)/cDNA virtual Northern (cgap.nci.nih.gov/SAGE) were screened as cartilage-specific genes. Among the selected genes, HIF-2α was screened as a gene functionally characteristic of cartilage degeneration (FIG. 1).

Figure 2A:
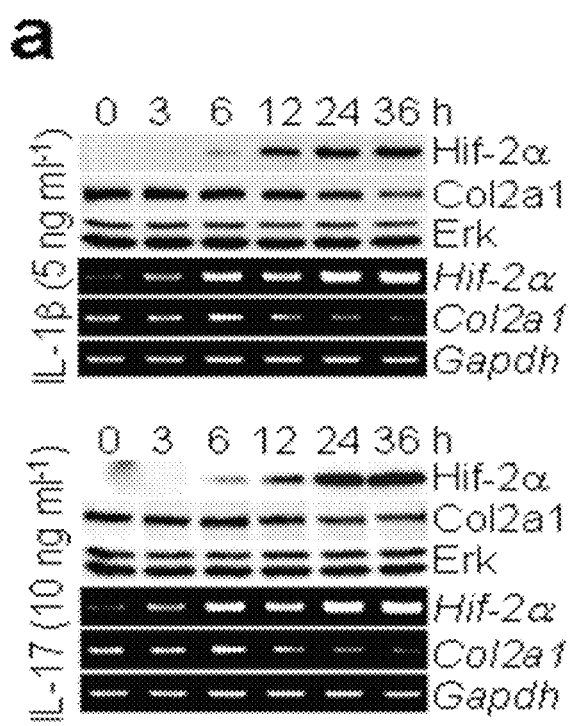
FIGS. 2a-2f show a result showing a mechanism whereby expression of HIF-2α inducing degenerative arthritis is regulated. The expression of HIF-2α is increased by the proinflammatory cytokines interleukin (IL)-1β, IL-18 and IL-21 and TNF-α (a, b). The proinflammatory cytokine IL-1β activates NF-κβ and mitogen-activated protein (MAP) kinase signal transduction pathways (c). During the MAP kinase signal transduction pathway, JNK and NF-κβ are involved in the expression of HIF-2α (d, e). A large amount of IκB and phosphorylated JNK (pJNK) activating NF-κβ are activated in human degenerative joint tissue (f).
Figure 2B:
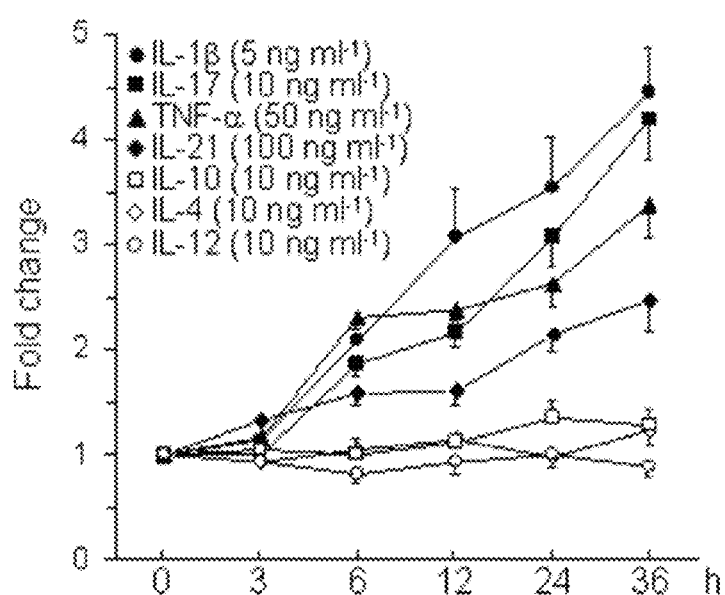
Figure 2C:
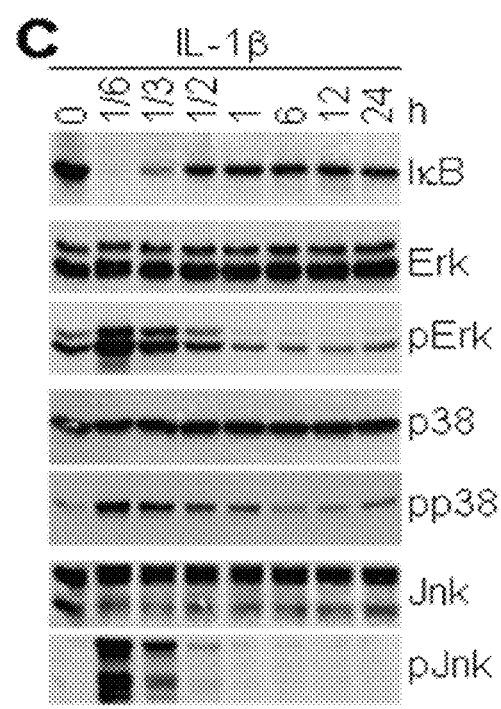
Figure 2D:
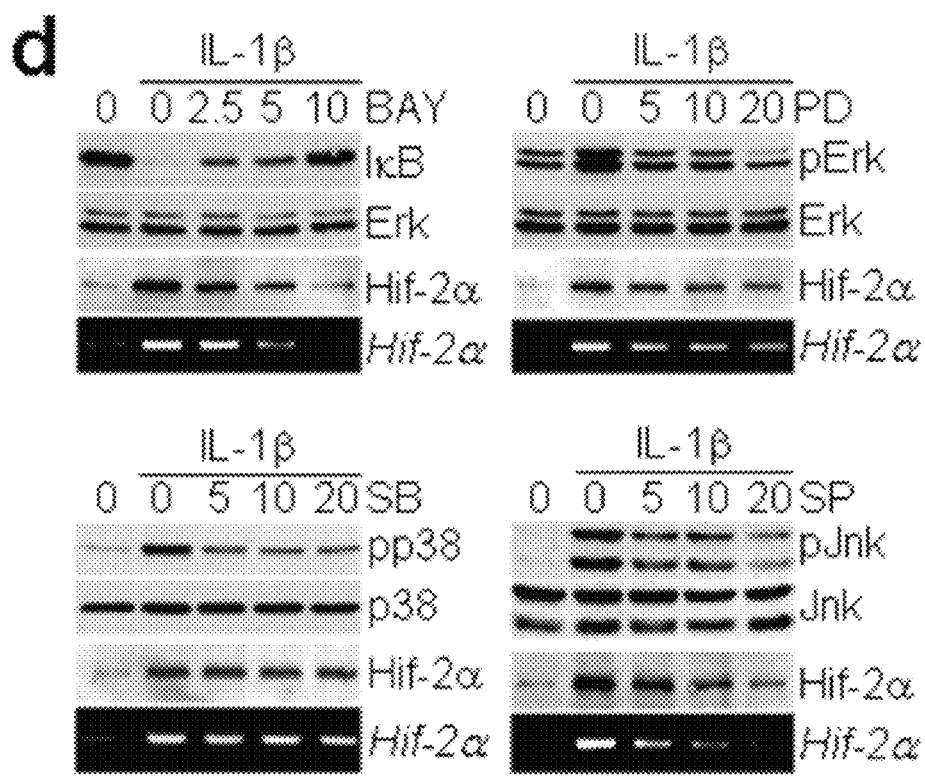
Figure 2E:
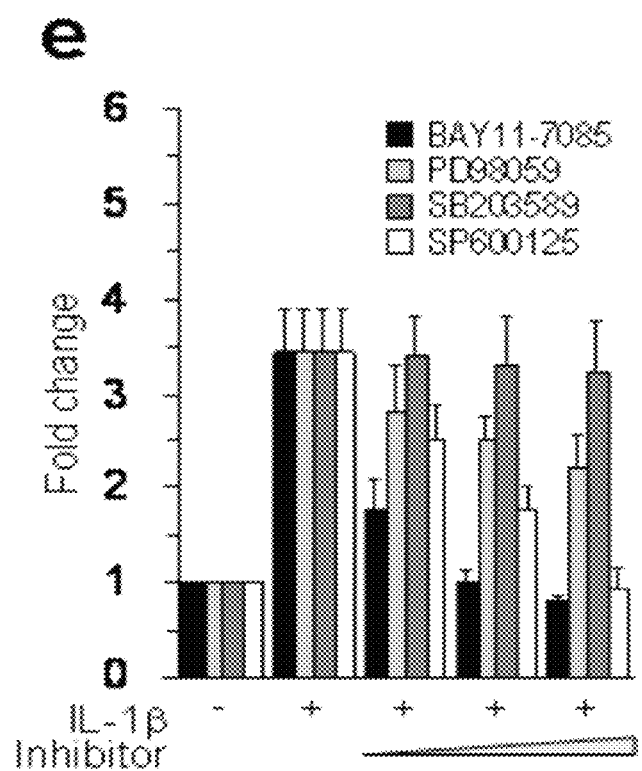
Figure 2F:
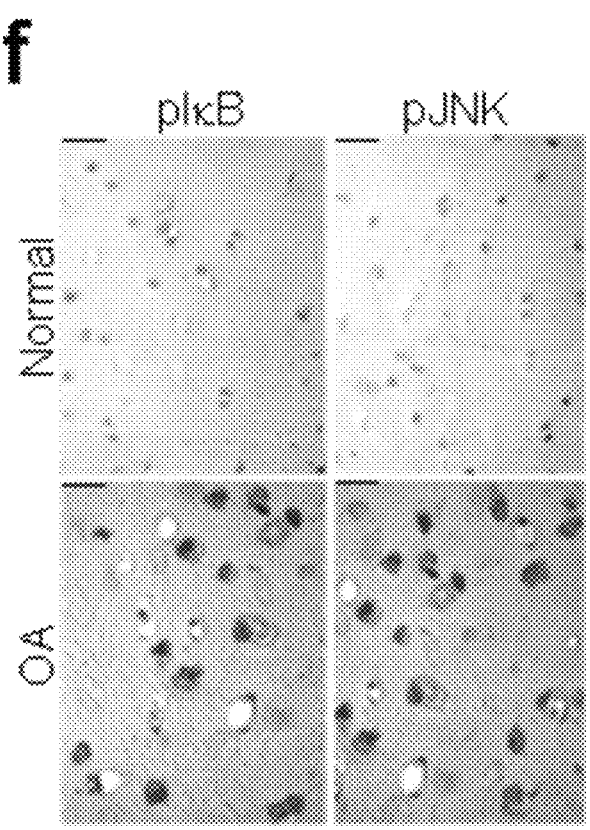

In order to induce pathological condition of cartilage degeneration in knee joint chondrocytes of mouse (Charles River, Japan), the cells were treated with interleukin 1β (IL-1β, Calbiochem, USA), IL-17 (R&D Systems, USA), TNF-α (R&D Systems, USA) or IL-21 (R&D Systems, USA), which are known as proinflammatory cytokines. The expression level of HIF-2α was investigated by RT-PCR, qRT-PCR and western blot. The mouse knee joint chondrocytes were isolated from the knee joint of 8-day-old ICR mouse (Charles River, Japan) and cultured in DMEM (Gibco, USA) containing 10% (v/v) fetal bovine serum (Gibco, USA), 50 μg/mL streptomycin (Sigma-Aldrich, USA) and 50 unit/mL penicillin (Sigma-Aldrich, USA). As a result, it was confirmed that whereas the expression of HIF-2α is increased by the proinflammatory cytokines, it is not affected by the anti-inflammatory cytokines IL-4 (R&D Systems, USA), IL-10 (R&D Systems, USA) and IL-12 (R&D Systems, USA) (FIGS. 2a and 2b). IL-1β activates various signal transduction pathways in chondrocytes. Activation of NF-κβ and degradation of IκB protein were confirmed by western blot, and phosphorylation of extracellular signal-regulated kinase (ERK), c-Jun N-terminal kinase (JNK) and p38 MAP kinase from among mitogen-activated protein (MAP) kinase subtypes was confirmed by western blot (FIG. 2c). When NFkB was inhibited with BAY 11-7085 (BAY, Biomol, USA) or JNK was inhibited with SP600125 (SP, Biomol, USA), expression of HIF-2α transcripts and proteins was decreased remarkably. In contrast, inhibition effect was slightly weak when ERK was inhibited with PD98059 (PD, Tocris Cookson Inc, USA) and there was no effect on HIF-2α expression when p38 MAP kinase was inhibited with SB203580 (SB, Tocris Cookson Inc, USA). Accordingly, it was confirmed through RT-PCR and western blot (FIG. 2d) and quantification of HIF-2α transcripts by real-time RT-PCR (qRT-PCR) that NFkB and JNK regulate the expression of HIF-2α (FIG. 2e). It was confirmed through immunohistochemical staining that IκB and phosphorylated JNK (pJNK) activating NF-κβ are activated in larger amounts in human degenerative articular cartilage tissue (OA; osteoarthritis) as compared to normal cartilage (Normal). This suggests that these signal transduction pathways are activated in degenerative joint tissue (FIG. 2f).

Example 2

Regulation of Expression of Cartilage Degeneration-Inducing Factors by HIF-2α

In order to identify the cartilage degeneration-inducing factors whose expression is regulated by HIF-2α, HIF-2α was overexpressed in mouse knee joint chondrocytes using an adenovirus (Ad-HIF-2α) overexpressing HIF-2α. It was confirmed by RT-PCR (FIG. 3a) and western blot (FIG. 3b) that expression of cartilage degeneration-inducing factors such as MMP (1, 3, 9, 12, 13), ADAMTS4, PTGS2, NOS2, etc. is induced by the Ad-HIF-2α as compared to control (mock virus) and the expression level was quantitated by qRT-PCR (FIGS. 3c and 3d). HIF-2α was overexpressed using the adenovirus as follows. Mouse knee joint chondrocytes were kept in a culture medium for 72 hours. After infecting with control (mock virus, 800 MOI) or the supernatant of the culture of the adenovirus (200, 400, 800 MOI) for 90 minutes, the cells were cultured in a serum-containing medium for 2 days. The cells were recovered and cartilage degeneration-inducing factors were identified by RT-PCR and western blot. GAPDH and ERK were used as loading control. mRNA and protein levels of HIF-2α, MMP, ADAMTS, PTGS2 and NOS2 were measured by RT-PCR and western blot. GAPDH and lamin B were used as loading control. Primers used in PCR are described in Table 1.

TABLE 1

Primer sequence

| Gene | | Primer sequence | SEQ ID NO | Predicted size |
|---|---|---|---|---|
| Human HIF-2α | sense | 5'-ACCCAGACGGATTTCAATGAGC-3' | 8 | 293 bp |
| | antisense | 5'-TTGCTTCCGGCATCAAAG AAG-3 | 9 | |

TABLE 1-continued

Primer sequence

| Gene | | Primer sequence | SEQ ID NO | Predicted size |
|---|---|---|---|---|
| Mouse HIF-2α | sense | 5'-CGAGAAGAACGACGTGGTGTTC-3' | 10 | 370 bp |
| | antisense | 5'-GTGAAGGCGGGCAGGCTCC-3 | 11 | |
| Human MMP1 | sense | 5'-GGAGGGGATGCTCATTTTGATG-3' | 12 | 541 bp |
| | antisense | 5'-TAGGGAAGCCAAAGGAGCTGT-3 | 13 | |
| Rabbit MMP1 | sense | 5'-ATGGACCTGAAGGACAGCT-3' | 14 | 534 bp |
| | antisense | 5'-CCTGCACAGTCCAGTACTT-3 | 15 | |
| Human MMP2 | sense | 5'-GCCTGAGCTCCCGGAAAAGATTG-3' | 16 | 444 bp |
| | antisense | 5'-CAGCAGCCTAGCCAGTCGGATTT-3 | 17 | |
| Mouse MMP2 | sense | 5'-CCAACTACGATGATGAC-3' | 18 | 233 bp |
| | antisense | 5'-ACCAGTGTCAGTATCAG-3 | 19 | |
| Rabbit MMP2 | sense | 5'-CCGTGTGAAGTATGGCAATGC-3' | 20 | 493 bp |
| | antisense | 5'-GCGGTCATCGTCGTAGTTG-3 | 21 | |
| Human MMP3 | sense | 5'-GATGCGCAAGCCCAGGTGTG-3' | 22 | 406 bp |
| | antisense | 5'-GCCAATTTCATGAGCAGCAACGA-3 | 23 | |
| Mouse MMP3 | sense | 5'-TCCTGATGTTGGTGGCTTCAG-3' | 24 | 102 bp |
| | antisense | 5'-TGTCTTGGCAAATCCGGTGTA-3' | 25 | |
| Rabbit MMP3 | sense | 5'-TGTACCCAGTCTACAACGC-3' | 26 | 550 bp |
| | antisense | 5'-TCCAGGGACTCTCTCTTCT-3 | 27 | |
| Human MMP9 | sense | 5'-GGCCAACTACGACACCGACGAC-3' | 28 | 424 bp |
| | antisense | 5'-CGCCGCCACGAGGAACAAAC-3 | 29 | |
| Mouse MMP9 | sense | 5'-ACCACATCGAACTTCGA-3' | 30 | 212 bp |
| | antisense | 5'-CGACCATACAGATACTG-3 | 31 | |
| Rabbit MMP9 | sense | 5'-CTCCTCGTGCTGGGCTGTT-3' | 32 | 449 bp |
| | antisense | 5'-TACACGCGGGTGAAGGTGA-3 | 33 | |
| Human MMP12 | sense | 5'-ATATGTTGACATCAACACAT-3' | 34 | 286 bp |
| | antisense | 5'-ATAAGCAGCTTCAATGCCAG-3 | 35 | |
| Mouse MMP12 | sense | 5'-CCCAGAGGTCAAGATGGATG-3' | 36 | 482 bp |
| | antisense | 5'-GGCTCCATAGAGGGACTGAA-3 | 37 | |
| Rabbit MMP12 | sense | 5'-GGAGCTCATGGAGACTATG-3' | 38 | 460 bp |
| | antisense | 5'-GGACACTGGTTGAACT-3 | 39 | |
| Human MMP13 | sense | 5'-AGGAGCATGGCGACTTCTACCC-3' | 40 | 341 bp |
| | antisense | 5'-TTTGTCTGGCGTTTTTGGATGTT-3 | 41 | |
| Mouse MMP13 | sense | 5'-TGATGGACCTTCTGGTCTTCTGG-3' | 42 | 473 bp |
| | antisense | 5'-CATCCACATGGTTGGGAAGTTCT-3 | 43 | |
| Rabbit MMP13 | sense | 5'-CCTACACCGGCAAGAGTCA-3' | 44 | 460 bp |
| | antisense | 5'-TCTTGGGAATCCCAGTTCA-3 | 45 | |
| Human MMP14 | sense | 5'-ATGAGGCGCCCCCGATGTGG-3' | 46 | 369 bp |
| | antisense | 5'-TCCAATGTTGGGGCCTGGGAAGT-3 | 47 | |
| Mouse MMP14 | sense | 5'-GTGCCCTAGGCCTACATCCG-3' | 48 | 580 bp |
| | antisense | 5'-TTGGGTATCCATCCATCACT-3 | 49 | |
| Rabbit MMP14 | sense | 5'-GCGTACGAGAGGAAGGATG-3' | 50 | 396 bp |
| | antisense | 5'-CCAGCACCAGGAGTAGCAG-3 | 51 | |
| Human MMP15 | sense | 5'-GCTTCGCGGGGAGATGTTCGTGT-3' | 52 | 499 bp |
| | antisense | 5'-CTCCATCCGCAGGCGCTCATTGT-3 | 53 | |
| Mouse MMP15 | sense | 5'-GAGAGATGTTTGTGTTCAAGGG-3' | 54 | 260 bp |
| | antisense | 5'-TGTGTCAATGCGGTCATAGGG-3 | 55 | |
| Rabbit MMP15 | sense | 5'-GTACTGGCGCTTCAACGA-3' | 56 | 550 bp |
| | antisense | 5'-CCACCTCCTCCATCTGCA-3 | 57 | |
| Human ADAMTS4 | sense | 5'-AGAAGAAGTTTGACAAGTGC-3' | 58 | 225 bp |
| | antisense | 5'-GCGTGTATTCACCATTGAG-3 | 59 | |

TABLE 1-continued

Primer sequence

| Gene | | Primer sequence | SEQ ID NO | Predicted size |
|---|---|---|---|---|
| Mouse ADAMTS4 | sense antisense | 5'-CATCCGAAACCCTGTCAACTTG-3' 5'-GCCCATCATCTTCCACAATAGC-3' | 60 61 | 281 bp |
| Rabbit ADAMTS4 | sense antisense | 5'-GGATTGCACGAGGCCCGTC-3' 5'-CACCCGGGGCTCCAATACG-3' | 62 63 | 305 bp |
| Human ADAMTS5 | sense antisense | 5'-ATCACCCAATGCCAAGG-3' 5'-AGCAGAGTAGGAGACAAC-3 | 64 65 | 245 bp |
| Mouse ADAMTS5 | sense antisense | 5'-GCCATTGTAATAACCCTGCACC-3' 5'-TCAGTCCCATCCGTAACCTTTG-3 | 66 67 | 292 bp |
| Rabbit ADAMTS5 | sense antisense | 5'-AGGGCAAGTGTGTGGACAAGA CA-3' 5'-GAAAAGATTTACCTTGGCTGG GC-3 | 68 69 | 237 bp |
| Human COX-2 | sense antisense | 5'-TTCAAATGAGATTGTGGGAAAA-3' 5'-AGATCATCTCTGCCTGAGCT-3' | 70 71 | 303 bp |
| Mouse COX-2 | sense antisense | 5'-GGTCTGGTGCCTGGTCTGATGAT-3' 5'-GTC CTTTCAAGGAGAATGGTGC-3 | 72 73 | 724 bp |
| Rabbit COX-2 | sense antisense | 5'-TCAGCCACGCAGCAAATCCT-3' 5'-GTCATCTGGATGTCAGCACG-3 | 74 75 | 279 bp |
| Human iNOS | sense antisense | 5'-CCATGGAACATCCCAAATAC-3' 5'-TCTGCATGTACTTCATGAAGG-3 | 76 77 | 357 bp |
| Mouse iNOS | sense antisense | 5'-TCACTGGGACAGCACAGA AT-3' 5'-TGTGTCTGCAGATGTGCTGA-3 | 78 79 | 510 bp |
| Rabbit iNOS | sense antisense | 5'-TCACCATCTTCCAGGAGCG-3' 5'-CACAATGCCGAAGTGGTCG-3 | 80 81 | 299 bp |
| Human aggrecan | sense antisense | 5'-GCCTTGAGCAGTTCACCTTC-3' 5'-CTCTTCTACGGGGACAGCAG-3 | 82 83 | 395 bp |
| Mouse aggrecan | sense antisense | 5'-GAAGACGACATCACCATCCAG-3' 5'-CTGTCTTTGTCACCCACACATG-3 | 84 85 | 581 bp |
| Rabbit aggrecan | sense antisense | 5'-CAACGTCGCCAGAGAAGTT-3' 5'-CTTCGCCCTCAGTGATGTT-3' | 86 87 | 581 bp |
| Human Coll-II | sense antisense | 5'-CAGTTGGGAGTAATGCAAG-3' 5'-GCCTGGATAACCTCTGTG-3 | 88 89 | 300 bp |
| Mouse Coll-II | sense antisense | 5'-CACACTGGTAAGTGGGCAAGA-3' 5'-GGATTGTGTTGTTTCAGGGTTCG-3 | 90 91 | 173 bp |
| Rabbit Coll-II | sense antisense | 5'-AGCCGCCATTGATGGTCTC-3' 5'-GACCCCATGCAGTACATG C-3 | 92 93 | 370 bp |
| Human GAPDH | sense antisense | 5'-CGTCTTCACCACCATGGAGA-3' 5'-CGGCCATCACGCCACAGTTT-3 | 94 95 | 300 bp |
| Mouse GAPDH | sense antisense | 5'-TCACTGCCACCCAGAAGAC-3' 5'-TGTAGGCCATGAGGTCCAC-3 | 96 97 | 450 bp |
| Rabbit GAPDH | sense antisense | 5'-TCACCATCTTCCAGGAGCG-3' 5'-CACAATGCCGAAGTGGTCG-3 | 98 99 | 299 bp |

Also, the expression of the cartilage degeneration-inducing factors was investigated after artificially inhibiting expression of HIF-2α using an siRNA specific for HIF-2α. More specifically, mouse knee joint chondrocytes were kept in a culture medium for 72 hours. After infecting with control (C-siRNA, 100 nM) or HIF-2α siRNA (25, 50, 100 nM) for 7 hours, the cells were cultured in a medium containing IL-1B for 1.5 days. The cells were recovered and cartilage degeneration-inducing factors were identified by RT-PCR and western blot. GAPDH and lamin B were used as loading control. Also, mRNA (FIG. 3a) and protein (FIG. 3b) levels of HIF-2α, MMP, ADAMTS, PTGS2 and NOS2 were measured by RT-PCR and western blot and their expression level was quantitated by qRT-PCR (FIGS. 3c and 3d). GAPDH and lamin B were used as loading control. Primers used in PCR are described in Table 1. As a result, it was confirmed that the expression of the cartilage degeneration-inducing factors MMP (1, 3, 9, 12, 13), ADAMTS4, PTGs2, NOS2, etc. is decreased as the expression of HIF-2α is inhibited.

TABLE 2

HIF-2α siRNA oligonucleotide sequence

| Gene | | HIF-2α siRNA oligonucleotide sequence | SEQ ID NO |
|---|---|---|---|
| Rabbit HIF-2α siRNA | sense | 5'-CUCAGUUACAGCCACAUCGUCACUG-3' | 2 |
| | antisense | 5'-CAGUGACGAUGUGGCUGUAACUGAG-3' | 3 |
| Mouse HIF-2α siRNA | sense | 5'-AGUUGUUGUAGACUUUCACCUGGC-3' | 4 |
| | antisense | 5'-GGCCAGGUGAAAGUCUACAACAAC-3' | 5 |
| Control siRNA | sense | 5'-CCUACGCCACCAAUUUCG-3' | 6 |
| | antisense | 5'-ACGAAAUUGGUGGCGUAG-3' | 7 |

Figure 3A:
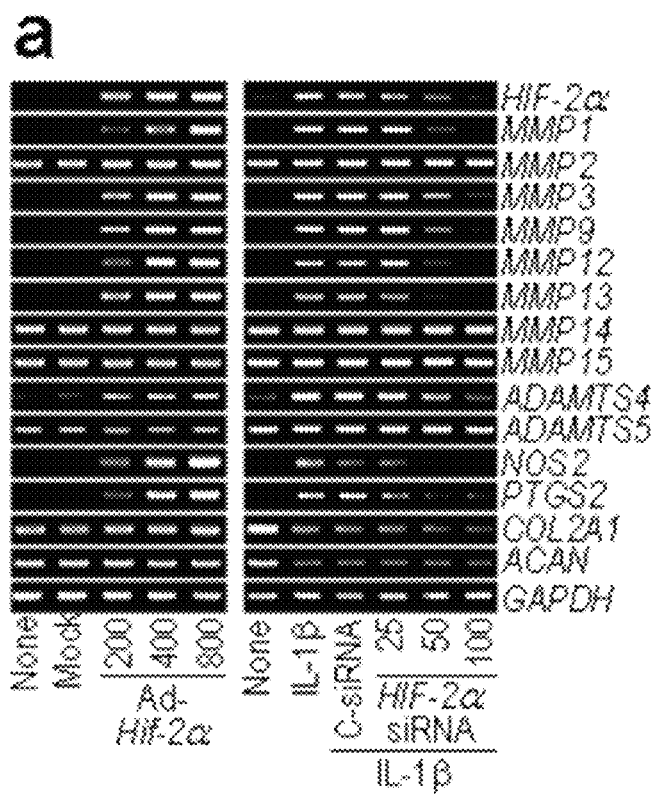
FIGS. 3a-3d show that HIF-2α regulates expression of the cartilage degeneration-inducing factors MMP (1, 3, 9, 12, 13), ADAMTS4, PTGS2, NOS2, etc. in articular chondrocytes. The effect was demonstrated by RT-PCR (a) and western blot (b) after overexpressing HIF-2α or inhibiting its expression using siRNA. Also, transcripts were quantitated by real-time RT-PCR (qRT-PCR) (c, d).
Figure 3B:
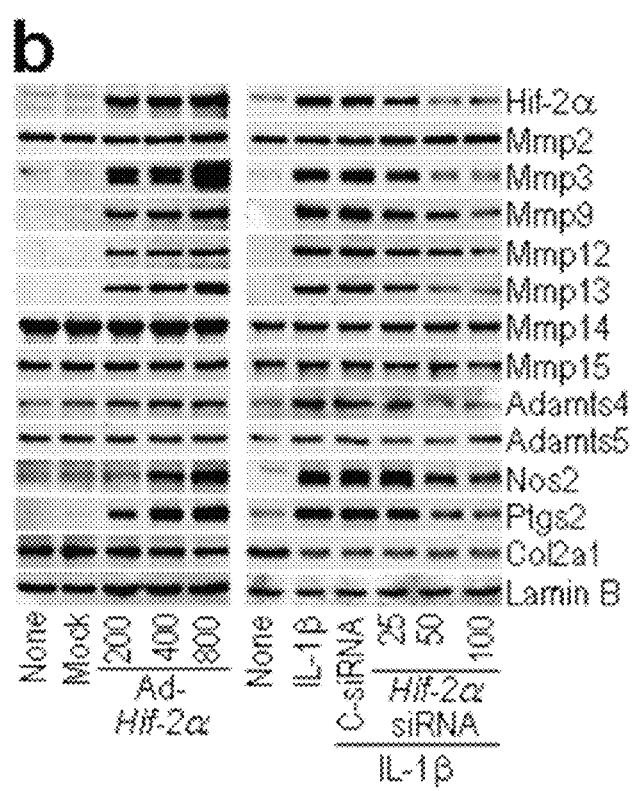
Figure 3C:
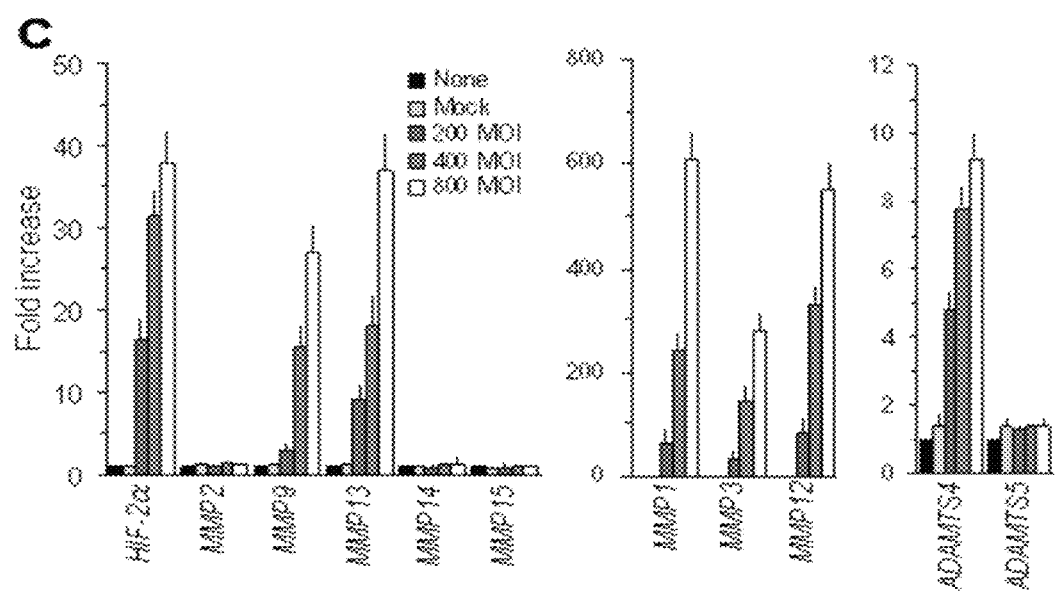
Figure 3D:
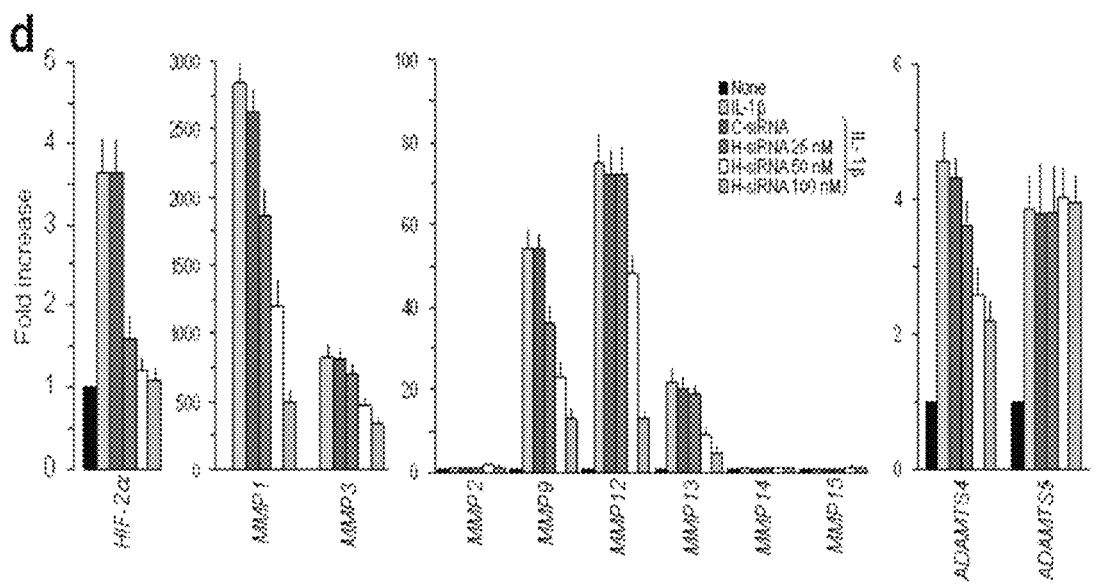
Figure 4A:
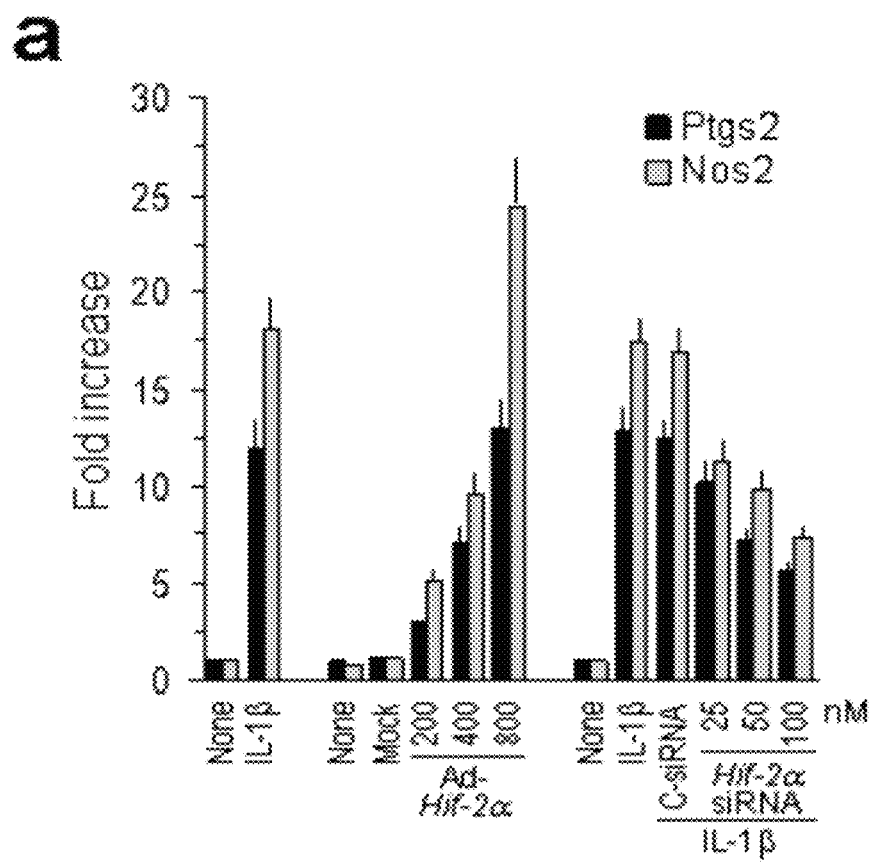
FIGS. 4a and 4b show that HIF-2α regulates expression of the cartilage degeneration-inducing factors PTGS2 and NOS2 in articular chondrocytes. After overexpressing HIF-2α or inhibiting its expression using siRNA, transcripts were quantitated by real-time RT-PCR (a). It was also demonstrated that production of nitric oxide (NO) and prostaglandin E2 (PGE2), which are metabolites of these enzymes, is increased (b).
Figure 4B:
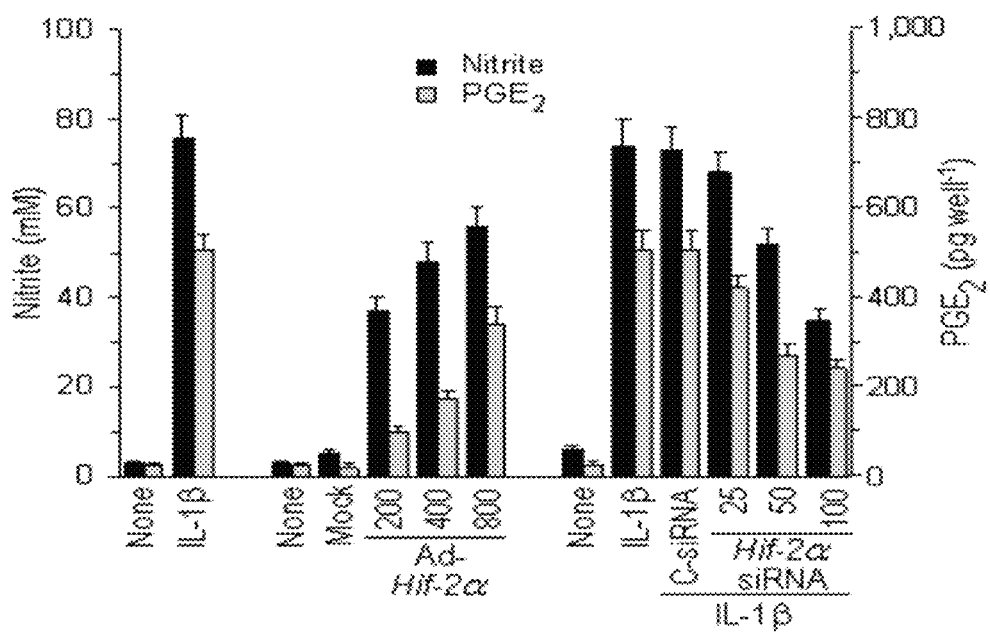

As seen from FIG. 3a, it was confirmed that the artificial regulation of HIF-2α expression in mouse knee joint chondrocytes using Ad-HIF-2α and HIF-2α siRNA resulted in increased PTGS2 expression and decreased NOS2 expression. Also, it was confirmed by qRT-PCR that the expression level of these transcripts is increased by Ad-HIF-2α and decreased by siRNA (FIG. 4a). The experimental procedure was the same as with MMP and ADAMT as described above. NOS2 and PTGS2 regulate cartilage degeneration by inducing production of nitric oxide (NO) and prostaglandin E2 (PGE2), respectively. The level of these metabolites was increased by Ad-HIF-2α and decreased by siRNA, as the expression level of PTGS2 and NOS2 transcripts (FIG. 4b).

Figure 5A:
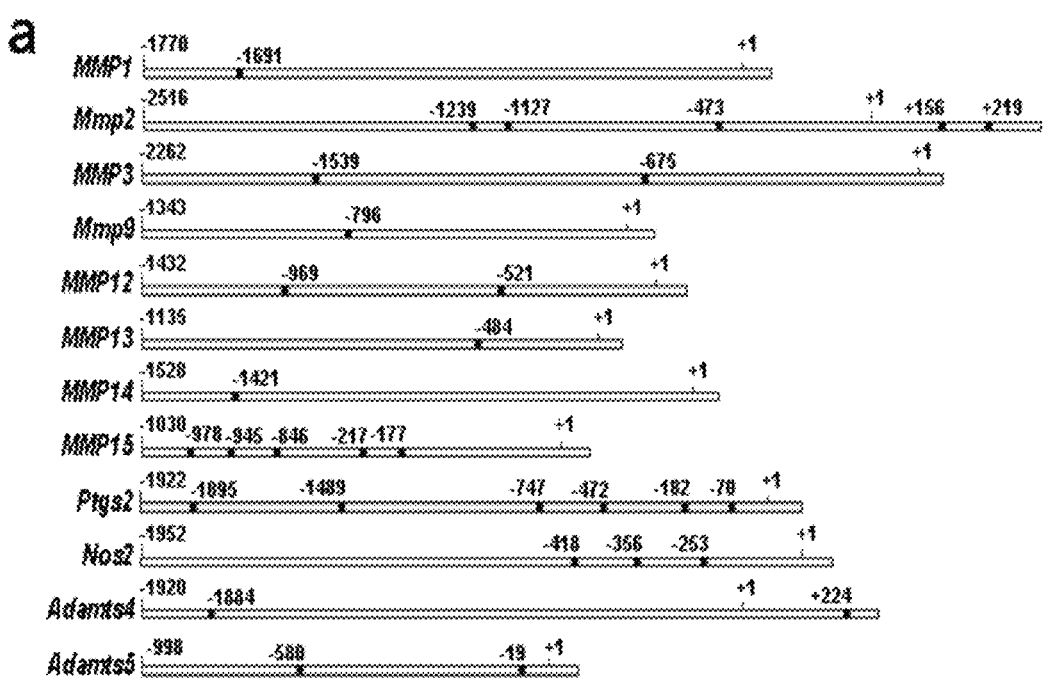
FIGS. 5a and 5b show promoter structure of the target genes of HIF-2α (a) and a result of reporter gene analysis of each promoter showing that the transcriptional activity of MMP (1, 3, 9, 12, 13), ADAMTS4, NOS2 and PTGS2 is regulated by HIF-2α (b).
Figure 5B:
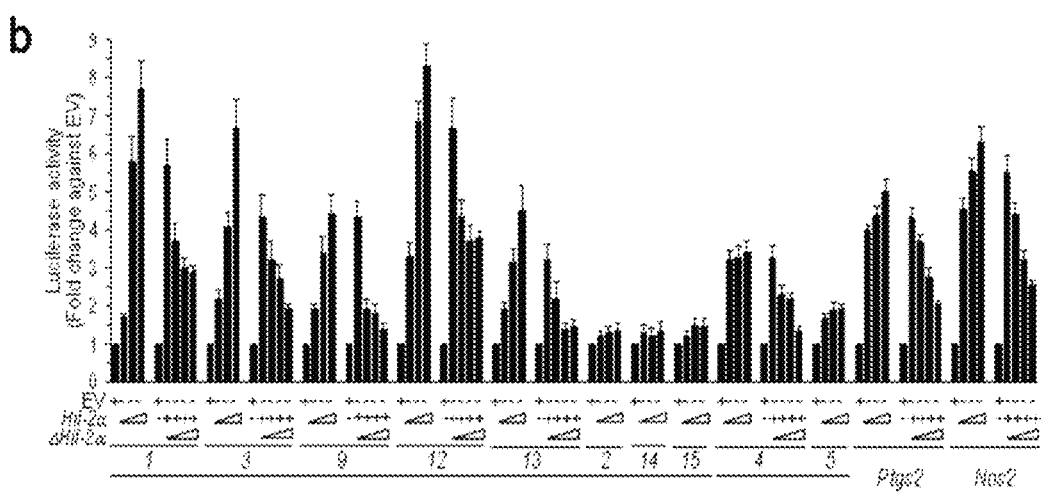
Figure 6A:
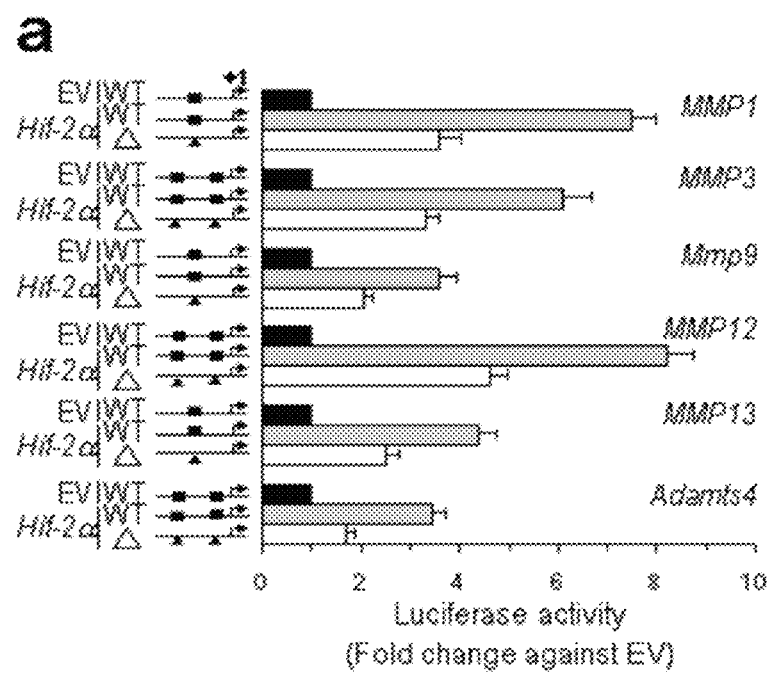
Figure 6C:
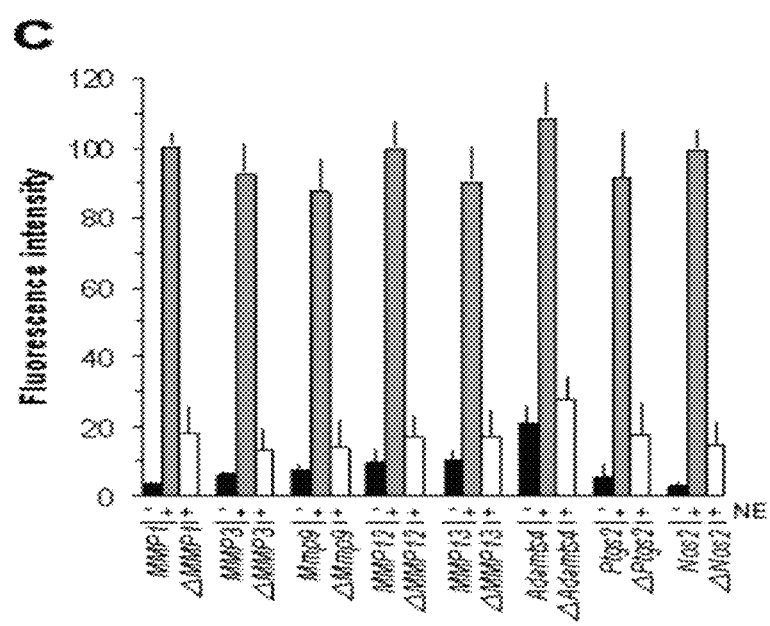

This result means that HIF-2α, which is a transcription factor, can directly regulate transcriptional activity of the cartilage degeneration-inducing factors such as MMP, ADAMTS, PTGS2, NOS2, etc. in chondrocytes as target gene. To demonstrate this, regulation of the cartilage degeneration-inducing factors (MMP, ADAMTS, PTGS2 and NOS2) by HIF-2α was analyzed using promoters of the respective cartilage degeneration-inducing factors. Also, regulation of the cartilage degeneration-inducing factors was investigated after inhibiting HIF-2α by mutating the promoters to inhibit binding with HIF-2α or using dominant negative (dn) HIF-2α (ΔHIF-2α) (FIGS. 5a-5b and FIGS. 6a-6c). The size and HIF-2α binding site of the used promoters are schematically shown in FIG. 5a and the primers used to prepare them are described in Table 3. The regulation of the transcription of the cartilage degeneration-inducing factors by HIF-2α was investigated as follows. Mouse knee joint chondrocytes were kept in a culture medium for 72 hours. After introduction into cells using a promoter (1 μg) of each cartilage degeneration-inducing factor and Lipofectamine 2000 (Invitrogen, USA) as an HIF-2α expressing vector (0.5, 1.0, 1.5 μg), the cells were cultured in a serum-containing medium for 2 days and luciferase activity was measured. As a result, it was confirmed that transcriptional activity of MMP (1, 3, 9, 12, 13), ADAMTS4, PTGS2 and NOS2 was directly increased by HIF-2α when HIF-2α was overexpressed. And, when ΔHIF-2α inhibiting HIF-2α activity was overexpressed, the transcriptional activity of MMP (1, 3, 9, 12, 13), ADATS4, PTGS2 and NOS2 was decreased (FIG. 5b). Also, when the HIF-2α binding site of each promoter was modified from CGTG to AAAG, the transcriptional activity of the target genes was not increased by HIF-2α (FIG. 6a). Protein-DNA binding was analyzed in order to investigate whether HIF-2α binds directly to the promoter of the cartilage degeneration-inducing factors. A protein-DNA binding assay kit (Epigentek) using a double-stranded oligonucleotide corresponding to each promoter part was used for the analysis. Sequences of the normal oligonucleotide and mutated oligonucleotide (Δ) used in the experiment are shown in FIG. 6b. As a result, it was confirmed from fluorescence measurement that HIF-2α binds directly to MMP (1, 3, 9, 12, 13), PTGS2, NOS2 and ADAMTS4 (FIG. 6c). To conclude, it can be seen that the expression of the cartilage degeneration-inducing factors MMP (1, 3, 9, 12, 13), ADAMTS4, PTGS2 and NOS2 in chondrocytes is directly regulated by HIF-2α.

TABLE 3

Primer sequence used for preparation of expression vector and promoter

| Gene | | Primer sequence | SEQ ID NO | Predicted size | Use |
|---|---|---|---|---|---|
| Mouse HIF-2α | sense | 5'-ATGACAGCTGACAAGGAGAA-3' | 100 | 2,622 bp | expression vector |
| | antisense | 5'-GGTGGCCTGGTCCAGA-3' | 101 | | |
| Human HIF-2α | sense | 5'-ATGACAGCTGACAAGGAG-3' | 102 | 1,455 bp | expression vector |
| | antisense | 5'-AGGGCTATTGGGCGTGGA-3' | 103 | | |
| Human MMP1 | sense | 5'-GGAGTCACTTCAGTGGCAAGTGT-3' | 104 | -1,770/+71 | promoter |
| | antisense | 5'-ACTGGCCTTTGTCTTCTTTCTCA-3' | 105 | | |
| Mouse MMP2 | sense | 5'-CGCCTCATAAGTTGTCCA-3' | 106 | -2,226/+302 | promoter |
| | antisense | 5'-CGTTGCGCTCCCGGGCTC-3 | 107 | | |
| Human MMP3 | sense | 5'-CTGTTTGACATTTGCTATGAG-3' | 108 | -2,262/+28 | promoter |
| | antisense | 5'-CCTTGCTGTCTTGCCTGCCTC-3' | 109 | | |
| Mouse MMP9 | sense | 5'-GAGAGTTTTGTAGAGAGCGTAT-3' | 110 | -1,329/+19 | promoter |
| | antisense | 5'-GGTGAGGACCGCAGCTTCTGG-3' | 111 | | |
| Human MMP12 | sense | 5'-GGAGTAGCCTGTAATC-3' | 112 | -1,433/+43 | promoter |
| | antisense | 5'-TAAACTTCTAAACGGATC-3' | 113 | | |

TABLE 3-continued

Primer sequence used for preparation of expression vector and promoter

| Gene | | Primer sequence | SEQ ID NO | Predicted size | Use |
|---|---|---|---|---|---|
| Human MMP13 | sense antisense | 5'-CACGGTACTGAATGTGTGATGTC-3' 5'-CTTGAATGGTGATGCCTGGGGAC-3' | 114 115 | -1,135/+28 | promoter |
| Human MMP14 | sense antisense | 5'-TTTTTTGGCAAGCATCTG-3' 5'-GGTCCGAGACCACCGGGT-3 | 116 117 | -1,528/+234 | promoter |
| Human MMP15 | sense antisense | 5'-CCAAACTTTTTAAAATTGGCTAA-3' 5'-TCTTAAAGGGCCAGTGTGCTCC-3' | 118 119 | -1,030/+353 | promoter |
| Mouse ADAMTS4 | sense antisense | 5'-TGTGCCTTCTCCTTCTGCCAG-3' 5'-CTGCGGCACCAAAATGCTCCA-3 | 120 121 | -1,920/+427 | promoter |
| Mouse ADAMTS5 | sense antisense | 5'-TTTGAAAATGAGAGGGCTGAC-3' 5'-AGTGCGCTGCCCGCCGGGAGG-3' | 122 123 | -998/+858 | promoter |
| Mouse COX-2 | sense antisense | 5'-GTGTATAGCTGGCTGTCCTGAAA-3' 5'-CGCAGAGGTGGCAGCGG-3' | 124 125 | -1,922/+100 | promoter |
| Mouse iNOS | sense antisense | 5'-ATGGAAAGTTATAGTCTC-3' 5'-CAAGACTCACCTTGCAG-3' | 126 127 | -1,952/+148 | promoter |

Example 3

Increased Expression of HIF-2α in Degenerative Joint Tissue

In order to understand the function of HIF-2α in degenerative arthritis, expression of HIF-2α in human degenerative joint tissue and degenerative joint tissue of an animal model (mouse) was investigated first. Cartilage tissue obtained from patients who had undergone artificial joint replacement (Wonkwang University Hospital, Korea) was used as human degenerative joint tissue. Mouse degenerative joint tissue was obtained from STR/ort mice (Harlan Laboratories, Germany) and joint tissue from Normal CBA mouse (Charles River, Japan) was used as control. For confirmation of cartilage tissue degeneration, safranin O staining whereby cartilage tissue is stained specifically was employed. Total RNA used in RT-PCR and qRT-PCR was isolated from respective tissues and cells using RNA STAT-60 (Tel-Test, Woodlands, Tex.) and reverse transcription was performed using ImProm-IITM reverse transcriptase (Promega, Madison, Wis.). The produced cDNA was amplified by PCR using Taq polymerase (TaKaRa Bio, Shiga, Japan). Primers used in PCR are described in Table 1.

Figure 7A:
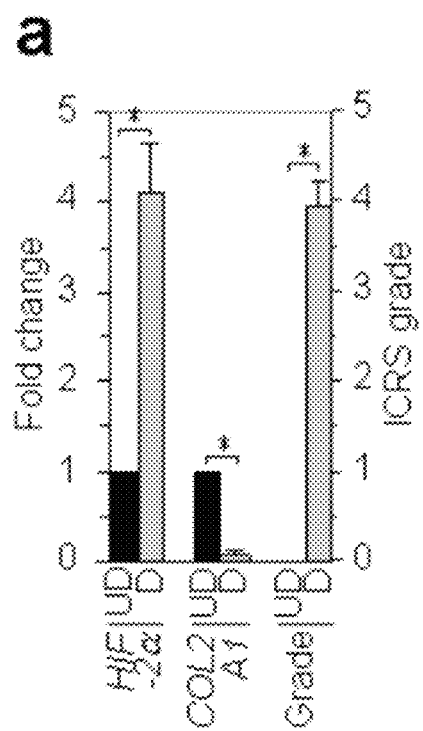
FIGS. 7a-7c show a RT-PCR analysis result showing that expression of HIF-2α is increased and that of type II collagen (COL2A1) is decreased in human degenerative joint tissue together with ICRS grade indicative of the degree of cartilage degeneration (a), a result of confirming expression of HIF-2α in degenerative joint tissue in terms of transcript and protein level (b) and a result of quantifying gene transcripts of cartilage degeneration-inducing factors in healthy normal joint tissue and degenerative joint tissue by RT-PCR and real-time RT-PCR (c).
Figure 7B:
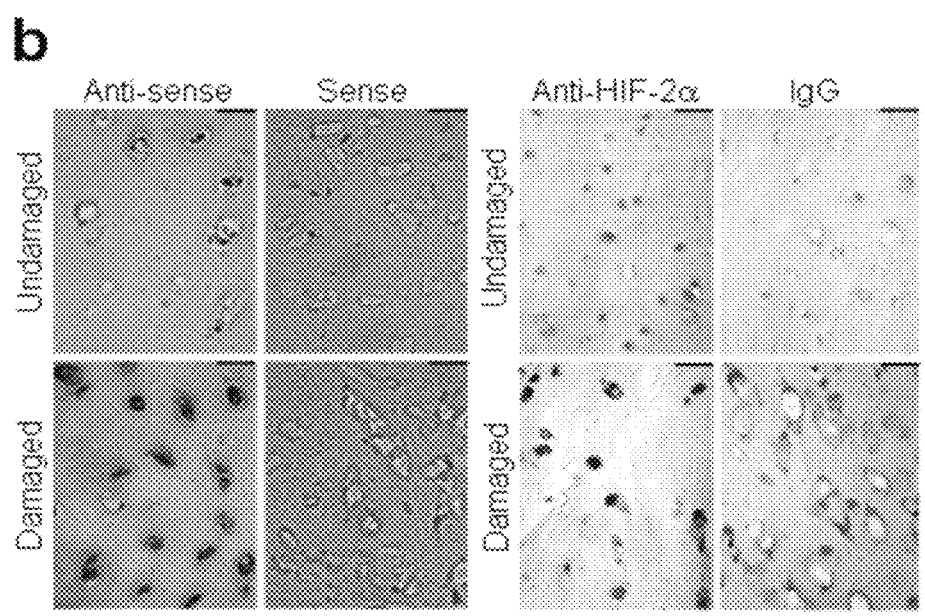
Figure 7C:
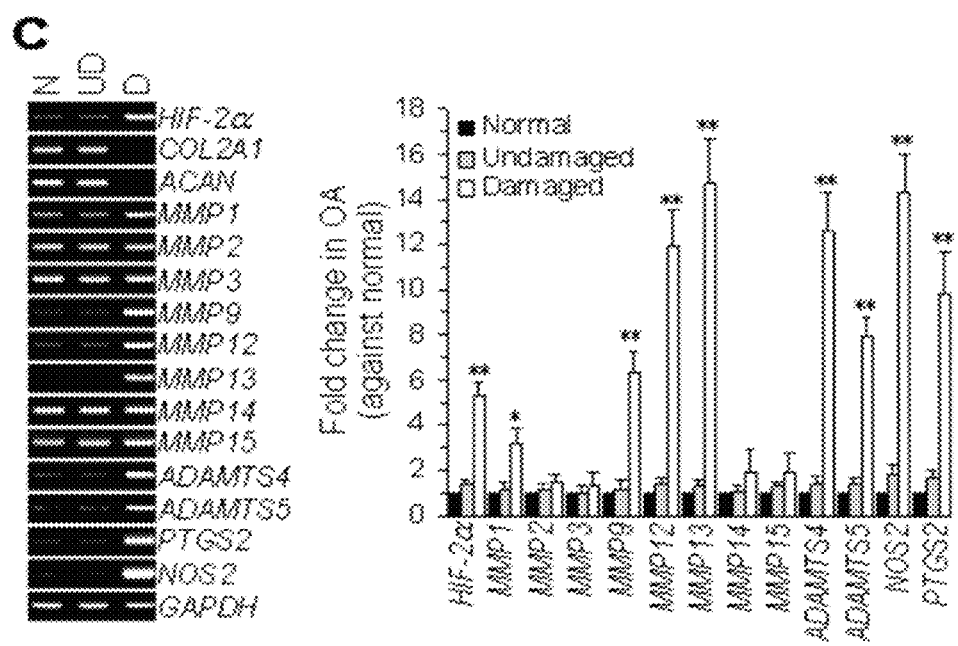

In the human degenerative joint tissue, arthritically damaged part was compared with undamaged part. Cartilage damage was identified by remarkably increased ICRS grade as well as remarkably decreased expression of the chondrogenesis marker type II collagen (Col2a1). Further, rapidly increased expression of HIF-2α was confirmed by RT-PCR (FIG. 7a). Remarkably increased HIF-2α transcripts (mRNA) were found in the arthritically damaged part as compared to the undamaged part through in situ hybridization, and increased protein was confirmed through immunohistochemical staining (FIG. 7b). When expression of cartilage degeneration-inducing factors as target genes of HIF-2α in normal joint tissue, undamaged part and damaged part was investigated by RT-PCR, expression of MMP (1, 9, 12, 13), ADAMTS4, PTGS2 and NOS2 was much higher in the normal cartilage than in the damaged cartilage (FIG. 7c).

Figure 8A:
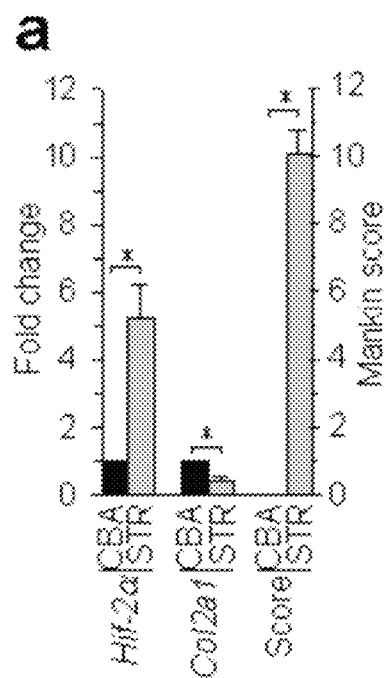
FIGS. 8a-8c show a RT-PCR analysis result showing that expression of HIF-2α is increased and that of type II collagen is decreased in STR/ort mouse, which is an animal model of degenerative arthritis, as compared to wild-type mouse tissue together with Mankin score indicative of the degree of cartilage degeneration (a), a result of safranin O staining showing the degree of cartilage damage as well as increase expression of HIF-2α protein in degenerative joint tissue (b) and a result of quantifying gene transcripts of cartilage degeneration-inducing factors by RT-PCR and real-time RT-PCR (c).
Figure 8B:
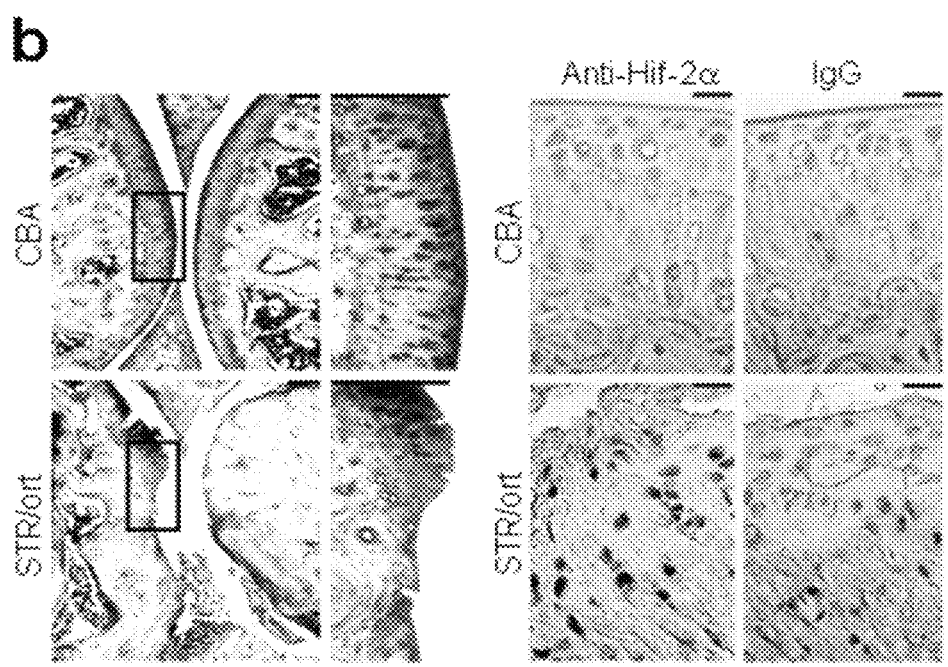
Figure 8C:
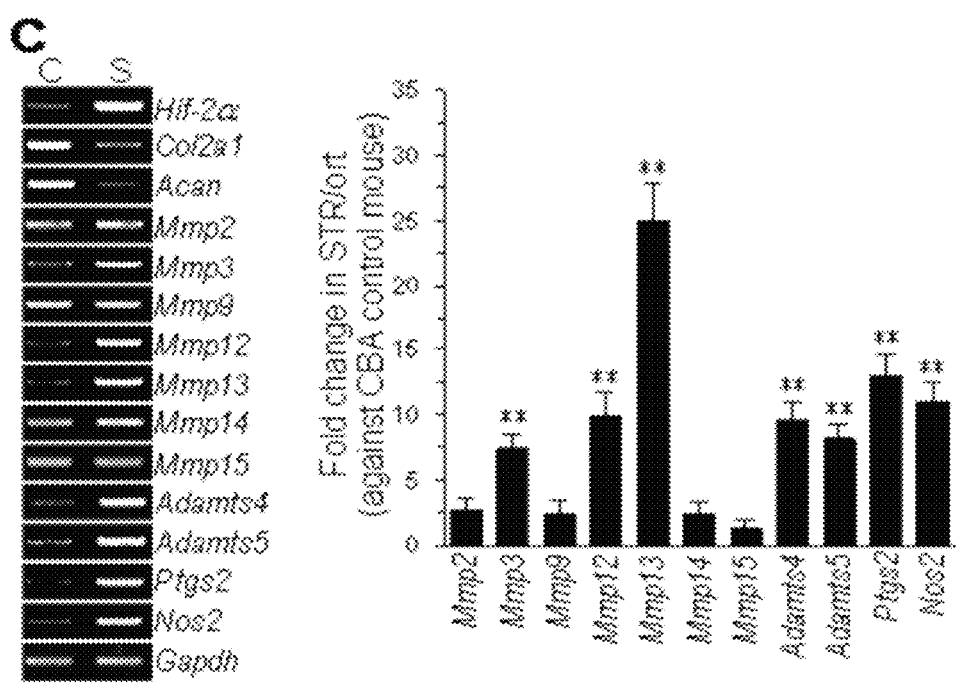

Meanwhile, the cartilage tissue of STR/ort mouse, which is an animal model of degenerative arthritis, was compared with that of normal CBA mouse. Cartilage damage was confirmed in the cartilage tissue from the STR/ort mouse, with remarkably increased Mankin score and remarkably decreased expression of the chondrogenesis marker type II collagen (Col2a1). Also, rapidly increased HIF-2α expression was confirmed by RT-PCR (FIG. 8a). Further, it was confirmed through safranin O staining that the cartilage tissue of the STR/ort mouse was significantly damaged as compared to that of the control CBA mouse. Also, remarkably increased expression of HIF-2α protein was confirmed by immunohistochemical staining (FIG. 8b). When expression of cartilage degeneration-inducing factors as target genes of HIF-2α was investigated in the degenerative joint tissue of the STR/ort mouse as compared to the CBA mouse, remarkably increased expression of MMP (3, 9, 12, 13), ADAMTS4, PTGS2 and NOS2 in the damaged cartilage as compared to normal cartilage was confirmed by RT-PCR (FIG. 8c).

Accordingly, it was confirmed that the expression of HIF-2α is increased both in human degenerative joint tissue and mouse degenerative joint tissue and expression of the cartilage degeneration-inducing factors as target genes of HIF-2α is also increased.

Example 4

Degenerative Arthritis Induced by Overexpression of HIF-2α

Figure 9A:
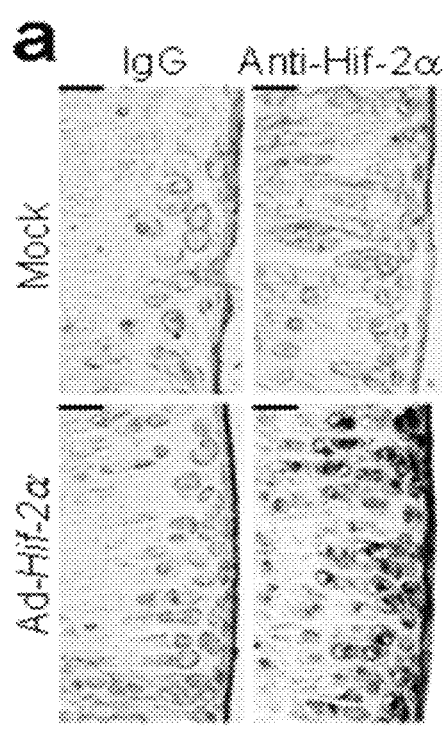
FIGS. 9a-9c show that injection of adenovirus encoding HIF-2α into the articular cartilage of mouse leads to overexpression of HIF-2α in cartilage tissue (a) together with a confirming cartilage damage through safranin O staining and quantifying the degree of cartilage degeneration with Mankin score (b) and a result of quantifying gene transcripts of cartilage degeneration-inducing factors by RT-PCR and real-time RT-PCR (c).
Figure 9B:
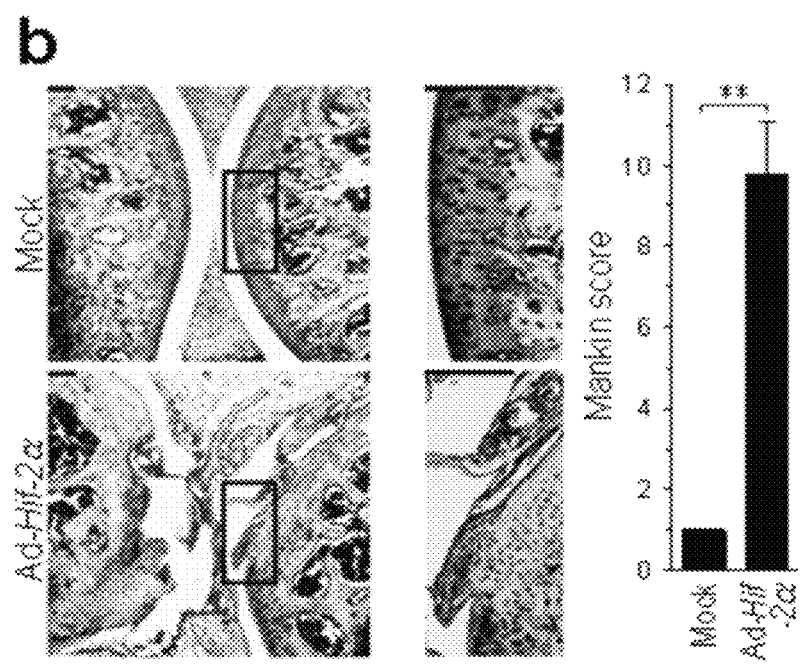
Figure 9C:
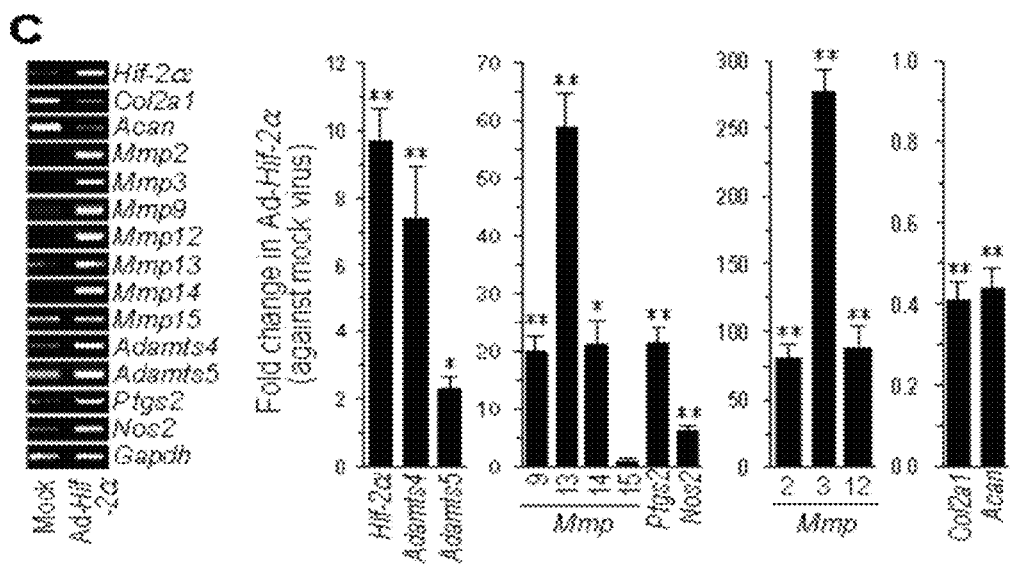

In order to directly identify cartilage degeneration and degenerative arthritis induced by HIF-2α, HIF-2α was overexpressed by injecting control (mock virus) or Ad-HIF-2α (1×109 pfu) into mouse knee joint and cartilage tissue was analyzed 7 days later. More specifically, HIF-2α overexpression in cartilage tissue was investigated immunohistochemically and cartilage degeneration was quantitated with Mankin score by staining the cartilage tissue with safranin O. Also, expression of cartilage degeneration-inducing factors was confirmed by RT-PCR and qRT-PCR when degenerative arthritis was induced by overexpressed HIF-2α. As a result, it was confirmed that HIF-2α was overexpressed in articular cartilage tissue (FIG. 9a) and safranin O staining revealed that the cartilage tissue was severely damaged (FIG. 9b). Also, it was confirmed that the expression of the target genes of HIF-2α, i.e. MMP (3, 9, 12, 13), ADAMTS4, PTGS2 and NOS2, was increased when HIF-2α was overexpressed in the mouse cartilage tissue (FIG. 9c).

Figure 10A:
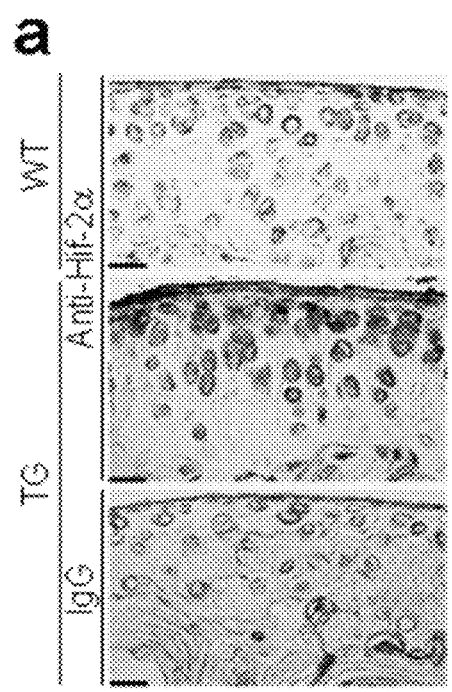
FIGS. 10a-10c show that HIF-2α protein is overexpressed in the articular cartilage of a transgenic mouse overexpressing HIF-2α specifically in chondrocytes (a) and degenerative arthritis is induced in 12-week-old and 45-week-old transgenic mice as compared to normal wild-type mouse (CBA) (b) together with a result of quantifying gene transcripts of cartilage degeneration-inducing factors by RT-PCR and real-time RT-PCR as compared to normal cartilage (c).
Figure 10B:
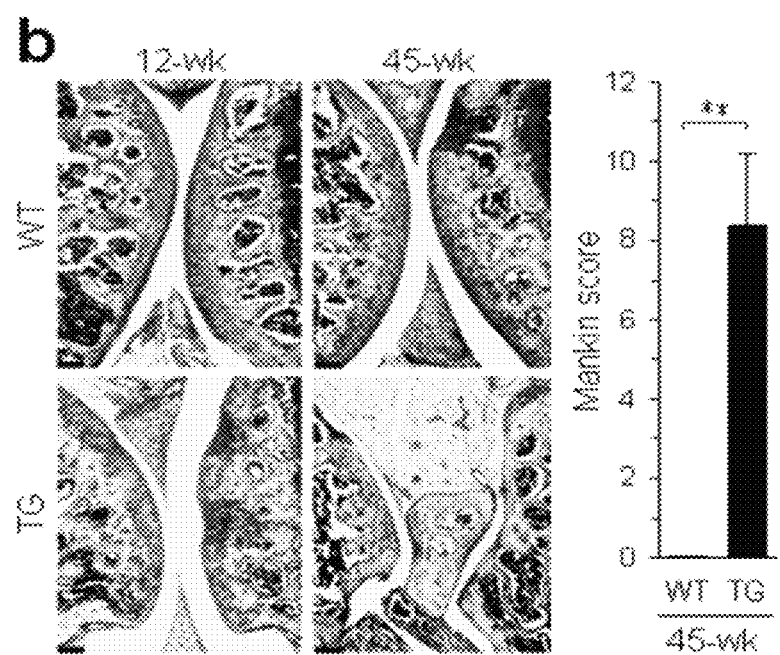
Figure 10C:
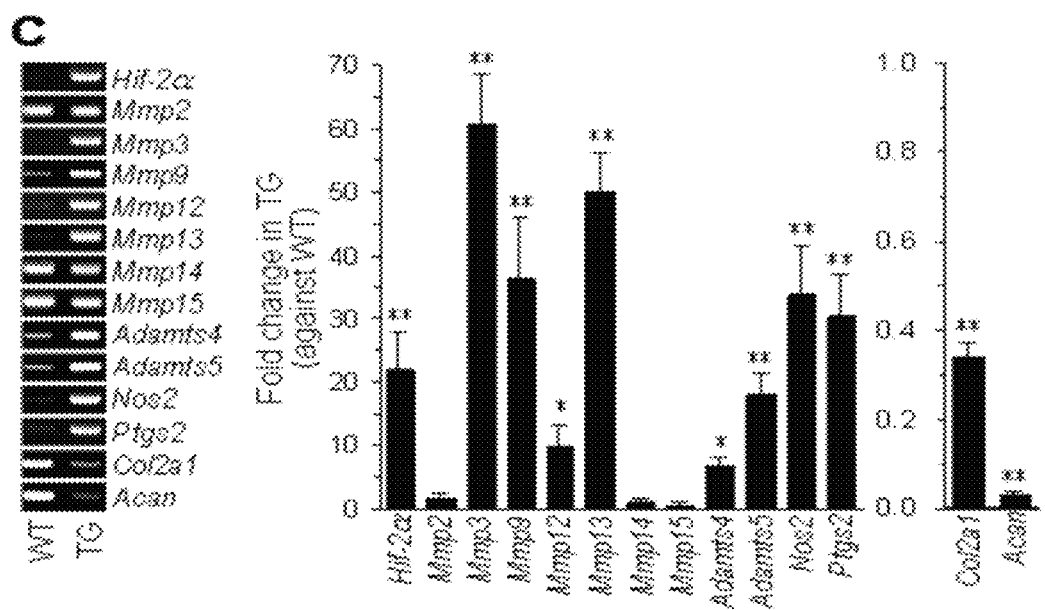

To confirm cartilage degeneration by HIF-2α, transgenic (TG) mouse in which HIF-2α is overexpressed specifically in chondrocytes was prepared. To prepare the transgenic mouse overexpressing chondrocyte-specific HIF-2α, a gene for transplantation was prepared first. A fragment (2.625 kb) of a mouse HIF-2α gene cleaved by NotI and NotI restriction enzymes was cloned into the NotI site of 4.35-kb pNass-beta vector (Clontech Laboratories, USA). Also, enhancer and promoter parts of 1.0-kb type II collagen (Col2a1) inducing cartilage-specific expression were cloned into the NotI site of the vector. The vector was cleaved with NotI to obtain a purified, 8.975-kb gene for transplantation. The gene for transplantation was microinjected into the pronucleus of a fertilized egg of a C57BL/6 mouse (Charles River, Japan). The fertilized egg with the gene inserted was implanted in the womb of a surrogate mouse to obtain at least 200 mice. Then, 10 transgenic mice were selected through PCR genotyping. It was confirmed that HIF-2α was overexpressed in the cartilage tissue of the HIF-2α transgenic mouse as compared to wild-type mouse (FIG. 10a). The cartilage of a 12-week-old or 45-week-old transgenic mouse or wild-type mouse was fixed in 4% paraformaldehyde (PFA, Sigma-Aldrich, USA) solution for 24 hours, reacted in 10% EDTA (Sigma-Aldrich, USA) solution for 2 weeks and prepared into a paraffin (Mc-Cormick, USA) block by increasing alcohol concentration. The paraffin block was sliced to 6-μm thickness and stained with safranin O. As a result, when compared with the 12-week-old wild-type mouse, slight irregularity was found in the HIF-2α transgenic mouse. In addition, when compared with the 45-week-old wild-type mouse, the cartilage of the HIF-2α transgenic mouse showed thinner and damaged cartilage tissue. The Mankin score indicative of cartilage damage was remarkably higher in the HIF-2α transgenic mouse than in the wild-type mouse, indicating that degenerative arthritis was induced (FIG. 10b). The expression of the target genes of HIF-2α, i.e. MMP (3, 9, 12, 13), ADAMTS4, PTGS2 and NOS, was significantly increased in the transgenic mouse (FIG. 10c).

Accordingly, it was confirmed that degenerative arthritis is induced and degenerative arthritis is induced owing to overexpression of the target genes of HIF-2α, i.e. MMP (3, 9, 12, 13), ADAMTS4, PTGS2 and NOS2, in cartilage tissue of a mouse wherein HIF-2α was overexpressed using Ad-HIF-2α or in that HIF-2α transgenic mouse.

Example 5

Prevention of Degenerative Arthritis Through Inhibition of HIF-2α Expression

Figure 11A:
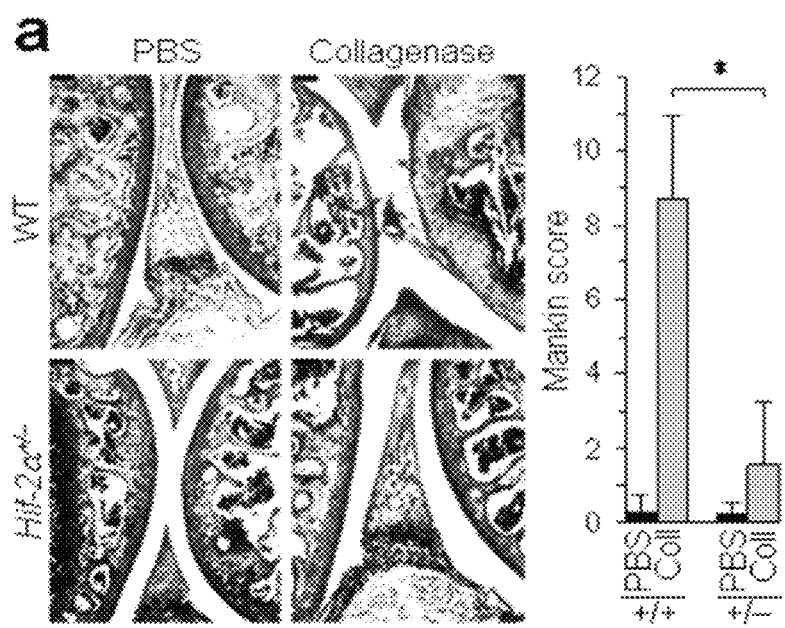
FIGS. 11a and 11b show a result of safranin O staining and quantification with Mankin score showing that injection of collagenase inhibits degenerative arthritis in HIF-2α-deficient gene-targeting mouse as compared to wild-type mouse (a) together with a result of quantifying gene transcripts of cartilage degeneration-inducing factors by RT-PCR and real-time RT-PCR (b). And, FIGS. 11c and 11d show a result of safranin O staining and quantification with Mankin score showing that degenerative arthritis is inhibited in HIF-2α-deficient gene-targeting mouse by destabilization of medial meniscus (DMM) (c) together with a result of quantifying gene transcripts of cartilage degeneration-inducing factors by RT-PCR and real-time RT-PCR (d).
Figure 11B:
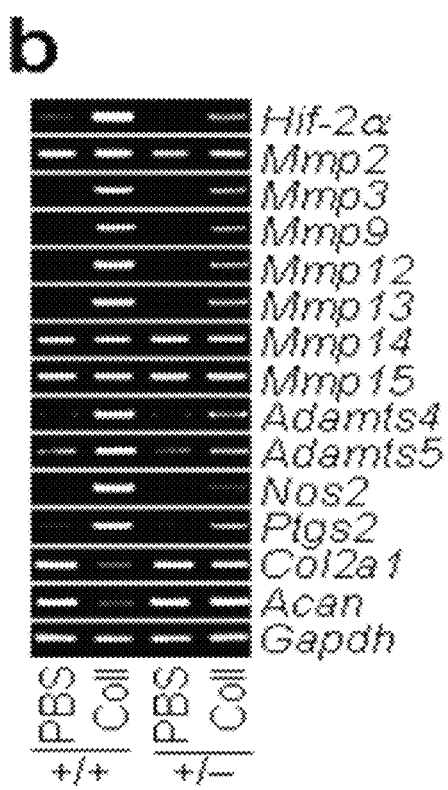
Figure 11C:
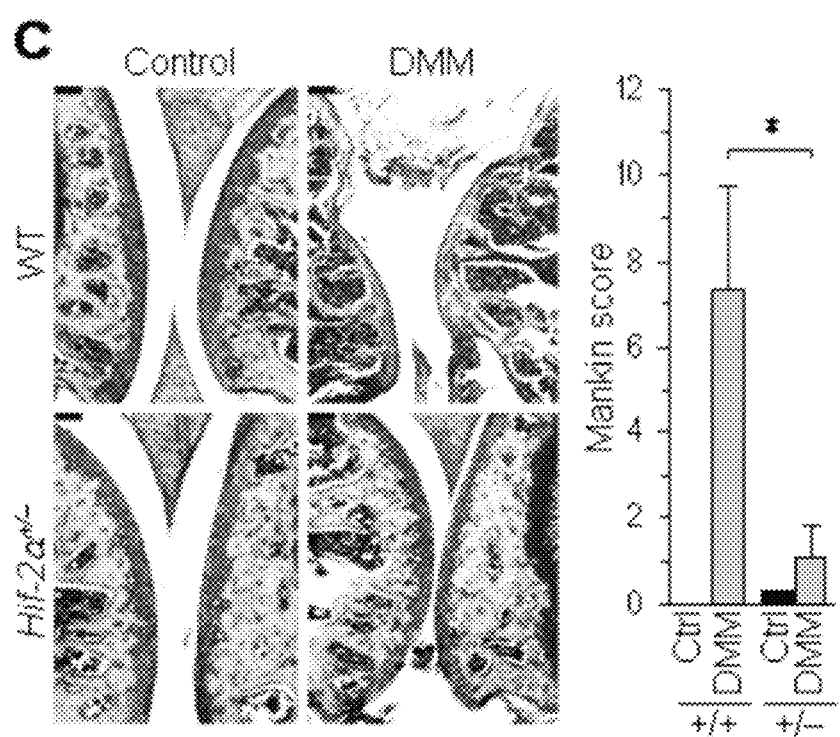
Figure 11D:
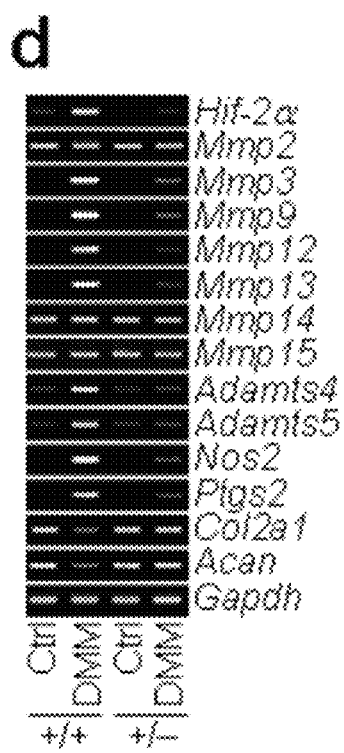
Figure 12A:
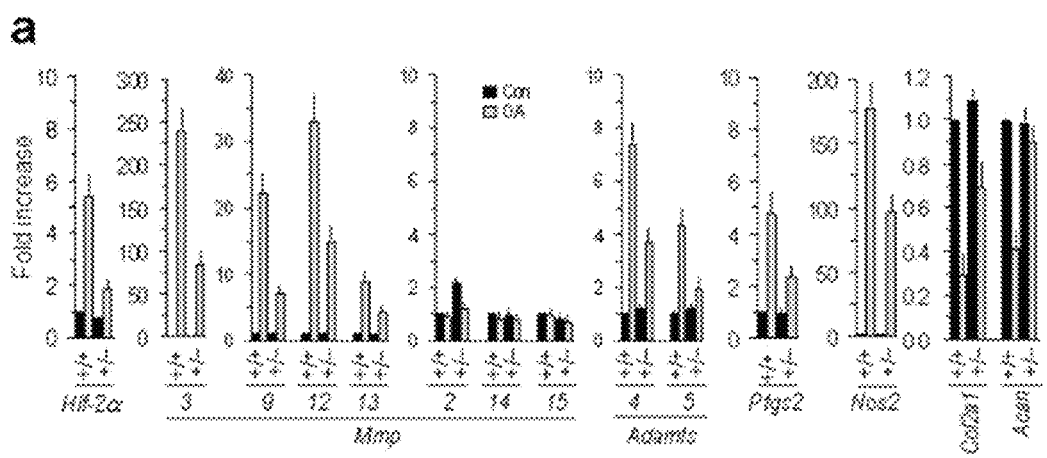
FIGS. 12a and 12b result of quantifying the gene transcripts shown in FIGS. 11b and 11c by real-time RT-PCR.
Figure 12B:
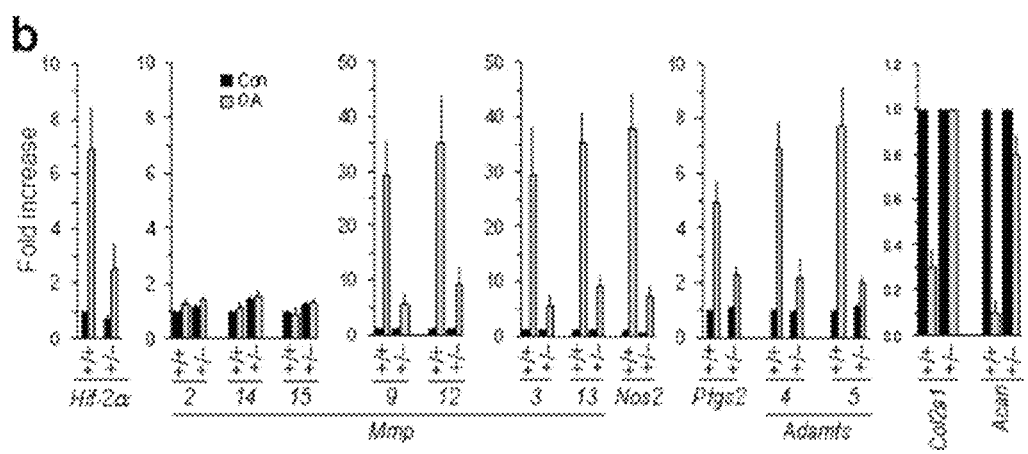

HIF-2α-deficient gene-targeting mouse (HIF-2α+/−) was used to more clearly demonstrate the inducement of degenerative arthritis by HIF-2α. Degenerative arthritis was experimentally induced in HIF-2α+/−(Jackson laboratory, USA) because a mouse with HIF-2α completely deficient (HIF-2α−/−) fail to grow beyond the embryonic state. More specifically, collagenase (1 unit) was injected to 10-to-12-week-old wild-type and HIF-2α+/−mice and knee joint was isolated and analyzed 28 days later. Then, degenerative arthritis was induced by destabilization of medial meniscus (DMM). 7 weeks later, the mouse knee joint was isolated and the degree of cartilage degeneration was analyzed. It was confirmed by safranin O staining that the cartilage of the normal mouse was severely damaged due to the collagenase treatment and DMM. In contrast, it was confirmed by safranin O staining and Mankin score that degenerative arthritis is clearly inhibited in the HIF-2α+/−mouse (FIGS. 11a and 11c). Also, when degenerative arthritis was induced by collagenase treatment and DMM, the expression of the cartilage degeneration-inducing factors MMP (3, 9, 12, 13), ADAMTS4, PTGS2 and NOS2 was increased in the wild-type mouse but not in the HIF-2α+/−gene-targeting mouse, as confirmed by RT-PCR (FIGS. 11a and 11c) and qRT-PCR (FIG. 12).

Accordingly, it can be seen that degenerative arthritis is not induced by collagenase treatment and DMM when HIF-2α is deficient. This suggests that HIF-2α is an important factor inducing cartilage degeneration and degenerative arthritis.

Example 6

Figure 13:
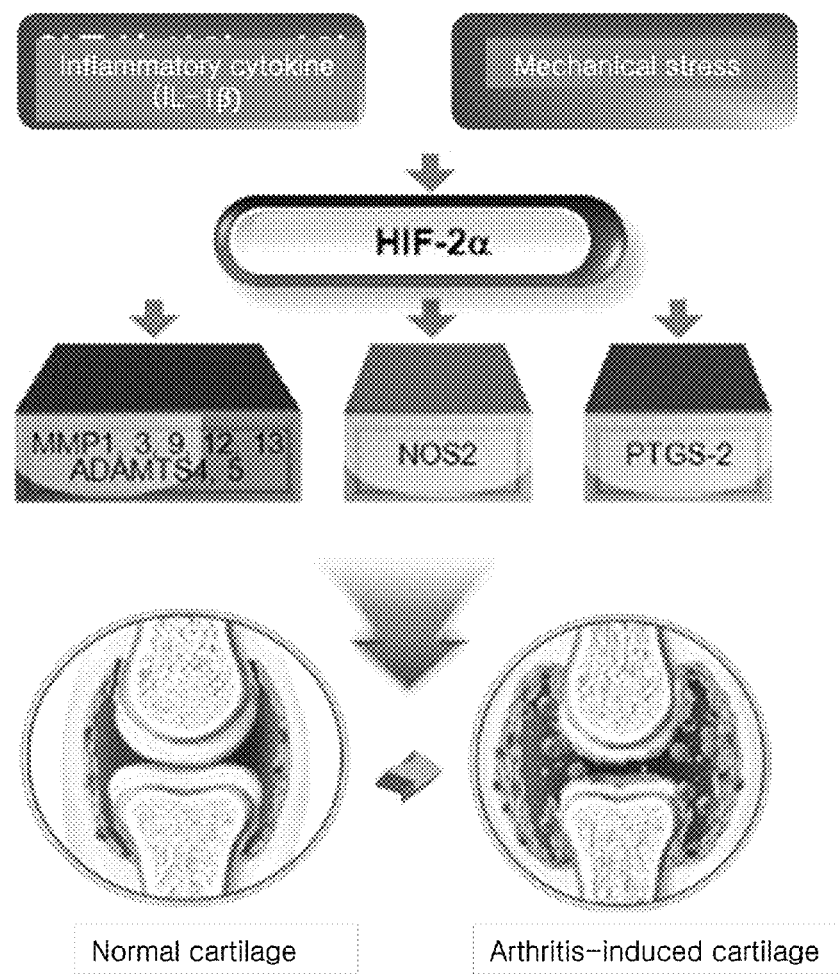
FIG. 13 is a schematic view describing a mechanism by which degenerative arthritis is induced by HIF-2α.

Prevention of Degenerative Arthritis Through Inhibition of HIF-2α Expression and Activation FIG. 13 is a schematic diagram describing a mechanism by which degenerative arthritis is induced by HIF-2α. The expression of HIF-2α in cartilage is increased owing to biochemical factors such as increased proinflammatory cytokines, damage to the extracellular matrix due to collagenase or mechanical stimulations such as DMM. The increase in HIF-2α induces the expression of its target genes, i.e. MMP (1, 3, 9, 12, 13), ADAMTS4, NOS2 and PTGS2. These factors ultimately induce degenerative arthritis by degrading the extracellular matrix and inducing degeneration of cartilage tissue. Accordingly, cartilage tissue degeneration and degenerative arthritis can be prevented by inhibiting expression or activation of HIF-2α.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for treating arthritis, comprising administering to a subject in need thereof a substance inhibiting the expression of the hypoxia-inducible factor-2α (HIF-2α) gene, wherein the substance is a siRNA, a shRNA, a miRNA or an antisense oligonucleotide.

2. The method according to claim 1, wherein the arthritis is osteoarthritis, degenerative joint disease, osteochondritis dissecans, ligament injuries, meniscus injuries, malalignment of joint, osteonecrosis, rheumatoid arthritis, juvenile idiopathic arthritis, trauma, inflammatory arthritis or septic arthritis caused by infection.

3. A method for treating arthritis, comprising administering to a subject in need thereof a substance inhibiting the expression of the hypoxia-inducible factor-2α (HIF-2α) gene, wherein the substance is a ribozyme or a DNAzyme.

* * * * *